(12) United States Patent
Banquy et al.

(10) Patent No.: US 11,426,490 B2
(45) Date of Patent: *Aug. 30, 2022

(54) MIXTURE OF POLYMERS, LUBRICATING FLUID AND POROUS MATERIALS COMPRISING SAID MIXTURE, AND SURFACE BEARING SAID MIXTURE

(71) Applicants: VALORISATION RECHERCHE, LIMITED PARTNERSHIP, Montréal (CA); VALORISATION HSJ, LIMITED PARTNERSHIP, Montréal (CA); CARNEGIE MELLON UNIVERSITY, Pittsburgh, PA (US)

(72) Inventors: Xavier Banquy, Saint-Laurent (CA); Jimmy Faivre, Villeurbanne (FR); Buddha Ratna Shrestha, Montreal (CA); Krzysztof Matyjaszewski, Pittsburgh, PA (US); Joanna Burdynska, Berkeley, CA (US); Florina Moldovan, Montréal (CA)

(73) Assignees: Valorisation-Recherche, Limited Partnership, Montreal (CA); Valorisation HSJ, Limited Partnership, Montreal (CA); Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/189,144

(22) Filed: Mar. 1, 2021

(65) Prior Publication Data
US 2021/0187166 A1 Jun. 24, 2021

Related U.S. Application Data

(63) Continuation of application No. 16/095,051, filed as application No. PCT/CA2017/050461 on Apr. 13, 2017, now Pat. No. 10,933,166.

(Continued)

(51) Int. Cl.
*A61L 27/50* (2006.01)
*A61L 27/16* (2006.01)
(Continued)

(52) U.S. Cl.
CPC ............... *A61L 27/50* (2013.01); *A61L 27/16* (2013.01); *A61L 31/10* (2013.01); *A61L 31/14* (2013.01);
(Continued)

(58) Field of Classification Search
CPC ...... A61L 27/50; A61L 31/14; A61L 2400/10; C10M 107/44; C10M 107/48;
(Continued)

(56) References Cited

U.S. PATENT DOCUMENTS 10,344,243 B2 * 7/2019 Putnam .................. A61K 47/66
10,933,166 B2 * 3/2021 Banquy ................ C10M 107/48
(Continued)

FOREIGN PATENT DOCUMENTS

WO 2014/063102 4/2014

OTHER PUBLICATIONS

International Search Report and Written Opinion for PCT Application No. PCT/CA2017/050461 dated Jul. 21, 2017.
(Continued)

*Primary Examiner* — Ellen M McAvoy
(74) *Attorney, Agent, or Firm* — Kowert, Hood, Munyon, Rankin & Goetzel, P.C.; Gareth M. Sampson

(57) ABSTRACT

A mixture of polymers with lubricating properties is provided. The polymer can be used to produce a lubricating fluid. They can also be born on a surface or embedded in a porous material. This mixture of polymers comprises (a) a pharmaceutically acceptable bottle-brush polymer comprising a backbone with polymeric pendant chains, and (b) a pharmaceutically acceptable linear polymer. In the lubricat-
(Continued)

ing fluid, the bottle-brush polymer and the linear polymer are dissolved together in a pharmaceutically acceptable solvent.

20 Claims, 37 Drawing Sheets

Related U.S. Application Data

(60) Provisional application No. 62/326,253, filed on Apr. 22, 2016.

(51) Int. Cl.

| | | |
|---|---|---|
| *C08F 265/06* | (2006.01) | |
| *C08B 37/08* | (2006.01) | |
| *C08L 51/00* | (2006.01) | |
| *C08L 5/08* | (2006.01) | |
| *A61L 31/10* | (2006.01) | |
| *A61L 31/14* | (2006.01) | |
| *C10M 107/44* | (2006.01) | |
| *C10M 107/48* | (2006.01) | |
| *C10M 173/02* | (2006.01) | |
| *C10N 40/00* | (2006.01) | |
| *C10N 50/02* | (2006.01) | |

(52) U.S. Cl.
CPC ........ *C08B 37/0072* (2013.01); *C08F 265/06* (2013.01); *C08L 5/08* (2013.01); *C08L 51/003* (2013.01); *C10M 107/44* (2013.01); *C10M 107/48* (2013.01); *C10M 173/02* (2013.01); *A61L 2400/06* (2013.01); *A61L 2400/10* (2013.01); *C08F 2438/01* (2013.01); *C10M 2201/02* (2013.01); *C10M 2217/003* (2013.01); *C10M 2225/025* (2013.01); *C10N 2040/50* (2020.05); *C10N 2050/02* (2013.01)

(58) Field of Classification Search
CPC ............ C10M 173/02; C10M 2201/02; C10M 2217/003; C10M 2225/025
See application file for complete search history.

(56) References Cited

U.S. PATENT DOCUMENTS

| | | |
|---|---|---|
| 2007/0287644 A1 | 12/2007 | Mitsui et al. |
| 2009/0104244 A1 | 4/2009 | Flanagan et al. |
| 2010/0072642 A1 | 3/2010 | Broad et al. |
| 2014/0142249 A1 | 5/2014 | Cho et al. |
| 2015/0072291 A1 | 3/2015 | Cho et al. |
| 2015/0072292 A1 | 3/2015 | Cho et al. |
| 2015/0275118 A1 | 10/2015 | Putnam et al. |
| 2016/0251508 A1* | 9/2016 | Hustad .................... C08L 83/10 524/504 |
| 2019/0194564 A1 | 6/2019 | Putnam et al. |
| 2019/0300811 A1 | 10/2019 | Tsou et al. |

OTHER PUBLICATIONS

Appleton et al. "Forced mobilization accelerates pathogenesis: characterization of a preclinical surgical model of osteoarthritis", Arthritis Research & Therapy (2008) 10:407).
Banquy et al. "Bioinspired bottle-brush polymer exhibits low friction and amontons-like behavior", J. Am. Chem. Soc., 136(17):6199-6202, 2014.
Chen et al. "Lubrication at Physiological Pressures by Polyzwitterionic Brushes." Science 2009, 323, 1698-1701.
Chen et al. "Polyzwitterionic Brushes: Extreme Lubrication by Design" Eur. Polym. J. 2011, 47, 511-523.
Dedinaite "Biomimetic Lubrication" Soft Matter 2012, 8, 273284.
Faivre et al. "Wear Protection without Surface Modification Using a Synergistic Mixture of Molecular Brushes and Linear Polymers", ACS Nano, 2017, vol. 11, p. 1762-1769.
Fouvry et al. "An Energy Description of Wear Mechanisms and Its Applications to Oscillating Sliding Contacts", Wear 2003, 255, 287-298.
Heuberger et al. "Topographic Information from Multiple Beam Interferometry in the Surface Forces Apparatus" Langmuir 1997, 13, 3839-3848.
Holmberg et al. "Global Energy Consumption Due to Friction in Passenger Cars" Tribol. Int. 2012, 47, 221-234.
Kaufman et al. "Nociceptive tolerance is improved by bradykinin receptor B1 antagonism and joint morphology is protected by both endothelin type A and bradykinin receptor B1 antagonism in a surgical model of osteoarthritis" Arthritis Research & Therapy (2011) 13:R76.
Klein et al. "Reduction of Frictional Forces between Solid-Surfaces Bearing Polymer Brushes" Nature 1994, 370, 634-636.
Klein "Shear, Friction, and Lubrication Forces between Polymer-Bearing Surfaces" Annu. Rev. Mater. Sci. 1996, 26, 581-612.
Klein "Chemistry. Repair or Replacement—a Joint Perspective." Science 2009, 323,47-8.
Kobayashi et al. "Chain Dimensions and Surface Characterization of Superhydrophilic Polymer Brushes with Zwitterion Side Groups." Soft Matter 2013, 9, 5138-5148.
Kobayashi et al, "Interferometry Study of Aqueous Lubrication on the Surface of Polyelectrolyte Brush" ACS Appl. Mater. Interfaces 2014, 6, 2036520371.
Liu et al. "Electrostatically Anchored Branched Brush Layers" Langmuir 2012, 28, 15537-47.
Liu et al. "Friction and High Load Bearing Capacity Layers Formed by Cationic-Block-Non-Ionic Bottle-Brush Copolymers in Aqueous Media" Soft Matter 2013, 9, 5361-5371.
Ma et al. "Origins of Hydration Lubrication" Nat. Commun. 2015, 6, 6060.
Maier et al. "Biological Adhesives. Adaptive Synergy between Catechol and Lysine Promotes Wet Adhesion by Surface Salt Displacement" Science 2015, 349, 628-32.
Matsushita et al. "Surface Grafting of Artificial Joints with a Biocompatible Polymer for reventing Periprosthetic Osteolysis" Nat. Mater. 2004, 3, 829-836.
Morse et al. "Biocompatible Polymer Brushes Grown from Model Quartz Fibres: Synthesis, Characterisation and in Situ Determination of Frictional Coefficient" Soft Matter 2010, 6, 1571-1579.
Ohsedo et al. "Surface Friction of Hydrogels with Well-Defined Polyelectrolyte Brushes" Langmuir 2004, 20, 6549-6555.
Perkin et al. "Dynamic Properties of Confined Hydration Layers" Faraday Discuss. 2009, 141, 399-413.
Petrone et al. "Mussel Adhesion Is Dictated by Time-Regulated Secretion and Molecular Conformation of Mussel Adhesive Proteins" Nat. Commun. 2015, 6, 8737.
Pettersson et al. "Lubrication Properties of Bottle-Brush Polyelectrolytes: An Afm Study on the Effect of Side Chain and Charge Density" Langmuir 2008, 24, 3336-3347.
Raviv et al. "Lubrication by Charged Polymers" Nature 2003, 425, 163-165.
Raviv et al. "Fluidity of Water Confined Down to Subnanometer Films" Langmuir 2004, 20, 532232.
Schmidt et al. "Boundary Lubrication of Articular Cartilage—Role of Synovial Fluid Constituents" Arthritis Rheum. 2007, 56, 882-891.
Sheiko et al. "Cylindrical Molecular Brushes: Synthesis, Characterization, and Properties" Prog. Polym. Sci. 2008, 33, 759-785.
Sotcheadt et al. "Electromechanical Probe and Automated Indentation Maps Are Sensitive Techniques in Assessing Early Degenerated Human Articular Cartilage" J. Orthopaedic Res. 2016 DOI: 10.1002/jor.23330.
Tairy et al. "Dense, Highly Hydrated Polymer Brushes Via Modified Atom-Transfer Radical-Polymerization: Structure, Surface Interactions, and Frictional Dissipation" Macromolecules 2015, 48, 140-151.

(56) References Cited

OTHER PUBLICATIONS

Tzanakis et al. "Future Perspectives on Sustainable Tribology" Renewable Sustainable Energy Rev. 2012, 16, 4126-4140.

* cited by examiner

P<P*

P>P*

MIXTURE OF POLYMERS, LUBRICATING FLUID AND POROUS MATERIALS COMPRISING SAID MIXTURE, AND SURFACE BEARING SAID MIXTURE

PRIORITY CLAIM

This application is a continuation of U.S. patent application Ser. No. 16/095,051, filed Oct. 19, 2018, which is a National Entry application of PCT application no PCT/CA/2017/050461 filed on Apr. 13, 2017 and published in English under PCT Article 21(2), which itself claims benefit of U.S. provisional application Ser. No. 62/326,253, filed on Apr. 22, 2016. All documents above are incorporated herein in their entirety by reference.

STATEMENT REGARDING FEDERALLY SPONSORED RESEARCH OR DEVELOPMENT

This invention was made with government support under DMR1436219 awarded by the National Science Foundation. The government has certain rights in the invention.

FIELD OF THE INVENTION

The present invention relates to a mixture of polymers with lubricating properties. More specifically, the present invention is concerned with a lubricating fluid and its use in providing lubrication at a desired site of action in or on a living body; a lubricated surface bearing the polymers, and a porous material having embedded therein said polymers.

BACKGROUND OF THE INVENTION

With the ever-increasing need of more efficient and long lasting machinery and devices, certain issues such as control of wear and fatigue of machine parts have become extremely challenging. The design of lubricating fluids able to protect surfaces against wear and high friction has been one the several tools used by engineers to improve machines' lifetimes.

It is generally assumed that damage caused during sliding, commonly known as "abrasive friction", is due to a high friction force and, therefore, a large coefficient of friction. Accordingly, to prevent surface damage or wear, one should aim to reduce the coefficient of friction, which has been the traditional focus of basic research into many bio- and non-biolubrication systems. However, many biological and nonbiological systems (especially involving soft polymeric surfaces) exhibit very complex behavior where the coefficient of friction and wear (abrasion) are not simply related and sometimes even have an inverse relationship. Therefore, other actors, such as the surface structure, the lubricant distribution and conformation, and the lubricant—surface interaction, are certainly more important than the coefficient of friction in determining the onset of wear.

Several diseases have a degenerative mechanical component, such as osteoarthritis (mechanical wear of joints), lacrimal fluid production deficiencies (dry eye syndrome), or vaginal dryness. Osteoarthritis occurs when protective cartilage situated at the ends of bones wear down over time. This can damage any joint in the body, and frequently affects hands, hips, knees, and the spine. Dry eye syndrome occurs when there is an insufficient or sub-optimal production of tears, usually due to an insufficient or sub-optimal production of lacrimal fluid. For each of the above diseases, the prior art discloses several treatments.

The prior art discloses that while no known cure exists for osteoarthritis, the pain can be reduced and joint movement can be maintained using various treatment methods, including medications (such as acetaminophen and nonsteroidal anti-inflammatory drugs), therapy (such as physical therapy and occupational therapy), and various surgical procedures (including joint replacement and bone realignment) and intra-articular injections (including cortisone shots and hyaluronic acid injections).

Various treatment methods for dry eye syndrome are known, including prescription medications. These include drugs to reduce eyelid inflammation; eye drops to control cornea inflammation; eye inserts; tear-stimulating drugs; and eye drops made from a patient's own blood. The prior art also discloses other procedures, such as closing tear ducts; using special contact lenses; unblocking oil glands; and using light therapy and eyelid massages.

Various treatment methods for vaginal dryness are also known, including lubricants and medication.

The prior art discloses hyaluronic acid and its use in various biomedical applications. Specifically, the use of hyaluronic acid to treat the above degenerative diseases is known, due to its anti-inflammatory as well as its chondroprotective qualities. For example, the prior art discloses that osteoarthritis may be treated by injecting hyaluronic acid into the joint where it increases the viscosity of synovial fluid and tempers inflammation processes. In addition, the prior art discloses that hyaluronic acid can be used in eye drops to treat dry eyes, as hyaluronic acid is found in the vitreous fluid of the eyes. Further, the prior art discloses that hyaluronic acid can be used to make a lubricant gel used in the treatment of vaginal dryness.

Turning now to another topic, bottle-brush polymers are also known, and such polymers are known to have various applications.

SUMMARY OF THE INVENTION

In accordance with the present invention, there is provided:

1. A lubricating fluid comprising:
   a. a bottle-brush polymer comprising a polymeric backbone with polymeric pendant chains, and
   b. a linear polymer,
   the bottle-brush polymer and the linear polymer being dissolved together in a solvent.
2. The lubricating fluid according to item 1, wherein the backbone of the bottle-brush polymer is acrylate or methacrylate based.
3. The lubricating fluid according to item 1 or 2, wherein the backbone of the bottle-brush polymer is poly(methacrylate) or a poly(alkyl methacrylate).
4. The lubricating fluid according to any one of items 1 to 3, wherein the backbone of the bottle-brush polymer is poly(methyl methacrylate).

5. The lubricating fluid according to any one of items 1 to 4, wherein the polymer in the pendant chains is attached directly to the backbone of the bottle-brush polymer or attached via a linking group.

6. The lubricating fluid according to item 5, wherein the polymer in the pendant chains is attached to the backbone of the bottle-brush polymer via the linking group.

7. The lubricating fluid according to item 5 or 6, wherein the linking group attaching the polymer in the pendant chains to the backbone of the bottle-brush polymer is a carboxylic acid, an ester, an amine, an azide, or a thiol functional group, or an alkylene, alkenylene, or alkylene group that is interrupted or not with one or more ester, amine, or azide, or thio functional group.

8. The lubricating fluid according to any one of items 1 to 7, wherein the pendant chains are zwitterionic.

9. The lubricating fluid according to any one of items 1 to 8, wherein the polymer in the pendant chains comprises poly(acrylic acid), poly(alkyl acrylic acid), poly(methacrylate), or poly(alkyl methacrylate).

10. The lubricating fluid according to item 9, wherein the polymer in the pendant chains comprises poly(methyl methacrylate).

11. The lubricating fluid according to any one of items 1 to 10, wherein the polymer in the pendant chains has attached thereto a substituent either directly or through a linking group.

12. The lubricating fluid according to item 11, wherein the substituent is attached through the linking group.

13. The lubricating fluid according to item 11 or 12, wherein the linking group attaching the substituent to the polymer in the pendant chains is a carboxylic acid, an ester, an amine, an azide, or a thiol functional group, or an alkylene, alkenylene, or alkylene group that is interrupted or not with one or more ester, amine, or azide, or thiol functional group.

14. The lubricating fluid according to any one of items 11 to 13, wherein the substituent is a phosphorylcholine group, a saccharide or disaccharide group including but not limited to glucose, sucrose, lactose and their derivatives, such as D-gluconolactone and lactobionolactone, or a biocompatible hydrophilic group such as hydroxy, oligo(ethylene oxide), carboxy, amino, sulfo, thiol, phosphate, or a derivative thereof.

15. The lubricating fluid according to any one of items 11 to 14, wherein the substituent is phosporylcholine.

16. The lubricating fluid according to any one of items 1 to 15, wherein the polymer in the pendant chains is poly(2-methacryloyloxyethyl phosphorylcholine) of formula:

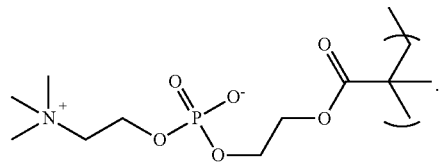

17. The lubricating fluid according to any one of items 1 to 16, wherein the bottle-brush polymer is a copolymer comprising the following two monomers:

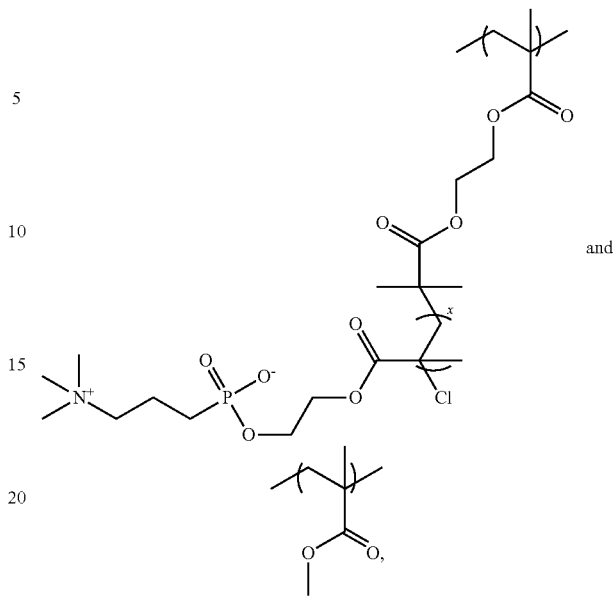

preferably a copolymer of formula:

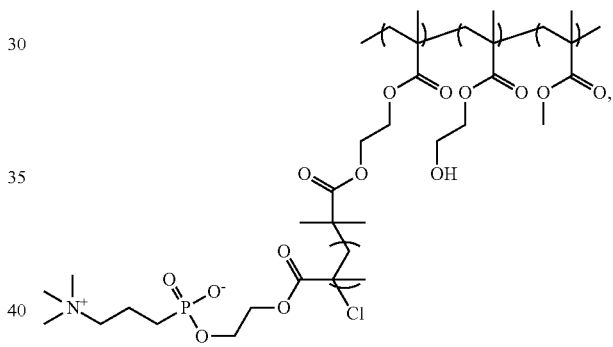

preferably with a grafting ratio between about 40% and about 60%, more preferably between about 45% and about 55%, and most of about 45% or about 55%.

18. The lubricating fluid according to any one of items 1 to 17, wherein the bottle-brush polymer is of formula:

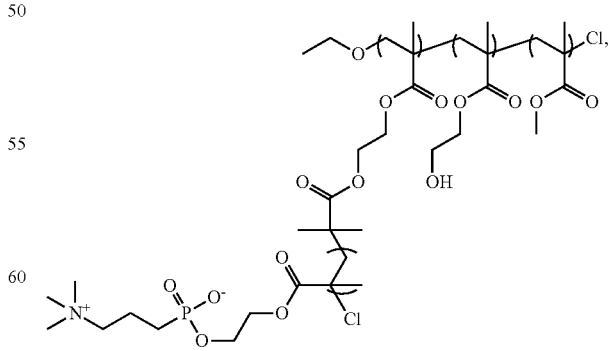

preferably with a grafting ratio from about 40% to about 60%, more preferably from about 45% to about 55%, and most preferably of about 45% or about 55%.

19. The lubricating fluid according to any one of items 1 to 18, wherein the bottle-brush polymer is (PBiBEM$_{540}$-g-PMPC$_{28}$)-stat-PHEMA$_{60}$-stat-PMMA$_{600}$ (PBiBEM$_{456}$-g-PMPC$_{35}$)-stat-PHEMA$_3$-stat-PMMA$_{370}$.
20. The lubricating fluid according to any one of items 11 to 9, wherein the polymer in the pendant chains comprises hyaluronic acid.
21. The lubricating fluid according to any one of items 11 to 14, wherein the substituent is a saccharide group or disaccharide.
22. The lubricating fluid according to item 21, wherein the substituent is glucose, sucrose, lactose, or a derivative thereof.
23. The lubricating fluid according to any one of items 1 to 22, wherein the bottle-brush polymer further comprises one or more capping blocks.
24. The lubricating fluid according to any one of items 11 to 23, wherein the molecular weight of the backbone is about 10 kDa, about 20 kDa, about 30 kDa, about 40 kDa, about 50 kDa, about 60 kDa, about 70 kDa, about 80 kDa, about 100 kDa, about 200 kDa, about 300 kDa, about 400 kDa, about 500 kDa, about 750 kDa, or about 900 kDa or more and/or about 1000 kDa, about 750 kDa, about 500 kDa, about 400 kDa, about 300 kDa, about 200 kDa or about 100 kDa or less.
25. The lubricating fluid according to any one of items 1 to 24, wherein the molecular weight of the backbone of the bottle-brush polymer is about 88700 Da.
26. The lubricating fluid according to any one of items 1 to 25, wherein the molecular weight of the pendant chain is about 1 kDa, about 5 kDa, about 10 kDa, about 20 kDa, about 30 kDa, about 40 kDa, about 50 kDa, about 60 kDa, about 70 kDa, about 80 kDa, or about 90 kDa or more and/or about 100 kDa, about 90 kDa, about 80 kDa, about 70 kDa, about 60 kDa, about 50 kDa, about 40 kDa, about 30 kDa, about 20 kDa, or about 15 kDa or less.
27. The lubricating fluid according to any one of items 1 to 26, wherein the molecular weight of the pendant chain is about 13275 Da.
28. The lubricating fluid according to any one of items 1 to 27, wherein a grafting ratio of the bottle-brush polymer is between about 30 and about 100%.
29. The lubricating fluid according to any one of items 1 to 28, wherein a grafting ratio of the bottle-brush polymer is about 30%, about 35%, about 40%, about 45%, or about 50% or more and/or about 100%, about 90%, about 80%, about 70%, about 65%, about 60%, about 55%, or about 50% or less.
30. The lubricating fluid according to any one of items 1 to 29, wherein the grafting ratio of the bottle-brush polymer is between about 40 and about 60%, preferably between about 45% and about 55%, most preferably is about 45% or about 55%.
31. The lubricating fluid according to any one of items 1 to 30, wherein the concentration of the bottle-brush polymer in the lubricating fluid is about 1, about 25, about 50, about 75, about 85, about 90, about 95, about 100, about 150, about 200, about 250, about 300, about 350, about 400, about 450, or about 500 ug/ml or more and/or about 10, about 5, about 1, about 0.5, about 0.25, or about 0.1 mg/mL or less.
32. The lubricating fluid according to any one of items 1 to 31, wherein the concentration of the bottle-brush polymer is 100 ug/mi or about 350 ug/ml.
33. The lubricating fluid according to any one of items 1 to 32, wherein the linear polymer is hyaluronic acid, dextran, poly(vinylpyrrolidone), poly(ethylene glycol), hydroxypropyl cellulose, a polymethacrylate polymer or copolymer, or a polyacrylate polymer or copolymer, or a (preferably pharmaceutically acceptable) salt thereof.
34. The lubricating fluid according to any one of items 1 to 33, wherein the linear polymer is hyaluronic acid or poly(vinylpyrrolidone), or a (preferably pharmaceutically acceptable) salt thereof; preferably hyaluronic acid or a (preferably pharmaceutically acceptable) salt thereof.
35. The lubricating fluid according any one of items 1 to 34, wherein the linear polymer is partially crosslinked.
36. The lubricating fluid according to any one of items 1 to 35, wherein the linear polymer has a molecular weight of about 5 kDa, about 10 kDa, about 25 kDa, about 50 kDa, about 100 kDa, about 250 kDa, or about 500 kDa or more and/or 10 MDa, about 8 MDa, or about 5 MDa or less.
37. The lubricating fluid according to any one of items 1 to 36, wherein the concentration of linear polymer in the lubricating fluid is about 0.001 mg/mL, 0.005 mg/mL, 0.01 mg/mL, 0.05 mg/mL, 0.1 mg/mL, 0.5 mg/mL, about 1 mg/mL, about 2 mg/mL, or about 5 mg/mL or more, preferably about 0.01 mg/mL or more, more preferably about 0.1 mg/mL or more, yet more preferably about 1 mg/mL or more, and most preferably about 0.9 mg/mL or about 2 mg/ml.
38. The lubricating fluid according to any one of items 1 to 37, comprising the bottle-brush polymer and the linear polymer in a bottle-brush polymer:linear polymer weight ratio between about 1:1 and about 1:20, preferably between about 1:2.5 and about 1:15, more preferably between about 1:5 and about 1:10.
39. The lubricating fluid according to any one of items 1 to 38, wherein the solvent is saline, preferably isotonic, preferably buffered at a pH of about 7 to about 7.4.
40. The lubricating fluid according to any one of items 1 to 39, wherein the solvent is phosphate-buffered saline (PBS).
41. The lubricating fluid according to any one of items 1 to 40, further comprising one or more additive.
42. The lubricating fluid according to any one of items 1 to 41, consisting of pharmaceutically acceptable ingredients only.
43. The lubricating fluid according to any one of items 1 to 42, further comprising one or more therapeutic agent.
44. Use of a lubricating fluid as defined in any one of items 1 to 43 in providing lubrication at a desired site of action.
45. A method of method providing lubrication at a desired site of action, the method comprising the step of applying a lubricating fluid as defined in any one of items 1 to 43 at said site of action.
46. Use of a lubricating fluid as defined in item 42 or 43 in providing lubrication at a desired site of action in or on a living body e.g. of a human.
47. The use of item 46, wherein the desired site of action is an eye, skin, a surface of a ligament, preferably a recently operated ligament, a vagina, a joint, a gastrointestinal tract, a nasal duct, a tracheal duct, or a stomach.
48. A method of lubricating a tissue of a living body e.g. of a human, the method comprising the step of contacting the lubricating fluid as recited in item 42 or 43 with said tissue.
49. The method of item 48, wherein the tissue is an eye, skin, a surface of a ligament, preferably a recently operated ligament, a vagina, a joint, a gastrointestinal tract, a nasal duct, a tracheal duct, or a stomach.
50. Use of a lubricating fluid as defined in item 42 or 43 for the treatment of a disease having a degenerative mechanical component.

51. The use of item 50, wherein the disease is osteoarthritis, a lacrimal fluid production deficiency, or vaginal dryness.
52. A method of treating a disease having a degenerative mechanical component, the method comprising administering a lubricating fluid as defined in item 42 or 43 to a tissue affected by the disease.
53. The method of item 51, wherein the disease is osteoarthritis, a lacrimal fluid production deficiency, or vaginal dryness.
54. The method of any one of items 48, 49, 52, and 53, wherein the lubricating fluid is administered by injection.
55. The method of any one of items 48, 49, 52, and 53, wherein the lubricating fluid is administered intravaginally.
56. The method of any one of items 48, 49, 52, and 53, wherein the lubricating fluid is administered topically.
57. The method of anyone of items 48, 49, 52, and 53, wherein the lubricating fluid is administered intranasally.
58. The method of any one of items 48, 49, 52, and 53, wherein the lubricating fluid is administered orally.
59. A synthetic synovial fluid comprising a lubricating fluid as defined in item 42 or 43.
60. The synthetic synovial fluid according to item 59, being for use in the treatment of osteoarthritis.
61. Eye drops comprising a lubricating fluid as defined in item 42 or 43.
62. The eye drops according to item 61, being for use in the treatment of dry eye.
63. A vaginal lubricating composition comprising a lubricating fluid as defined in item 42 or 43.
64. The composition according to item 63, being for use in treating vaginal dryness and/or infertility related to vaginal dryness.
65. Use of a lubricating fluid as recited in any one of items 1 to 43 in lubricating a medical instrument.
66. The use of item 65, wherein the medical instrument is a syringe, an injection device, or an elution device
67. A method of lubricating of a surface of a medical instrument comprising the step of contacting a lubricating fluid as defined in any one of items 1 to 43 with said surface,
68. The method of item 67, wherein the medical instrument is a syringe, an injection device, or an elution device
69. A mixture comprising:
    a) a bottle-brush polymer comprising a polymeric backbone with polymeric pendant chains, and
    b) a linear polymer,
    wherein the bottle-brush polymer and the linear polymer are as defined in any one of item 1 to 43.
70. The mixture of item 69, wherein the bottle-brush polymer and the linear polymer are pharmaceutically acceptable.
71. The mixture of item 69 or 70, being in solid form, preferably in the form of a powder.
72. Use of a mixture as defined in any one of items 69 to 71 for producing the lubricating fluid of any one of item 1 to 43.
73. A method for producing the lubricating fluid of any one of item 1 to 43, the method comprising the step of contacting a mixture as defined in any one of items 69 to 71 with a solvent, and allowing dissolution of the mixture in the solvent.
74. The method of item 73, further comprising mixing the mixture with the solvent to speed said dissolution.
75. The method of item 73 or 74, wherein the bottle-brush polymer, the linear polymer, the solvent, and the lubricating fluid are pharmaceutically acceptable.
76. The method of item 75, wherein, before said contacting step, the mixture is administered to a subject, and wherein said dissolution occurs in vivo, preferably at a site of action of the lubricating fluid.
77. The method of item 76, wherein the solvent is a body fluid.
78. The method of item 77, wherein the mixture is administered orally in the form of an oral formulation for releasing the linear polymer and the bottle-brush polymer in a gastrointestinal tract, and wherein, upon release, the linear polymer and the bottle-brush polymer contact and dissolve in a fluid present in the gastrointestinal tract.
79. The method of item 76, wherein the solvent is an extraneous solvent.
80. A surface bearing a polymeric layer, the polymeric layer comprising:
    a) a bottle-brush polymer comprising a polymeric backbone with polymeric pendant chains, and
    b) a linear polymer,
    wherein the bottle-brush polymer and the linear polymer are as defined in any one of item 1 to 43.
81. The surface of item 80, wherein the polymeric layer releases the bottle-brush polymer and the linear polymer when the surface contacts a solvent.
82. The surface of item 80, wherein the bottle-brush polymer and the linear polymer remain in the polymeric layer on the surface for a period of time when the surface is in contact with a solvent.
83. The surface of item 80 or 81, wherein said solvent is a body fluid.
84. The surface of any one of items 80 to 83, wherein the polymeric layer comprises the bottle-brush polymer and the linear polymer in a bottle-brush polymer:linear polymer weight ratio between about 1:5 and about 1:15, preferably between about 1:7 and about 1:12, more preferably between about 1:8 and about 1:9, most preferably of about 1:9.
85. The surface of any one of items 80 to 84, being a surface of an ophthalmic lens, a surface of the barrel of a syringe, a surface of an injection device, a surface of an elution device, or a surface of an implant.
86. The surface of any one of items 80 to 86, wherein the bottle-brush polymer and the linear polymer are pharmaceutically acceptable.
87. A porous material having embedded therein:
    a) a bottle-brush polymer comprising a polymeric backbone with polymeric pendant chains, and
    b) a linear polymer,
    wherein the bottle-brush polymer and the linear polymer are as defined in any one of item 1 to 43.
88. The porous material of item 87, wherein the porous material is a gel, a sponge, a textile or textile fibers.
89. The porous material of item 87 or 88, wherein the bottle-brush polymer, the linear polymer, and the polymer material are pharmaceutically acceptable.
90. The porous material of any one of items 87 to 89, wherein the porous material comprises the bottle-brush polymer and the linear polymer in a bottle-brush polymer:linear polymer weight ratio between about 1:5 and about 1:15, preferably between about 1:7 and about 1:12, more preferably between about 1:8 and about 1:9, most preferably of about 1:9.

DETAILED DESCRIPTION OF THE INVENTION

Lubricating Fluid

Turning now to the invention in more detail, there is provided a lubricating fluid.

A lubricating fluid is a fluid provides lubrication at various desired sites of action. In embodiments, the fluid is a pharmaceutical lubricating fluid, i.e. a lubricating fluid that is pharmaceutically acceptable and that can be used to provide lubrication at various desired sites of action, including in or on a living body, for example in the eyes, vagina, or joints of e.g. a human.

The fluid may present different viscosities, from a watery consistency to a gel-like consistency, depending on its end-use.

The lubricating fluid of the invention comprises:
a) a acceptable bottle-brush polymer comprising a polymeric backbone with polymeric pendant chains, and b) a acceptable linear polymer,
the bottle-brush polymer and the linear polymer being dissolved together in a solvent.

In embodiments, either, some of or preferably all of the bottle-brush polymer, the linear polymer, and the solvent are pharmaceutically acceptable.

Figure 1:
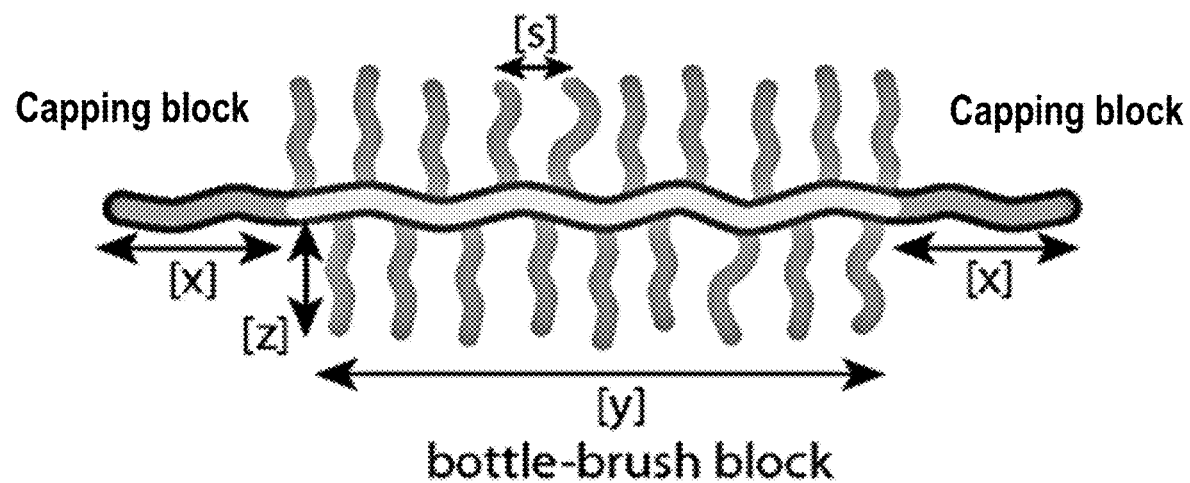
FIG. 1 shows the architecture of the bottle brush polymer.

The term "bottle-brush polymer" refers to a polymer comprising a linear polymeric backbone with multiple polymeric pendant chains attached to the backbone. FIG. 1 shows the typical architecture of a bottle-brush polymer. The aforementioned backbone and pendant chains form the "bottle-brush" block in this polymer. Optional "capping blocks" located at either or both ends of the linear backbone of the "bottle-brush" block are also shown in FIG. 1.

The bottle-brush polymer can be characterized by its grafting ratio. The grafting ratio represents the percentage of repeat units of the backbone of the bottle-brush polymer that bear a polymeric pendant chain. For the bottle-brush polymer comprised in the present lubricating fluid, the grafting ratio typically ranges between about 30 and about 100%. In preferred embodiments of the invention, the grafting ratio is about 30%, about 35%, about 40%, about 45%, or about 50% or more and/or about 100%, about 90%, about 80%, about 70% N, about 65%, about 60%, about 55%, or about 50% or less. In most preferred embodiments, the grafting ratio is between about 40 and about 60%, preferably between about 40% and about 55%, more preferably between about 40% and about 50%, yet more preferably is about 45%.

The bottle-brush polymer can also be characterized by the molecular weight of its backbone and the molecular weight of its pendant chains. In embodiments, the molecular weight of the backbone is about 10 kDa, about 20 kDa, about 30 kDa, about 40 kDa, about 50 kDa, about 60 kDa, about 70 kDa, about 80 kDa, about 100 kDa, about 200 kDa, about 300 kDa, about 400 kDa, about 500 kDa, about 750 kDa, or about 900 kDa or more and/or about 1000 kDa, about 750 kDa, about 500 kDa, about 400 kDa, about 300 kDa, about 200 kDa, or about 100 kDa or less. In preferred embodiments, the molecular weight of the backbone is about 90 kDa (e.g. 88700 Da). In embodiments, the molecular weight of the pendant chain is about 1 kDa, about 5 kDa, about 10 kDa, about 20 kDa, about 30 kDa, about 40 kDa, about 50 kDa, about 60 kDa, about 70 kDa, about 80 kDa, or about 90 kDa or more and/or about 100 kDa, about 90 kDa, about 80 kDa, about 70 kDa, about 60 kDa, about 50 kDa, about 40 kDa, about 30 kDa, about 20 kDa, or about 15 kDa or less. In preferred embodiments, the molecular weight of the pendant chain is about 15 kDa (e.g. 13275 Da).

The bottle-brush polymer is also characterized by the nature of the repeat units in its backbone and the nature of the pendant chains.

The nature of the repeat units of the backbone of the bottle-brush polymer is chosen so that it produces polymer (preferably a pharmaceutically acceptable polymer) and allows for post-grafting of the pendant chains. The grafting of the pendant chains may be achieved using the "grafted from" or "grafting to" methods. In the "grafted from" approach, the pendant chains are grown from a macromolecular chain bearing initiator functional groups. In the "grafting to" approach, the pendant chains are polymerized separately and grafted to the main chain afterwards.

In embodiments, the backbone of the bottle-brush polymer may be acrylate based (e.g. poly(acrylic acid), a poly(acrylate), such as poly(alkyl acrylate) and more specifically poly(methyl acrylate)) or methacrylate based (e.g. poly(methacrylic acid), a poly(methacrylate), such as poly(alkyl methacrylate) and more specifically poly(methyl methacrylate)). In preferred embodiments, the backbone of the bottle-brush polymer is poly(methacrylic acid) or a poly(alkyl methacrylate), such as e.g. poly(methyl methacrylate).

As noted above, the pendant chains of the bottle-brush polymer are polymeric. The polymer in these pendant chains may be attached directly to the backbone of the bottle-brush polymer or attached via a linking group.

Suitable linking groups (for attaching the polymer of the pendant chain to the backbone of the bottle-brush polymer) include carboxylic acid, ester, amine, azide, and thiol functional groups as well as alkylene, alkenylene, and alkynylene groups, the alkylene, alkenylene, and alkynylene groups being interrupted or not with one or more ester, amine, azide, and/or thiol functional groups. Herein "interrupted" means that a functional group (ester, amine, azide, or thiol) is located at either end or in between two carbon atoms of the alkylene, alkenylene, and alkynylene groups.

In embodiments, the pendant chains are zwitterionic.

In embodiments, the polymer in the pendant chains is hyaluronic acid.

In other embodiments, the polymer in the pendant chains is poly(acrylic acid), a poly(acrylate)—such as a poly(alkyl acrylate) e.g. a poly(methyl acrylate—poly(methacrylic acid), a poly(methacrylate)—such as a poly(alkyl methacrylate) e.g. poly(methyl methacrylate). These polymer can optionally have attached thereto, directly or indirectly through a linking group, a substituent. Examples of such a substituent include phosphorylcholine

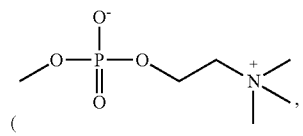
( the open link attached to the oxygen atom on the left indicating the bond attaching the phosphorylcholine to the rest of the molecule), saccharide and disaccharide groups, including but not limited to glucose, sucrose, lactose and their derivatives such as D-gluconolactone and lactobionolactone, as well biocompatible hydrophilic groups such as hydroxy, oligo(ethylene oxide), carboxy, amino, sulfo, thiol, phosphate, and derivatives thereof. Suitable linking groups (for attaching such substituent to the polymer of the pendant chain) include carboxylic acid, ester, amine, azide, and thiol functional groups as well as alkylene, alkenylene, and alkynyene groups, the alkylene, alkenylene, and alkynylene groups being interrupted or not with or more ester, amine, azide, and/or thiol functional groups.

In preferred embodiments, the polymer in the pendant chains is poly(methyl methacrylate).

In preferred embodiments, the polymer in the pendant chains has attached thereto said substituent, preferably through said linking group.

In preferred embodiments, the substituent is phosphorylcholine.

In preferred embodiments, the polymer in the pendant chains is poly(2-methacryloyloxyethyl phosphorylcholine of formula:

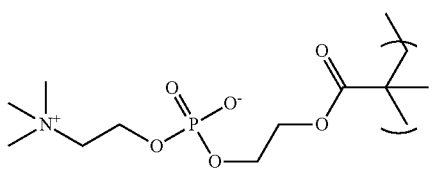

and in embodiments:

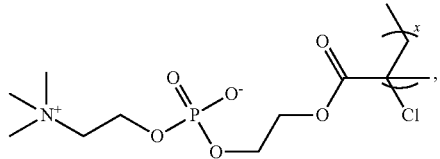

wherein x represents the number of repeat unit and, in embodiments, varies between 0 and 1000. In embodiments, x is preferably varies between 10 and 100, and more preferably between 10 and 50.

In embodiments, the bottle-brush polymer is a copolymer comprising the following two monomers:

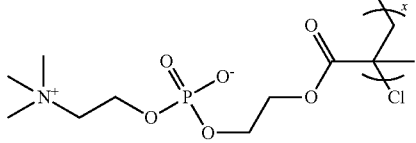

wherein x is as defined above. In embodiments, the copolymer has a grafting ratio, between about 40% and about 60% (in other words, it comprises about 40% to about 60% of the monomer on the left), preferably it has a grafting ratio between about 45% and about 55%, and more preferably a grafting ratio of about 45% or about 55%.

In embodiments, the bottle-brush polymer is (PBiBEM-g-PMPC)-stat-PHEMA-stat-PMMA:

preferably

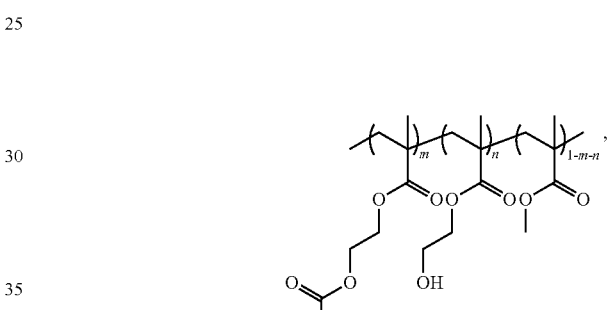

and more specifically:

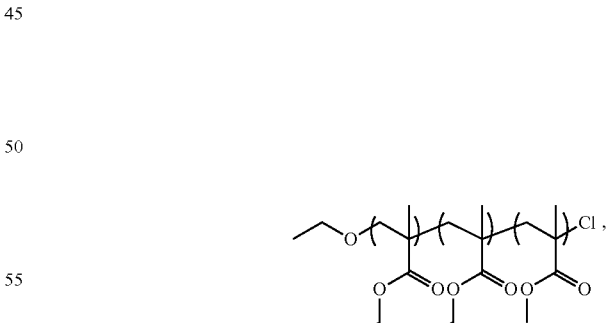

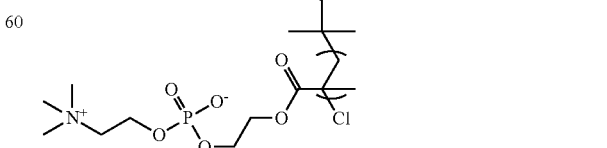

preferably:

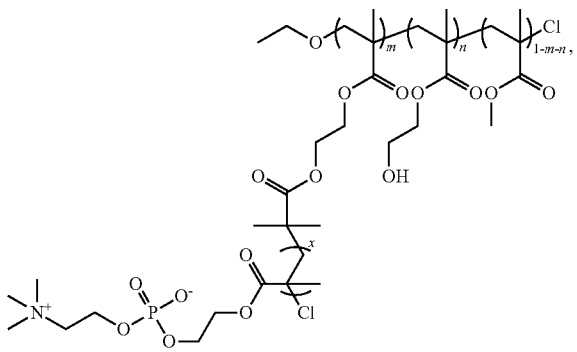

wherein x is as defined above and m and n represent repeat unit ratios (e.g. m=number of repeat units of the formula on the left/total number of repeat units in polymer and as such vary between 0 and 1. In embodiments, this bottle-brush polymer has a grafting ratio as described above, i.e. between about 30% and about 100% (i.e. m varies from about 0.3 to about 1). In preferred embodiments, the grafting ratio is about 30%, about 35%, about 40%, about 45%, or about 50% or more and/or about 100%, about 90%, about 80%, about 70%, about 65%, about 60%, or about 55% or about 50% less. In more preferred embodiments, the grafting ratio varies from about 40% to about 60% (i.e. m varies from about 0.4 to about 0.6), preferably about 45% to about 55% (i.e. m varies from about 0.45 to about 0.55), more preferably about 40% to about 50% (i.e. m varies from about 0.4 to about 0.5), and yet more preferably is about 45% or about 55% (m is about 0.45 or about 0.55). In embodiments, this bottle-brush polymer comprises a minor proportion of PHEMA, i.e. n is about 0.15, about 0.10, about 0.08, about 0.05, about 0.04, about 0.03, about 0.02, about 0.01, about 0.0075, about 0.005, or about 0.004 or less, preferably n is about 0.05 or less; or is about 0.05 or about 0.004. In preferred embodiments, the bottle brush polymer is of formula (PBiBEM$_{540}$-g-PMPC$_{28}$)-stat-PHEMA$_{60}$-stat-PMMA$_{600}$ or (PBiBEM$_{456}$-g-PMPC$_{35}$)-stat-PHEMA$_{3}$-stat-PMMA$_{370}$, wherein the numbers represent the number of repeat units in the polymer (i.e. in these polymers m=540/1200=0.45 and n=60/1200=0.05 and m=456/829=0.55 and n=3/829=0.0036, respectively).

In any of the above embodiments, the bottle-brush polymer may further comprise one or more aforementioned "capping blocks". A capping block is a functional group, a substituent, or a polymer or peptide attached at either or both ends of the backbone of the bottle-brush polymer. The nature of capping blocks will be chosen according to the properties to be imparted to the bottle-brush polymer. For example, capping blocks might be included to improve adhesion of the bottle-brush polymer to biological surfaces or biopolymers. Suitable capping blocks include alkyl, alkene or alkyne groups optionally bearing one or more thiol, amine, carboxylic, and/or azide functional groups, peptides, as well as polymer chains bearing said functional groups or peptides.

In embodiments, the concentration of bottle-brush polymer is about 1, about 25, about 50, about 75, about 85, about 90, about 95, about 100, about 150, about 200, about 250, about 300, about 350, about 400, about 450, or about 500 ug/ml or more and/or about 10, about 5, about 1, about 0.5, about 0.25, or about 0.1 mg/mL or less. In preferred embodiments, the concentration of bottle-brush polymer is about 100 ug/ml (i.e. 0.1 mg/mL) or about 350 ug/ml.

The linear polymer is a polymer that, contrary to the bottle-brush polymer, has a linear structure. It is thus free from polymeric pendant chains.

In embodiments, the linear polymer has a molecular weight of about 5 kDa, about 10 kDa, about 25 kDa, about 50 kDa, about 100 kDa, about 250 kDa, or about 500 kDa or more and/or 10 Mda, about 8 Mda, or about 5 Mda or less. In embodiments, the linear polymer has a molecular weight of about 1.5 Mda, about 500 kDa, about 50 kDa or about 10 kDa.

In embodiments, the linear polymer is:
hyaluronic acid:

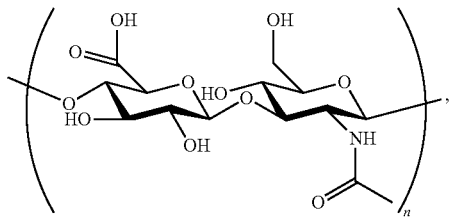

dextran:

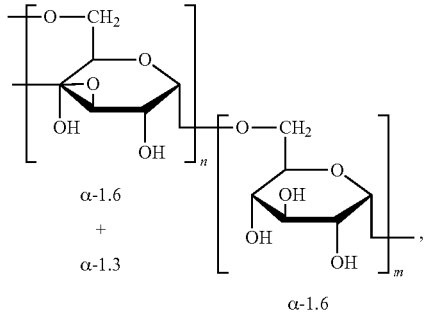

poly(vinylpyrrolidone):

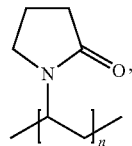

or
poly(ethylene glycol):

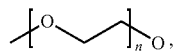

hydroxypropyl cellulose,
a polymethacrylate polymer or copolymer, or
a polyacrylate polymer or copolymer,
wherein m and n represent the number of repeat units, or a (preferably pharmaceutically acceptable) salt thereof. In preferred embodiments, the number of repeat units is such that the linear polymer has the abovementioned molecular weights. In embodiments, the linear polymer is partially crosslinked to achieve these molecular weights.

In preferred embodiments, the linear polymer is hyaluronic acid or a (preferably pharmaceutically acceptable salt) thereof, for example sodium hyaluronate.

In other preferred embodiments, the linear polymer is poly(vinylpyrrolidone).

In embodiments, the concentration of the linear polymer in the lubricating fluid is about 0.001 mg/mL, 0.005 mg/mL, 0.01 mg/mL, 0.05 mg/mL, 0.1 mg/mL, 0.5 mg/mL, about 1 mg/mL, about 2 mg/mL, or about 5 mg/mL or more. In preferred embodiments, the concentration of the linear polymer in the lubricating fluid is about 0.01 mg/mL or more, and more preferably about 0.1 mg/mL or more, yet more preferably about 1 mg/mL or more, and most preferably about 0.9 mg/mL or about 2 mg/mL.

In embodiments, the lubricating fluid comprises the bottle-brush polymer and the linear polymer in a bottle-brush polymer:linear polymer weight ratio between about 1:1 and about 1:20, preferably between about 1:2.5 and about 1:15, more preferably between about 1:5 and about 1:10.

In embodiments, the bottle-brush polymer and the linear polymer are present in the lubricating fluid at a bottle-brush polymer:linear polymer weight ratio between about In embodiments, the solvent is saline (i.e. an aqueous solution of mainly NaCl), preferably isotonic, preferably buffered at a pH of about 7 to about 7.4 using for example a phosphate buffer. In embodiments, the solvent is phosphate-buffered saline (PBS).

The lubricating fluid may further comprise one or more additive, such as for example preservatives, colorants, flavorings, and odorants. In embodiments, the additives are pharmaceutically acceptable.

Herein, "pharmaceutically acceptable" means generally accepted for use in pharmaceutical products. Of note, as is well know to the skilled person, whether a product is pharmaceutically acceptable depends on the end use of the lubricating fluid. For example, components that may be acceptable in a fluid intended to be applied topically may not be acceptable when the fluid is intended to be administered by injection.

The lubricating fluid may further comprise one or more therapeutic agent. Such therapeutic agents may be chosen according to the end use of the lubricating fluid. For example, when the fluid is for application to the eye, compounds know to be applied to the eye for treating various conditions may also be incorporated in the fluid. In such embodiments, the lubricating fluid is preferably a pharmaceutical lubricating fluid, i.e. a lubricating fluid that consists of pharmaceutically acceptable ingredients (i.e. polymers, solvents, additives, etc.) only.

Use and Properties of the Lubricating Fluid.

The present invention also provides the use of the above lubricating fluid in providing lubrication at a desired site of action. There is also provided a method of providing lubrication at a desired site of action comprising the step of applying the lubricating fluid at said site of action.

In embodiments, the site of action is in or on a living body of e.g. a human, for example the living body of a human. There is thus also provided a method of lubricating a tissue of a living body of e.g. a human comprising the step of contacting the lubricating fluid with said tissue. In such embodiments, the lubricating fluid preferably consists of pharmaceutically acceptable ingredients (i.e. polymers, solvents, additives, etc.) only.

In embodiments, the site of action and/or tissue is the eye, the skin, a surface of a ligament, preferably a recently operated ligament, the vagina, a joint, the gastrointestinal tract, the nasal duct, the tracheal duct, or the stomach.

The use of this fluid is preferably for the treatment of diseases having a degenerative mechanical component, such as osteoarthritis (mechanical wear of joints), lacrimal fluid production deficiencies (dry eye syndrome), or vaginal dryness.

The lubricating fluid may be administered in various ways according the condition to be treated. For example, the lubricating fluid may be administered:

by injection e.g. intra-particularly (in an articulation to be treated), intravaginally (in the vagina), topically, for example to the eye (on the cornea), to the skin, or to the surface of the ligament, intranasally, for example, for treatment of the nasal duct or the tracheal duct, or orally, for example using a capsule, to lubricate the gastrointestinal tract.

In an embodiment of the present invention, the lubricating fluid is used for the treatment of osteoarthritis by intra-articular injection. Thus, there is provided a synthetic synovial fluid comprising (or consisting of) the above lubricating fluid. In embodiments, the synthetic synovial fluid also comprises one or more pharmaceutically acceptable additive and/or therapeutic agent as defined above.

In a further embodiment of the present invention, the lubricating fluid is used in the treatment of dry eye syndrome. Topical application of this fluid to the cornea is expected to allow for better retention of water on the surface of the eye and to reduce the adhesion between the eyelid and ocular epithelium (said adhesion being a source of pain), which commercial formulations currently cannot do. Thus, there are provided eyes drops comprising (or consisting of) the above lubricating fluid. In embodiments, the eyes drops also comprise one or more pharmaceutically acceptable additive and/or therapeutic agent as defined above.

In a yet another embodiment of the present invention, the lubricating fluid is used in the treatment of vaginal dryness and/or also infertility related to vaginal dryness. The fluid, for example in gel form, would be topically applied to the vaginal mucosa. It should allow the restoration of lubrication and consolidate mucus, thereby providing relief and possibly facilitating the transport of male gametes as well. Thus, there is provided a vaginal lubricating composition comprising (or consisting of) the above lubricating fluid. In embodiments, the composition also comprises one or more pharmaceutically acceptable additive and/or therapeutic agent as defined above.

The present invention also provides the use of the above lubricating fluid in lubricating a medical instrument. There is also provided a method of lubricating a surface of medical instrument comprising the step of contacting the lubricating fluid with said surface. In embodiments, the medical instrument may be a syringe (for example the barrel may be the surface to lubricate), an injection device, or an elution device. In such embodiments, the lubricating fluid preferably consists of pharmaceutically acceptable ingredients (i.e. polymers, solvents, additives, etc.) only.

According the results shown in the Examples below, after application, the fluid protects surfaces against wear without requiring any chemical modifications of the surfaces it protects. This is quite advantageous in the case of biological tissues, as wear may cause pain. Currently existing formulations of hyaluronic acid, such as injections of hyaluronic acid (linear or crosslinked) have no demonstrated anti-wear effect. However, in the fluid of the invention, the combination of the bottle-brush polymer, which has a lubricating effect, with a linear polymer that confers anti-wear protection results in a synergistic protective effect that is greater than that which would be obtained by merely summing the effects of the compounds taken separately.

In fact, the prior art fails to disclose lubricating fluids with both strong lubricating qualities and anti-wear effects.

Mixture of Polymers

There is also provided a mixture comprising:
a) a bottle-brush polymer comprising a polymeric backbone with polymeric pendant chains, and
b) a linear polymer,
wherein the bottle-brush polymer and the linear polymer are as defined above.

In embodiments, the mixture is in solid form, for example in the form of a powder.

The mixture may be used to produce the above lubricating fluid. This method for producing the lubricating fluid comprises contacting the mixture with a solvent and allowing dissolution of the mixture in the solvent.

This method allows producing a required amount of the lubricating fluid according to demand for example at the location where it is used.

Optionally, the method further comprises mixing the mixture with the solvent to speed the dissolution of the linear polymer and the bottle-brush polymer.

The lubricating fluid may be produced in vitro or in vivo. In vitro production entails that the contacting, and optional mixing step, carried out thereby before the lubricating fluid is used (e.g. for any of its above uses).

In vivo production entails, before said contacting step, the administration of the mixture to a subject. Then, the dissolution occurs in vivo. In such embodiments, the lubricating fluid preferably consists of pharmaceutically acceptable ingredients (i.e. polymers, solvents, additives, etc.) only, i.e. the lubricating fluid is pharmaceutically acceptable. In preferred embodiments, the mixture and the liquid are contacted at the desired site of action of the lubricating fluid. The solvent may be a body fluid or an extraneous solvent (i.e. a solvent originating outside the subject, i.e. not a body fluid of the subject), such as those mentioned in the previous sections. In a particular embodiment, the mixture is administered orally in the form of an oral formulation that will release the linear polymer and the bottle-brush polymer in the gastrointestinal tract. This allows the linear polymer and the bottle-brush polymer to contact and dissolve in a fluid of the gastrointestinal tract (which will thereby act as a solvent), thereby producing the lubricating fluid in situ.

In embodiments, the mixture comprises the bottle-brush polymer and the linear polymer present in a bottle-brush polymer:linear polymer weight ratio between about 1:1 and about 1:20, preferably between about 1:2.5 and about 1:15, more preferably between about 1:5 and about 1:10.

Surface Bearing a Polymeric Layer

There is also provided a surface bearing a polymeric layer comprising:
a) a acceptable bottle-brush polymer comprising a polymeric backbone with polymeric pendant chains, and
b) a acceptable linear polymer,
wherein the bottle-brush polymer and the linear polymer are as defined above.

In embodiments, the bottle-brush polymer and the linear polymer are pharmaceutically acceptable.

The surface may be for example a glass surface, a plastic surface, a metal surface, etc.

Examples of surfaces that can bear the polymeric layer include a surface of an ophthalmic lens, for example a contact lens, including either or both sides of the lens. Other examples include a surface of an implant, such a joint replacement implant, including hip and knee replacement implants. Yet other examples of surface include a the barrel of a syringe, a surface of an injection device, and a surface of an elution device.

The polymeric layer can be manufactured on the surface by methods well known to the skilled person.

In embodiments, the polymeric layer can release the bottle-brush polymer and linear polymer, for example at a desired site of action, when in contact with a liquid, for example a biological liquid, so as to have a lubricating effect. In such embodiments, the polymeric layer is manufactured so that the bottle-brush polymer and linear polymer can detach from the surface at a desired rate. As an example, a solution of the polymers (e.g. for example the above lubricating fluid) could be solvent-casted on the surface.

In other embodiments, the bottle-brush polymer and linear polymer are meant to remain on the surface for a period of time when in contact with a liquid, for example a biological fluid. Since the surface bear both the bottle-brush polymer and linear polymer, it can impart a desired lubricating effect, for example, at a desired site of action. In such embodiments, the polymeric layer is manufactured so the polymers will not detach from the surface or will become detached at a slow rate (including a very slow rate due to unavoidable wear and tear). As an example, the polymers could be chemically grafted on the surface.

In embodiments, the polymeric layer comprises the bottle-brush polymer and the linear polymer present in a bottle-brush polymer:linear polymer weight ratio between about 1:1 and about 1:20, preferably between about 1:2.5 and about 1:15, more preferably between about 1:5 and about 1:10.

Porous Material with Embedded Polymers

There is also provided a porous material having embedded therein:
a) a bottle-brush polymer comprising a polymeric backbone with polymeric pendant chains, and
b) a linear polymer,
wherein the bottle-brush polymer and the linear polymer are as defined above.

The porous material may be any porous material. Examples of porous materials include:
gels, including crosslinked gels (An example of a gel is a hydrogel. An example of a hydrogel porous material is a contact lens);
sponges; and
textiles and textile fibers, including woven and nonwoven. Examples of textiles and textile fibers those used in diapers, facial tissues and dental floss.

Herein "embedded" means that the bottle-brush polymer and linear polymer are contained within the pores and crevices of the porous material.

When the bottle-brush polymer and linear polymer are embedded in a porous material, they are released when the material contacts is used in contact with a solvent for the polymer. Indeed, in use, the material can be subjected to mechanical constraint, which will release the polymers and allow them to provide the desired lubricating effect.

In embodiments, the bottle-brush polymer, the linear polymer, and the porous material are pharmaceutically acceptable.

In embodiments, the porous material comprises the bottle-brush polymer and the linear polymer present in a bottlebrush polymer:linear polymer weight ratio between about 1:1 and about 1:20, preferably between about 1:2.5 and about 1:15, more preferably between about 1:5 and about 1:10.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Herein, the term "pharmaceutically acceptable salt" refers to salts that are pharmacologically acceptable and substantially non-toxic to the subject to which they are administered. More specifically, these salts retain the biological effectiveness and properties of the compounds of the invention and are formed from suitable non-toxic organic or inorganic acids or bases. The salts of the invention include base salts formed with an inorganic or organic base. Such salts include alkali metal salts such as sodium, lithium, and potassium salts; alkaline earth metal salts such as calcium and magnesium salts; metal salts such as aluminium salts, iron salts, zinc salts, copper salts, nickel salts and a cobalt salts; inorganic amine salts such as ammonium or substituted ammonium salts, such as e.g. trimethylammonium salts; and salts with organic bases (for example, organic amines) such as chloroprocaine salts, dibenzylamine salts, dicyclohexylamine salts, dicyclohexylamines, diethanolamine salts, ethylamine salts (including diethylamine salts and triethylamine salts), ethylenediamine salts, glucosamine salts, guanidine salts, methylamine salts (including dimethylamine salts and trimethylamine salts), morpholine salts, morpholine salts, N,N'-dibenzylethylenediamine salts, N-benzyl-phenethylamine salts, N-methylglucamine salts, phenylglycine alkyl ester salts, piperazine salts, piperidine salts, procaine salts, t-butyl amines salts, tetramethylanmonium salts, t-octylamine salts, tris-(2-hydroxyethyl)amine salts, and tris(hydroxymethyl)aminomethane salts.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1

What follows is a brief description of the procedure used to manufacture and test an embodiment of the present invention. In the following procedure, the term "polymer solution" refers to a solution containing the bottle-brush polymer.

Figure 38:
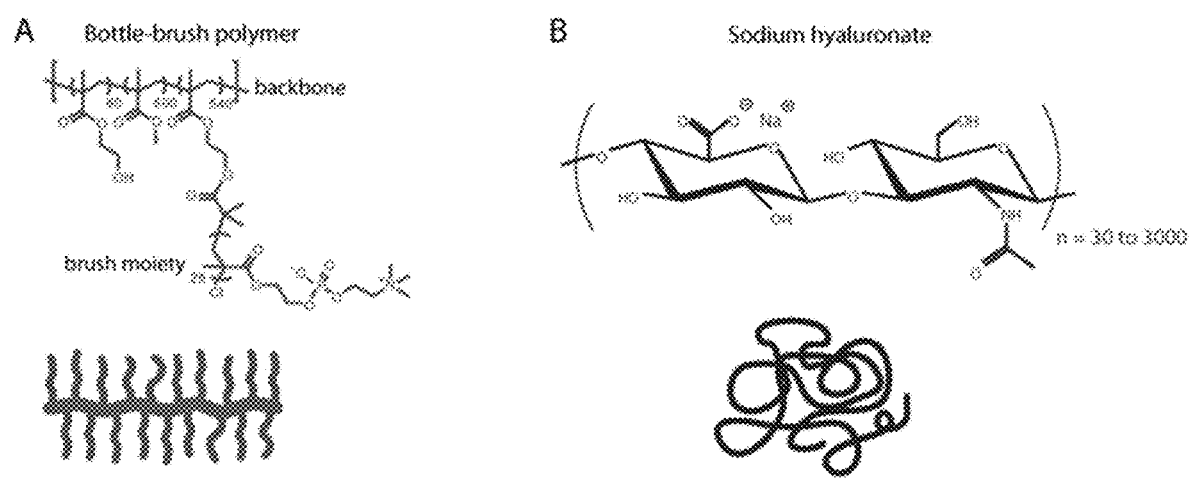
FIG. 38 shows the chemical structures of an exemplary bottle-brush polymer and sodium hyaluronate.

In this example, the design of lubricating and wear protecting fluids based on mixtures of bottle-brushes (BB) and linear polymer solutions are described. FIG. 38 depicts the chemical structures of an exemplary bottle-brush polymer and sodium hyaluronate. To illustrate this concept, hyaluronic acid (HA), a naturally occurring linear polyelectrolyte, and a water-soluble synthetic BB polymer were used. Individually, these two polymers exhibit poor wear protecting capabilities compared to that of saline solutions. Mixture of the two polymers in pure water or in saline allows the wear protection of surfaces over a wide range of shearing conditions to drastically increase. We demonstrate that this synergy between the BB and HA polymers emerges from a strong cohesion between the two components forming the boundary film due to entanglements between both polymers. The example also show that this concept can be applied to other types of linear polymers and surfaces and is independent of the chemical and mechanical properties of the surfaces.

Here, we show that it is possible to design lubricating fluids able to provide excellent wear protection without any chemical modification of the surfaces. The fluids use two components, BB polymers containing zwitterionic pendant chains synthesized by atom transfer radical polymerization, ATRP, and a natural linear polymer, sodium hyaluronate (HA). Both components are soluble in pure water or saline conditions.

A surface forces apparatus (SFA) was used to characterize the wear protection capacity and the lubricating properties of the various fluids tested. The SFA allows measuring frictional forces under a wide range of pressure and sliding speeds while monitoring the separation distance between the surfaces at ±0.5 Å resolution as well as the shape of the contact. Muscovite mica is the substrate of choice in SFA experiments mostly because of its optical transparency and atomic flatness. Herein, mica was also used due to its extreme propensity to suffer damage under moderate shear conditions in water and saline conditions.

Materials and Methods

Materials

Methyl methacrylate (MMA, purity=99%, Sigma-Aldrich, USA) and 2-(trimethylsilyloxy)ethyl methacrylate (HEMA-TMS, purity >9%, Scientific Polymer Products Inc., USA) were passed through a column filled with basic alumina prior to use. 2-Methacryloyloxyethyl phosphorylcholine (MPC, purity ≥97%, Sigma-Aldrich, USA) was recrystallized from acetonitrile and dried under vacuum overnight at room temperature before polymerization. Tetrahydrofuran (THF) was used after it was purified by tapping off from a solvent purification column right. Ethyl α-bromoisobutyrate (EiBr, purity ≥98%, Sigma-Aldrich, USA), copper(I) chloride (CuICl, purity ≥99.995% trace metals basis, Sigma-Aldrich, USA), copper(II) chloride (CuIICl2, purity ≥99.995% trace metals basis, anhydrous, Sigma-Aldrich, USA), 2,2'-bipyridyl (bpy, purity ≥99%, Sigma-Aldrich, USA), 4,4'-Dinonyl-2,2'-dipyridyl (dNbpy, purity ≥97%, Sigma-Aldrich, USA), potassium fluoride (KF, purity ≥99%, spray-dried, Sigma-Aldrich, USA), tetrabutylammonium fluoride (TBAF, IM solution in THF, Sigma-Aldrich, USA) and α-bromoisobutyryl bromide (purity=98%, Sigma-Aldrich, USA were used without any additional purification. Solvents were purchased from Aldrich and used as received without further purification.

Ruby mica-sheets were purchased from S&J Trading Inc. (Glen Oaks, N.Y., USA). Milli-Q quality water was obtained from a Millipore Gradient A10 S10 purification system (resistance=18.2 MΩ·cm, TOC≤4 ppb). Phosphate buffer saline (10 mM Phosphate, 150 mM NaCl and pH 7.4) was prepared in the inventors' laboratory. Hyaluronic acids of different molecular weights were obtained from lifecore biomedical (Minneapolis, USA).

Equipment and Analysis

Proton nuclear magnetic resonance ($^1$H NMR) spectroscopy was performed using Bruker 300 MHz spectrometer. In all cases deuterated chloroform (CDCl$_3$) was used as a solvent, except for the bottle-brush polymer which was analyzed using deuterated methanol (CD$_3$OD). $^1$H chemical shifts are reported in parts per million (ppm) downfield from tetramethylsilane (TMS).

Apparent molecular weight and molecular weight distribution measurements of polymers, except those of the bottle-brush polymer, were measured by size exclusion chromatography (SEC) using Polymer Standards Services (PSS) columns (guard, 105, 103, and 102 Å), with THF or DMF as an eluent at 35° C. at a constant flow rate of 1.00 mL/min, and a differential refractive index (RI) detector (Waters). The apparent number-average molecular weights (Mn) and molecular weight distribution (Mw/Mn) were determined with a calibration based on linear poly(methyl methacrylate) (PMMA) standards and diphenyl ether as an internal standard. Absolute molecular weights were determined using ASTRA software from Wyatt Technology by GPC-MALLS containing RI detector (Wyatt Technology, Optilab rEX), viscometer detector (Wyatt Technology, ViscoStar), and a multi-angle laser light scattering (MALLS) detector (Wyatt Technology, DAWN EOS) with the light wavelength at 690 nm.

Hyaluronic acid apparent molecular weight and dispersity were assessed by aqueous SEC in 10 mM PBS, pH 7.4, 150 mM NaCl buffer using TSKgel columns (TSKgel G6000PW, particle size 12 μm, and TSKgel G2500PW, particle size 12 μm, Tosoh Biosciences LLC) at a constant flow rate of 0.5 mL/min, and Multi-Angle static Light Scattering (DAWN HELEOS, Wyatt), and Refractometer (Optilab T-rEX, Wyatt). The absolute number-averaged molecular weights ($M_n$) and molecular weight dispersity (M/M) were determined with a dn/dc set at 0.16 mL/mg. The results are shown in the following table.

|  | $M_w$ [g/mol] | Dispersity | $R_g$ [nm]$^a$ 10 mM$^b$ | 150 mM |
|---|---|---|---|---|
| 10 kDa HA | 1.16 × 10$^4$ | 1.26 | — | 16 ± 2 |
| 60 kDa HA | 5.97 × 10$^4$ | 1.43 | — | 33 ± 1 |
| 300 kDa HA | 3.25 × 10$^5$ | 1.54 | 71 | 69 ± 4 |
| 1.5 MDa HA | 1.32 × 10$^6$ | 1.44 | 220 | 154 ± 12 |

$^a$Measured by static light scattering
$^b$from ref.[1,2]

Absolute molecular weights were determined using ASTRA software from Wyatt Technology by GPC-MALLS containing RI detector (Wyatt Technology, Optilab rEX), viscometer detector (Wyatt Technology, ViscoStar), quasi-elastic-light-scattering detector (Wyatt Technology, QELS+) and a multi-angle laser light scattering (MALLS) detector (Wyatt Technology, HELEOS) with the light wavelength at 690 nm.

AFM imaging was performed in air using a MFP3D microscope from Azylum Research (Santa Barbara USA). Standard silicon nitride tips were used to image the polymer deposited on a mica substrate from an aqueous solution. After drying, the polymer film was introduced in the microscope and imaging was performed at a scanning speed of 1 Hz with a typical image size of 5×5 microns.

Bottle-Brush Polymer (PMPC B2) Synthesis

A molecular bottlebrush with a grafting ratio of about 50% of hydrophilic (phosphorylcholine-, PMPC B2) grafts was prepared via 'grafting from' approach.

Figure 2:
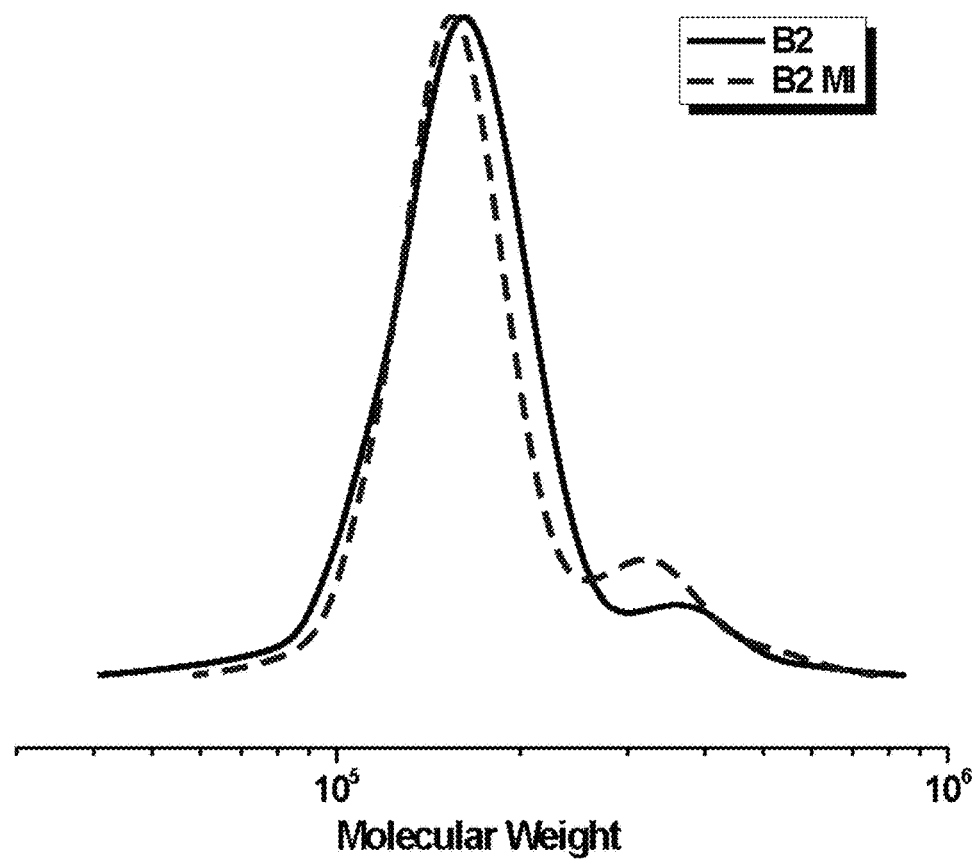
FIG. 2 shows GPC traces recorded for B2 (solid line) and B2 MI (dashed line).

The backbone for the brush was synthesized through equimolar copolymerization of HEMA-TMS and MMA, resulting in the polymer (HEMA-MS)$_{600}$-stat-MMA$_{600}$ (B2) with DP~1200. GPC characterization of B2 showed the signal with M=132,000 and low dispersity: $M_w/M_n$=1.16 (FIG. 2, solid line).

The subsequent functionalization of B2 with atom transfer radical polymerization (ATRPP) initiating functionalities yielded the macroinitiator (B2 MI) with $M_n$=163,000 and low dispersity: $M_w/M_n$=0.5 (FIG. 2, dashed line). $^1$H NMR analysis of B2 MI was used to determine the ratio of MMA and HEMA (functionalized or not) incorporated into the polymer (FIG. 3), proving incorporation of 50 mol % of HEMA (functionalized with TMS or not) into the backbone. In addition, the spectra showed incomplete functionalization of HEMA resulting in 40 mol % of ATRP initiator sites in B2 MI.

Figure 4:
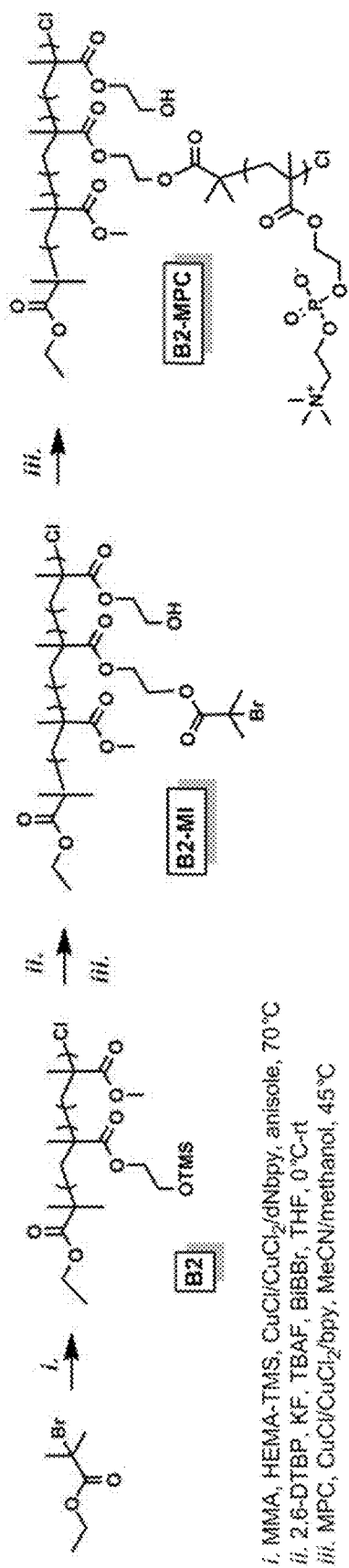
FIG. 4 shows synthetic pathways for the preparation of ABA bottle-brush copolymers with PMPC (PMPC B2) pendant chains.

B2 MI was later used to graft hydrophilic pendant chains via ATRP, as shown in FIG. 4. The grafting of hydrophilic PMPC pendant chains (PMPC B2) was performed in methanol/acetonitrile mixture (70/30, v.v. %) at 45° C., obtaining a PMPC B2 brush with the composition of (PBiBEM$_{540}$-g-PMPC$_{28}$)-stat-PHEMA$_{60}$-stat-PMMA$_{600}$.

The three-step synthesis scheme is shown in FIG. 4.

Synthesis of P(HEMA-TMS)$_{600}$-stat-MMA$_{600}$ (B2)

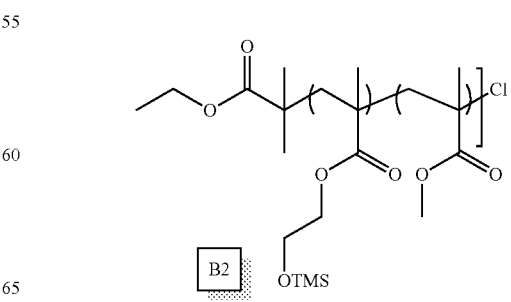

First, the backbone for the brush, P(HEMA-TMS)$_{600}$-stat-MMA$_{600}$, which is a statistic copolymer of methyl methacrylate and 2-(trimethylsiyloxy)ethyl methacrylate, was synthesized as follows.

A dry 25 mL Schlenk flask was charged with ethyl α-bromoisobutyrate (EbiB) (5.8 mg, 4.4 µL 0.030 mmol), Cu$^{II}$Cl$_2$ (3.1 mg, 0.023 mmol), dNbpy (0.113 g, 0.276 mmol), HEMA-TMS (9.28 g, 10.0 mL, 45.9 mmol), MMA (4.59 g, 4.9 mL, 45.9 mmol) and anisole (3.2 mL). The solution was degassed by three freeze-pump-thaw cycles. During the final cycle, the flask was filled with nitrogen and Cu$^{I}$Cl (11.4 mg, 0.115 mmol) was quickly added to the frozen reaction mixture. The flask was sealed, evacuated and back-filled with nitrogen five times, and then immersed in an oil bath at 70° C. Reaction was stopped after 67 h via exposure to air, reaching the degree of polymerization 1200 for the final polymer. The monomer consumption was calculated by the integration of the MMA and HEMA-TMS vinyl groups' signal (CHH=C—CH$_3$, 6.11 ppm or 5.56 ppm) against the internal standard (anisole, op-Ar—H, 6.91 ppm). The product was purified by three precipitations from hexanes, dried under vacuum for 16 h at room temperature, and analyzed by $^1$H NMR spectroscopy. The ratio of PMMA (s, broad, CO—O—CH$_3$, 3.54-3.68 ppm) to P(HEMA-TMS) (s, broad, OCO—CH$_2$, 3.90-4.17 ppm) peaks resulted in the polymer composition: P(HEMA-TMS)$_{600}$-co-PMMA$_{600}$. Apparent molecular weights were determined using THF GPC: $M_n$=132,000 and $M_w/M_n$=1.16 (solid line, FIG. 2).

Synthesis of PBiBEM$_{540}$-stat-PHEMA$_{60}$-stat-PMMA$_{600}$ (B2 MI)

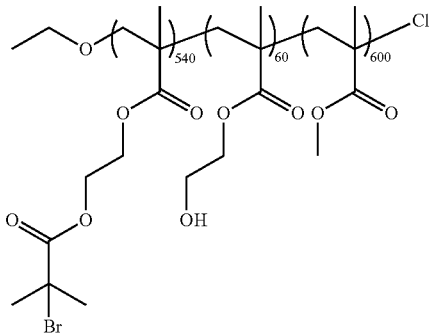

In the second step, the HEMA-TMS repeat units of brush backbone (B2) were functionalized. The result was a statistic copolymer of methyl methacrylate and 2-bromoisobutyryloxyethyl methacrylate with only some non-functionalized hydroxyethyl methacrylate (HEMA) repeat units remaining: PRiBEM$_{540}$-stat-PHEMA$_{60}$-stat-PMMA$_{600}$.

The polymer, B2, (3.00 g, 0.017 mmol of polymer; 9.90 mmol of HEMA-TMS units), potassium fluoride (0.701 g, 11.9 mmol) and 2,6-di-tert-butylphenol (0.204 g, 0.99 mmol) were placed in a 100 ml round bottom flask. The flask was sealed, flushed with nitrogen, and then dry THF (30 mL) was added. The mixture was cooled in an ice bath to 0° C., tetrabutylammonium fluoride solution in THF (IM, 0.05 mL, 0.05 mmol) was injected into the flask, followed by the drop-wise addition of 2-bromoisobutyryl bromide (2.73 g, 1.50 mL, 11.9 mmol). After the addition the reaction mixture was allowed to reach room temperature and stirring was continued for 16 h. Next, triethylamine (1.0 mL) and another portion of α-bromoisobutyryl bromide (0.4 mL) were added, and the mixture was stirred for another hour. The solids were filtered off, and the solution was precipitated into methanol:water (70:30, v/v %). The precipitate was re-dissolved in chloroform and passed through a short column filled with basic alumina. The filtrate was re-precipitated three times from chloroform into hexanes and dried under vacuum overnight at room temperature.

Apparent molecular weights were determined using THF SEC: M=163,000 and $M_w/M_n$=1.15 (dashed line, FIG. 2).

Figure 3:
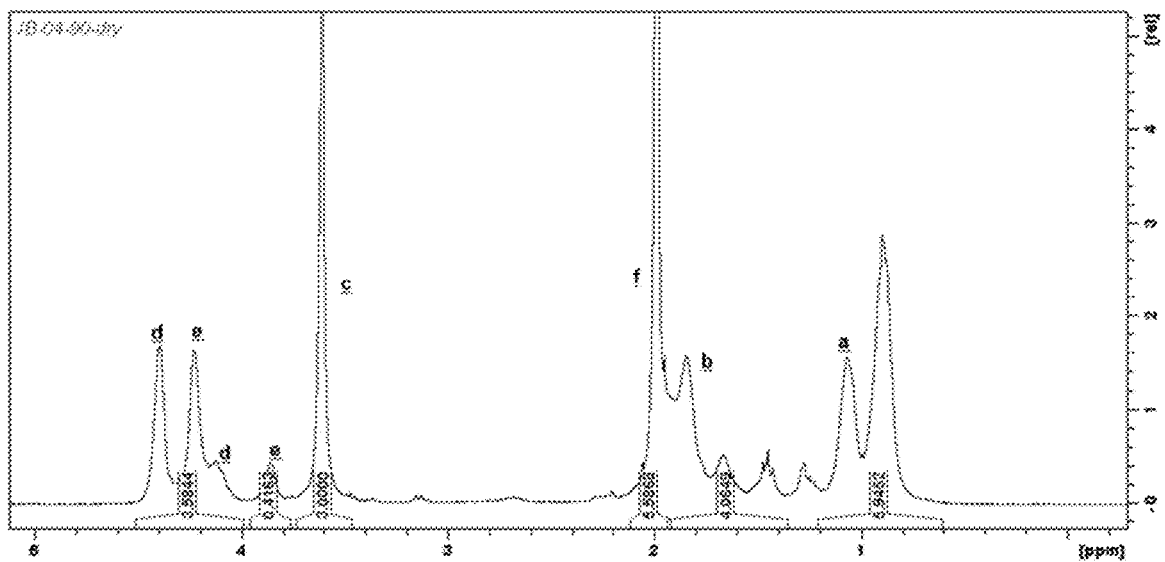
FIG. 3 shows the $^1$H NMR spectra of B2 MI.

The NMR spectrum of this polymer is shown in FIG. 3.

Synthesis of (PBiBEM$_{540}$-g-PMPC$_{28}$)-stat-PHEMA$_{60}$-stat-PMMA$_{600}$ ("PMPC B2" or "B2 PMPC")

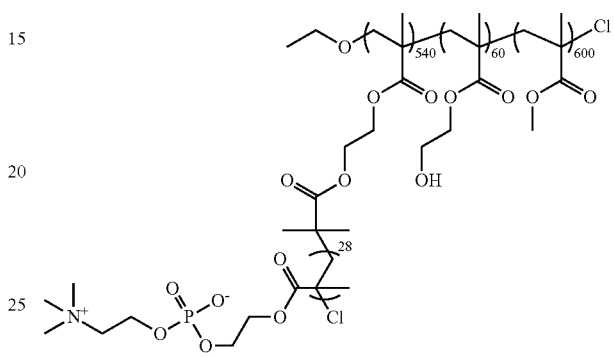

As a last step, 2-methacryloyloxyethyl phosphorylcholine was polymerized to form pendent chains grafted onto the functionalized repeat units of the backbone of the brush.

A dry 10 mL Schlenk flask was charged with polymer macroinitiator (B2 MI) (0.0059, 0.0124 mmol of BiBEM groups), 2-methacryloyloxyethyl phosphorylcholine (MPC) (1.10 g, 3.73 mmol), bpy (0.0066 g, 0.0422 mmol), Cu$^{II}$Cl$_2$ (0.33 mg, 2.5 µmol), and acetonitrile/methanol (1.0 mL/2.5 mL). The solution was degassed by three freeze-pump-thaw cycles. The flask was sealed, evacuated and back-filled with nitrogen and then immersed in an oil bath of 45° C. Then the degassed Cu$^{I}$Cl solution in methanol (18.4 mg, 18.6 µmol in 1.0 mL methanol) was added to the reaction mixture. The polymerization was stopped after 1 h 15 min. by exposing the solution to air, achieving the brush with DP~28 of PMPC pendant chains as determined by $^1$H NMR. The brush was purified by dialysis against methanol using a 25,000 MWCO membrane. The PMPC B2 brush was obtained as white powder.

Formulation of Lubricating Pharmaceutical Fluids 10.0 mg of different molecular weight hyaluronic acid (HA) (1.5 Mda, 500 kDa, 60 kDa and 10 kDa) were dissolved with magnetic stirring in 10 mL Milli-Q water or 10 mM PBS pH 7.4 in a glass vial. The solution was kept at 4° C. for 24 h prior to use. 1 mg/mL solution of PMPC B2 was prepared in the same buffers. 50 µL of the polymeric solution was added to 450 µL of HA solution resulting in a solution of PMPC B2 at 100 µg/mL and HA at 0.9 mg/mL and was homogenized with a vortex for 1 min. The solution was centrifuged at 14,000 rpm during 10 min to remove aggregates, particles or dust. For each SFA analysis, 50 µL of corresponding pharmaceutical fluid was injected between the surfaces. Surfaces were then let to equilibrate for 1 h prior to measurements.

Surface Forces Measurements

Normal Interaction Forces

Measurements of the normal interaction forces between two opposing surfaces as a function of the separation distance were carried out using a Surface Forces Apparatus (SFA 2000, SurForce LLC, USA). The normal interaction force $F^\perp$ is determined by measuring the deflection of the spring cantilever (spring constant of 482 N/m) supported by the lower surface. The distance between the surfaces is measured using Multiple Beam Interferometry (MBI). Fringes of Equal Chromatic Order (FECO) are generated using white light multiple beam interferometry shining white light through two back-silvered mica sheets glued onto glass cylinders (radius of curvature ~1.5 cm). FECO are analyzed in a spectrometer equipped with a CCD camera (Andor Zyla, Germany). The separation distance D between the surfaces is calculated (to ±1 Å) from the wavelength of the interference fringes. The two disks were mounted in the SFA chamber in cross cylinder geometry and brought into mica-mica adhesive contact in dry air in order to determine the reference position. Afterward, the cylindrical disks were separated by roughly 1 mm and lubricating pharmaceutical fluid was injected between the surfaces. Immediately after injection, the bottom of the SFA chamber was filled with water in order to saturate the surrounding vapors and to limit evaporation of the injected liquid. The normal interaction forces between the two polymer coated surfaces as a function of surface separation were determined on approaching (compression) and separating (decompression) the surfaces. For each test, all force runs (in and out) were performed at least in triplicate with the motor or the piezoelectric tube at a speed range of 0.4-1.6 nm/s. Each experiment was reproduced 2 to 6 times.

Figure 5:
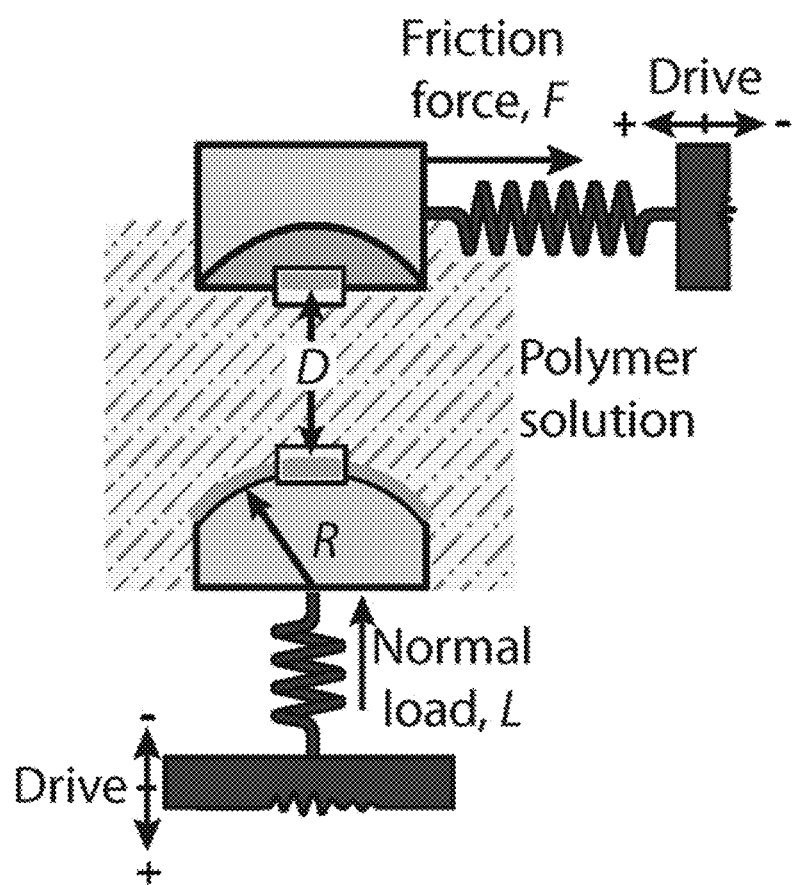
FIG. 5 shows the mechanical equivalent of the experimental surface force apparatus (FSA) setup in the configuration used in Example 1.

The FAS setup used is shown in FIG. 5.

Friction Force Measurements

The friction force $F_{II}$ was measured by moving the lower surface horizontally and measuring the response of the upper surface. Before measuring the friction forces, three cycles of normal compression/decompression were performed on the same contact position. For friction tests, a piezo bimorph drove the lower surface in a back and forth motion at a constant sliding frequency of 50 mHz controlled by a function generator. After sliding was finished, the load between the surfaces was slightly increased. The friction force transmitted to the upper surface was detected by semi conductive strain gauges, amplified by amplifiers and digitally recorded. Acquired data were processed using Origin Lab® software. The normal force was measured using calibrated strain gauges installed on the double cantilever spring supporting the lower surface. Separation distance and surface deformation were continuously recorded during the experiment using the FECO fringes analysis as described in the previous section. The pressure is assessed by dividing the normal force right before polymeric layer break and surface of contact measured by the flat area of contact fringes.

Speed Effect Measurement

The previously described setup is used to assess the speed effect. Surfaces are brought into contact and set at a constant load which is recorded throughout the experiment by strain gauges. Using the function generator, a piezo bimorph drove the lower surface in a back and forth motion. After sliding at one frequency was finished, the frequency was increased. The frequencies that were used in the experiments were 0.5 mHz, 1 mHz, 10 mHz and 50 mHz. The friction force was measured using calibrated strain gauges installed on the double cantilever spring supporting the lower surface.

Chitosan Gels and Tribotesting

A 2.5% w/w chitosan solution ($Mw=6.04\times10^5$, Mw/Mn=1.64, DA 4.3%) was prepared by dissolving the polymer in an aqueous acetic acid solution. Air bubbles were removed by centrifugation, and the highly viscous solution was compression-molded to obtain a slab of constant thickness. The chitosan solution was then placed in a 1 M NaOH coagulation bath to complete gelation. Gel disks of 11 and 21 mm in diameter were obtained using biopsy punchers and neutralized in pure water until use.

For the tribotesting experiments, the 11 mm diameter gel disk was glued on the top mobile part of a custom-made tribometer. The larger gel disk was glued on a metallic immobile bath filled with the tested polymer solution and left to incubate for 1 h prior to experimentation. Normal and tangential forces were recorded and analyzed with a home-made routine programmed in Labview. Roughness of the gels was quantified after performing tribotesting using an interferometric microscope.

Results

Characterisation of the Bottle Brush Polymer

Figure 6A:
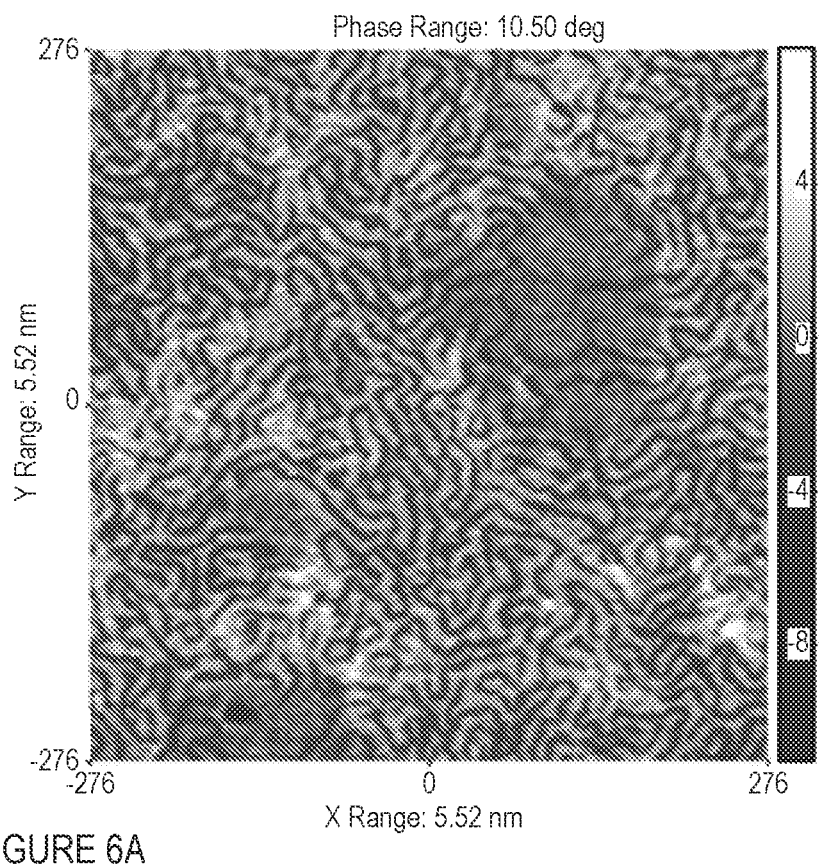
FIGS. 6 A) and B) are AFM pictures of the bottle brush polymer on mica in air.
Figure 6B:
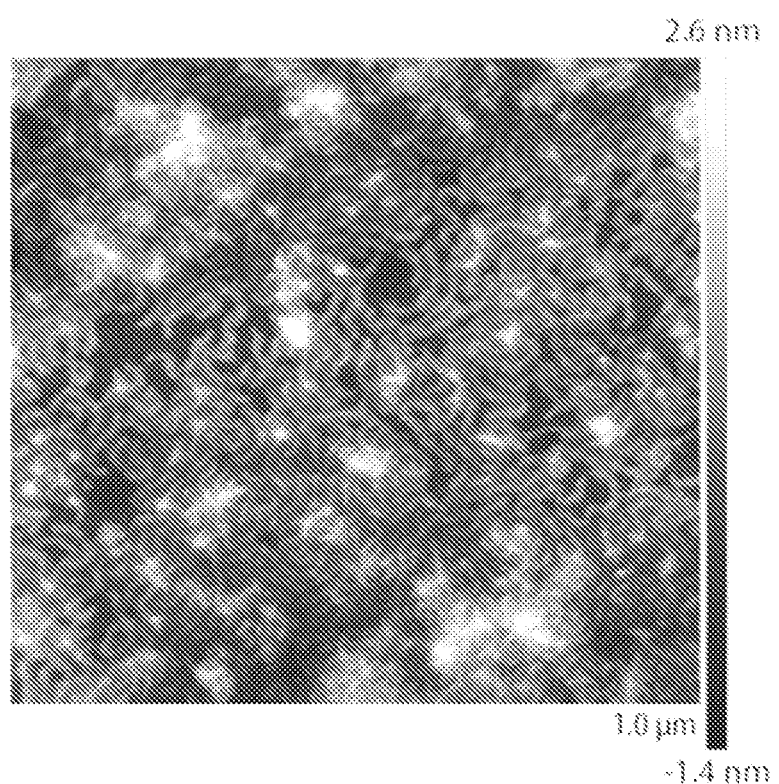

FIGS. 6 A) and B) shows AFM pictures of the bottle-brush polymer on mica in air. The AFM pictures show the bottle-brush polymer's worm-like structure, as expected for a bottle-brush polymer. FIG. 6 also shows that the polymer chains accommodate themselves to form a homogeneous film on the mica surface.

Figure 7:
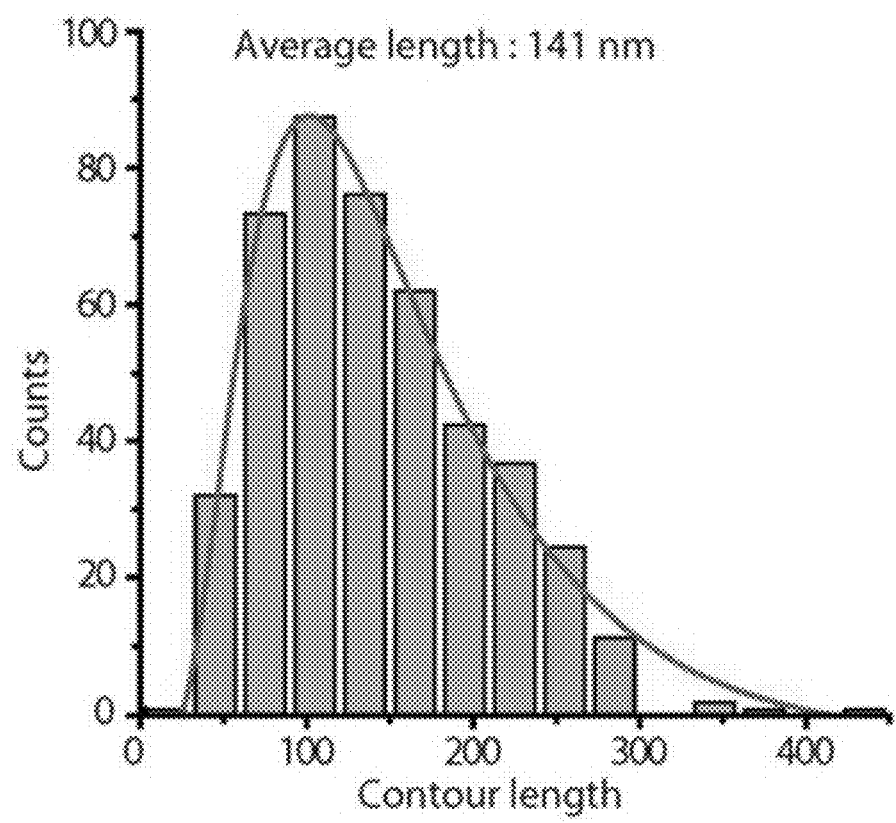
FIG. 7 shows the contour length of the bottle-brush polymer.

The contour length of the bottle-brush polymer is shown in FIG. 7.

In addition, the molecular weight of the backbone of the bottle-brush polymer was 88700 Da, while the molecular weight of the pendant chain was about 13275 Da.

Load Bearing Capacity of the Fluid

Load bearing capacity is the ability of a fluid film to sustain a normal stress without breaking. It can be assessed either by measuring the normal pressure required to bring two surfaces to atomic contact or by measuring the separation distance between the two surfaces at a given applied pressure. This property is critical to evaluating the ability of the fluid to protect the surfaces against impact damage and wear.

Figure 8:
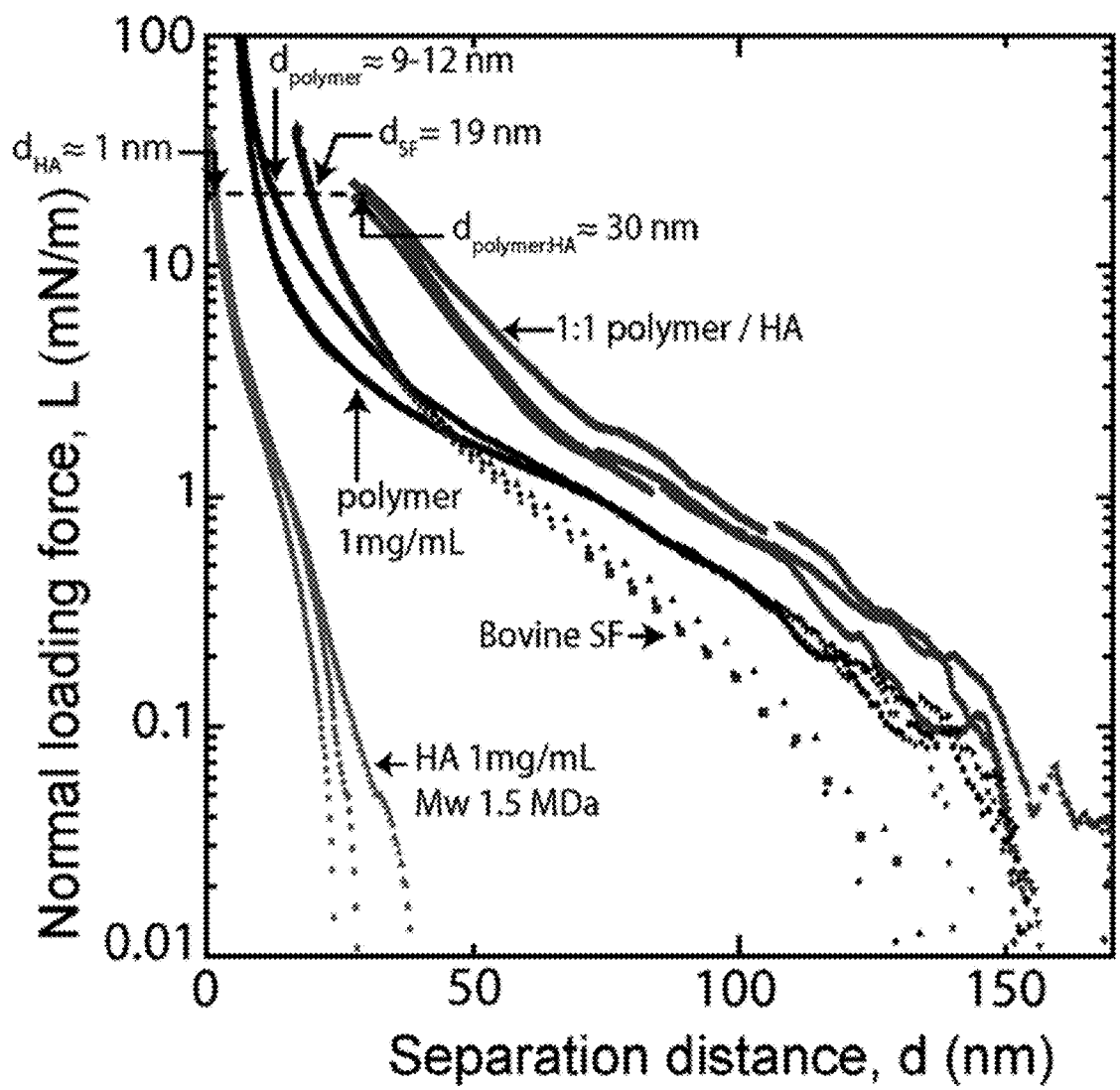
FIG. 8 shows the interaction force profiles across different fluids as measured in the SFA.

FIG. 8 shows the interaction forces measured in the SFA between two mica surfaces across synovial fluid (SF, bovine), HA solution (1 mg/mL), bottle-brush polymer solution (1 mg/mL) and a HA/bottle-brush polymer solution at a 1:1 ratio. The load bearing capacity of the confined film was assessed by measuring the separation distance between the surfaces at a normal force of 20 mN/m (corresponding to a normal pressure of approximately 1 Mpa). The results show that HA alone has a very poor load bearing capacity compared to SF ($d_{HA} \ll d_{SF}$). The bottle-brush polymer (noted as "polymer" in FIG. 8) exhibits a stronger load capacity than HA but fails to reach SF. The bottle-brush polymer: HA mixture demonstrates the highest load bearing capacity, far superior to the sum of the two components alone ($d_{bottle\text{-}brush\ polymer:HA} \gg d_{bottle\text{-}brush\ polymer} + d_{HA}$) confirming that a synergistic interaction between HA and the polymer allows the confined film to sustain much more pressure than SF itself.

We measured the normal interaction forces, F, between two facing mica surfaces of curvature, R, in the presence of the different components of the lubricating fluids, first individually and then mixed together. To cover a wide range of conditions, we tested different HA molecular weights, M, in pure water and in phosphate buffer saline (PBS, 150 mM for low ionic strength and 1500 mM NaCl for high ionic strength, both at pH 7.4). The interaction forces were recorded as a function of the separation distance, D, between the surfaces starting from several hundred nanometers (zero interaction regime) down to a few angstroms (strong interaction regime) in order to capture the full interaction force profile (force law) of the system.

Interaction forces measured in the SFA were obtained in presence of HA solutions in pure water and in salines. Each interaction force profile was measured at least three times on the same contact point and repeated over multiple contact points. Prior to the first measurement, and equilibration time of one hour was set for all tested conditions.

Figure 9:
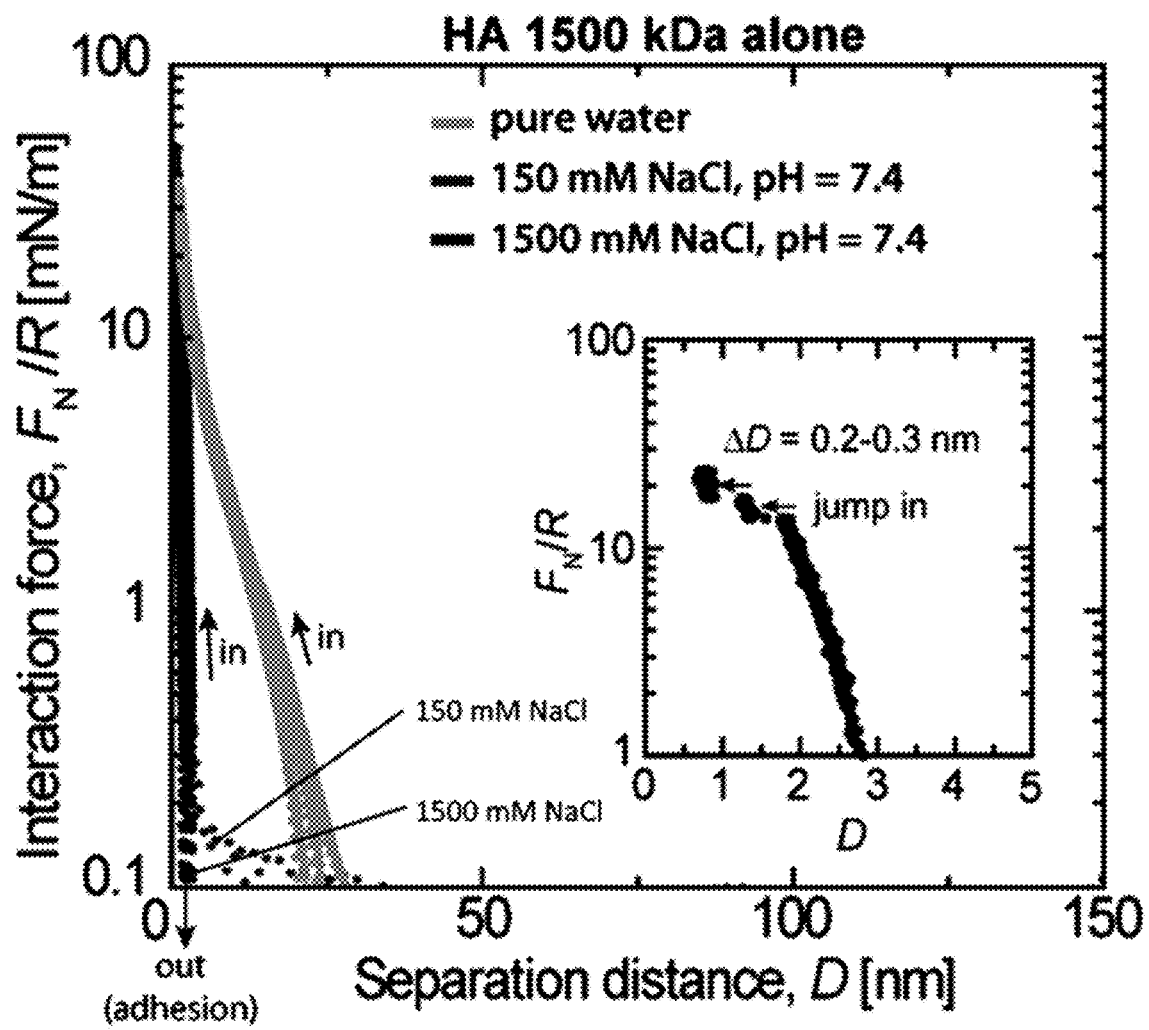
FIG. 9 shows the interaction force profiles measured for HA solution (1 mg/mL) at increasing ionic strength. Inset is an expanded view of the force profile at 1500 mM NaCl showing characteristic step-like instabilities in the interaction forces, indicating the presence of a layered structure in the confined space.
Figure 10:
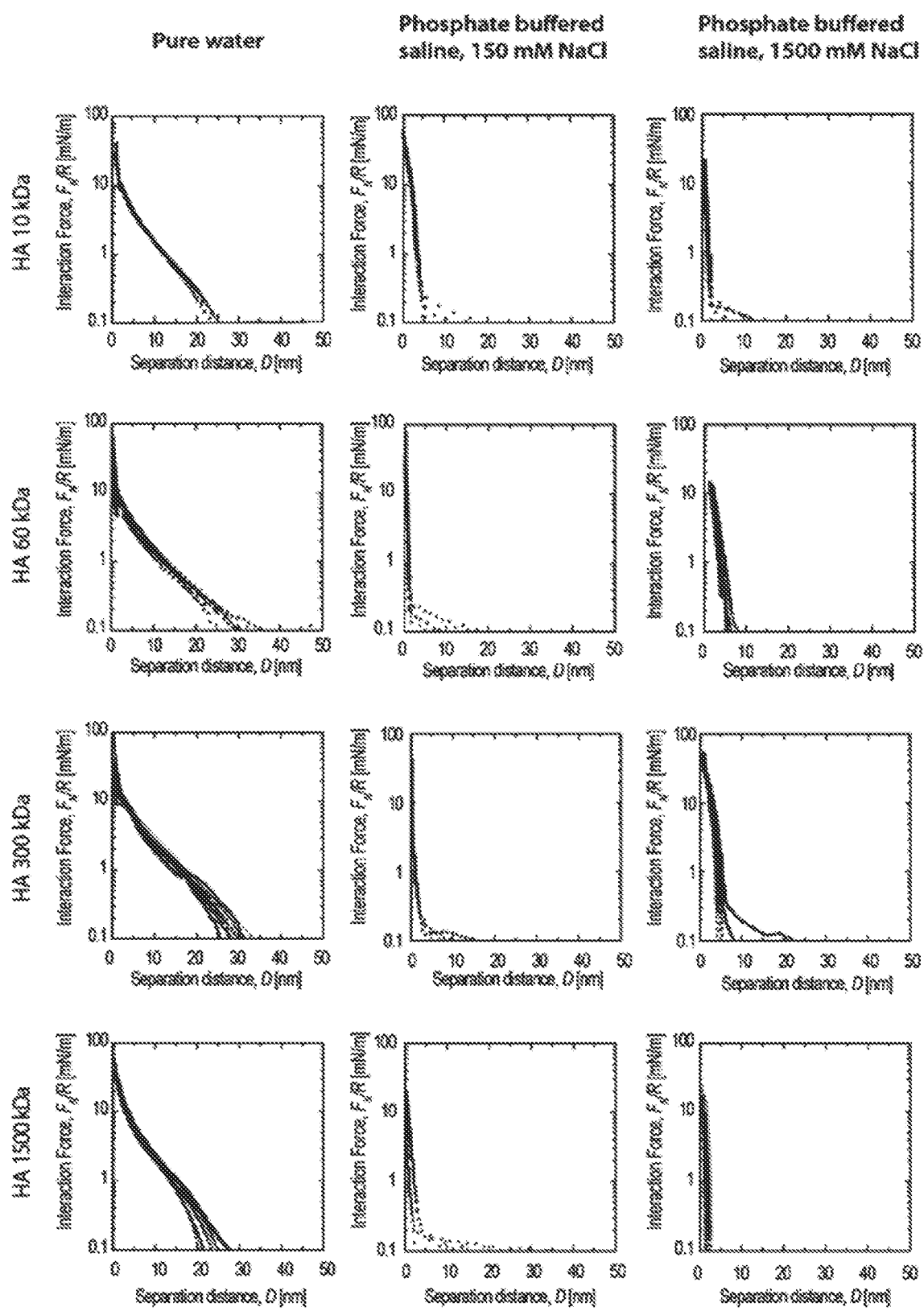
FIG. 10 shows the interaction forces measured in presence of HA (1 mg/mL) indifferent media. Out run (forces measured upon separation) are not represented for clarity but presented systematically weak adhesion.

FIGS. 9 and 10 shown the force profiles measured in HA solutions in pure water and in saline buffers. HA being negatively charged under all tested conditions; it is expected to adsorb as a random coil on negatively charged mica surfaces through the formation of hydrogen bonds.

As shown in FIG. 9, force profiles present two distinctive trends, depending on the ionic strength of the medium. In pure water, the onset of the interaction forces was located between 20 and 30 nm independently of the molecular weight of HA (see FIG. 10). Such weak dependence on the molecular weight suggests that, during the time window of the experiment, only low molecular weight chains could adsorb on the surfaces (a case similar to the Vroman effect). Low molecular weight molecules are expected to adsorb first on mica surfaces because they are more mobile. Later, larger molecules, which have higher affinity for the surface, are expected to displace them. In saline, the interaction forces exhibited shorter range forces starting between 5 and 10 nm. These short-range interaction forces systematically presented periodic instabilities, indicating the presence of a layered structure at the surfaces (see inset of FIG. 9). The characteristic size $\Delta D$ of these instabilities was $\Delta D=0.2-0.3$ nm, in agreement with the size of a water molecule. Adhesive forces were systematically measured upon separation of the surfaces independently of the medium (pure water or saline).

These observations demonstrate that, under the present experimental conditions, HA does not strongly bind to the mica surfaces in saline due to the presence of a 2-3 nm thick hydration layer strongly interacting with the surface, while in pure water, the polymer can adsorb strongly and form a stable soft layer.

Figure 11:
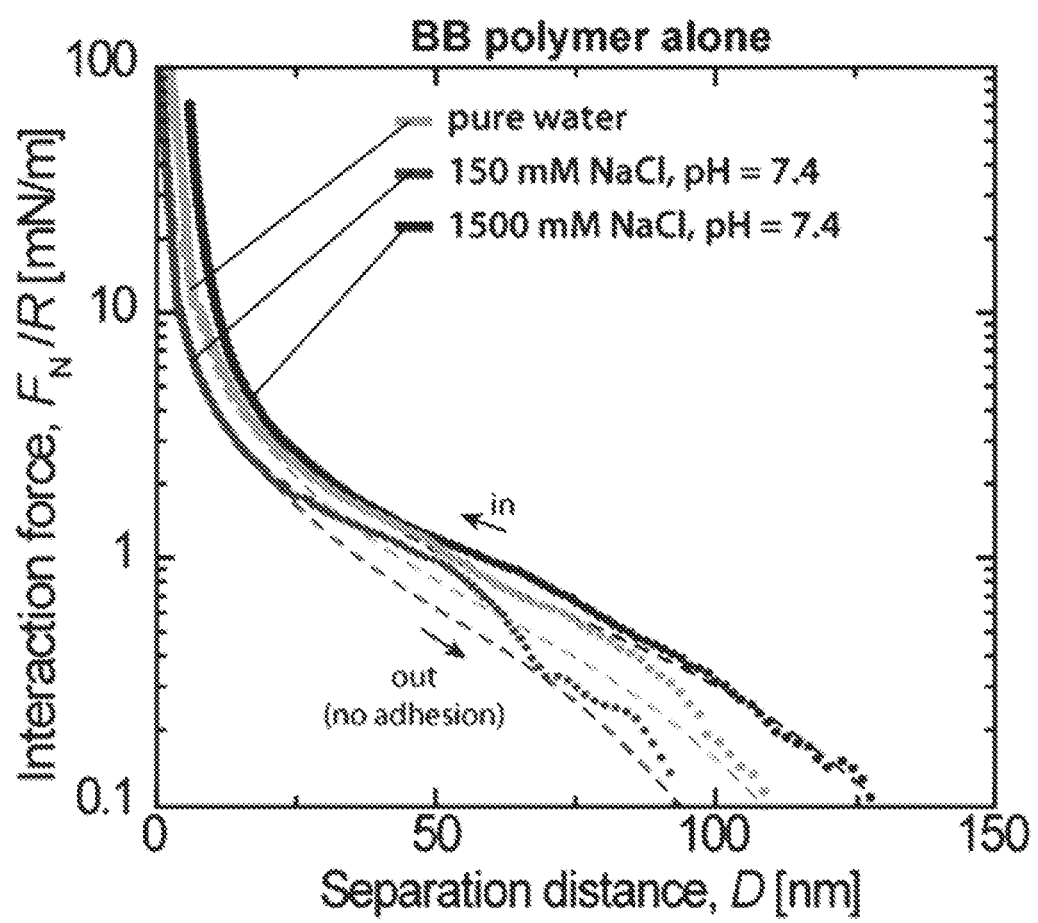
FIG. 11 shows the interaction force profiles measured for BB polymer solution (0.1 mg/mL) at increasing ionic strength.

Interaction forces in the presence of the BB polymer alone were strikingly different from those of the HA polymer alone (see FIG. 11). Repulsive forces were measured on approach and separation of the surfaces, independently of the ionic strength of the medium. More interestingly, the force profiles were insensitive to the ionic strength of the medium. Interestingly, the conformation of linear polymer chains of MPC has been reported to be insensitive to the ionic strength in solution[20] and at surfaces.[21] The onset of the interaction forces (determined at F/R=0.01 mN/n) was found to vary between 100 and 125 nm, independently of the medium ionic strength (FIG. 11). Given that the contour length of the polymer, assessed by AFM imaging in air (see FIG. 7), is ~140 nm, a significant part of the BB polymer is expected to be extending toward the medium.

Interaction forces under high confinement (D<10 nm) did not present any layering transition or any evidence of hydration forces, which confirms that the BB polymer interacts strongly with the hydrated surface layer, strongly enough to displace the water molecules present at the surface. Such observations echo some reports showing that charged amine head groups adjacent to H-bonding donor groups can efficiently remove bound water from a hydrated surface and facilitate H-bonding. No adhesive forces were measured upon separation of the surfaces.

Force profiles of the different polymer mixtures were also measured. Each HA:BB polymer mixture was tested in three different media as described in the manuscript. Force profiles were recorded on three different contact points to ensure good reproducibility.

Figure 12:
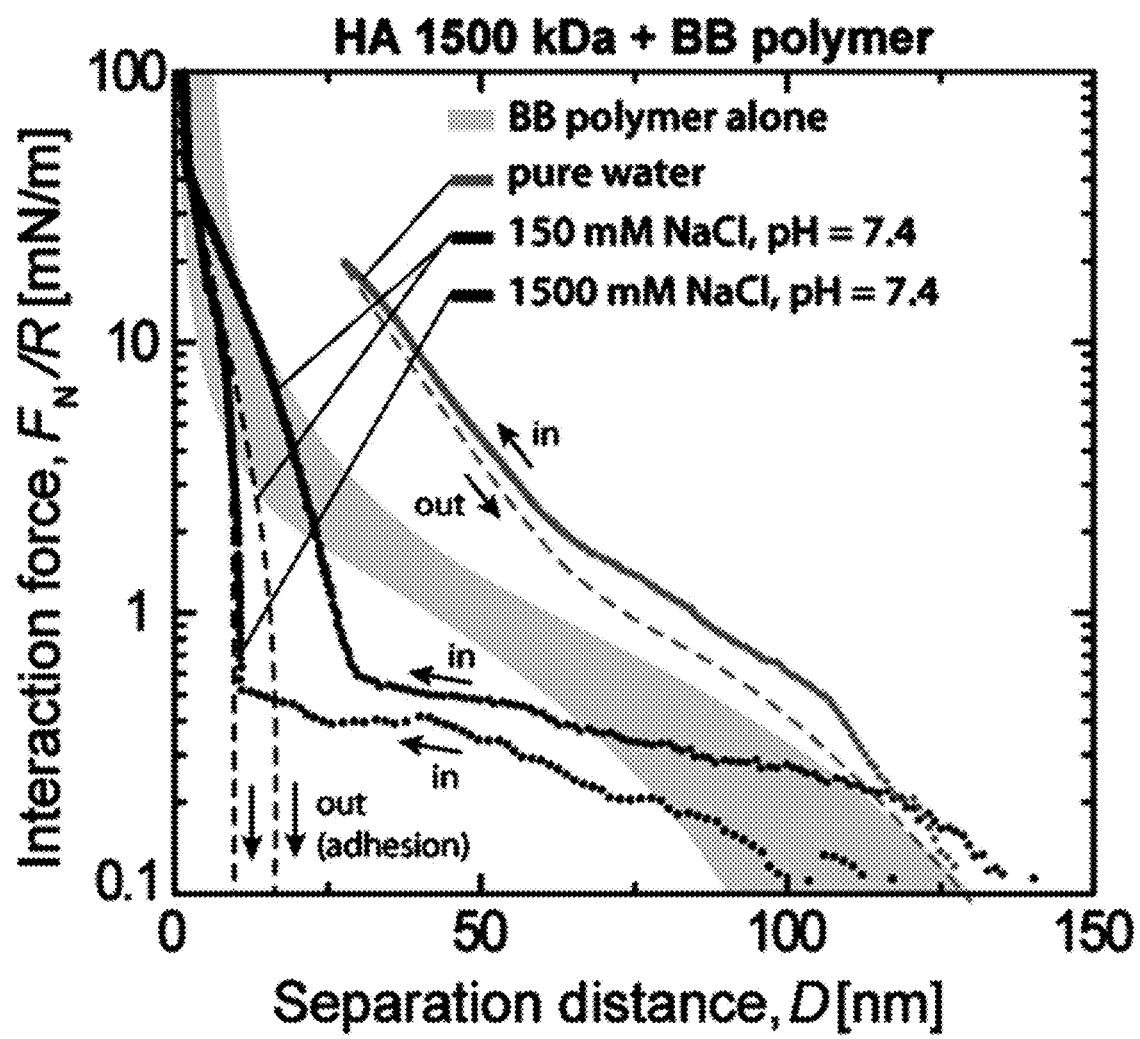
FIG. 12 shows the interaction force profiles measured for a mixture of BB polymer and HA 1500 kDa at different ionic strengths.
Figure 13:
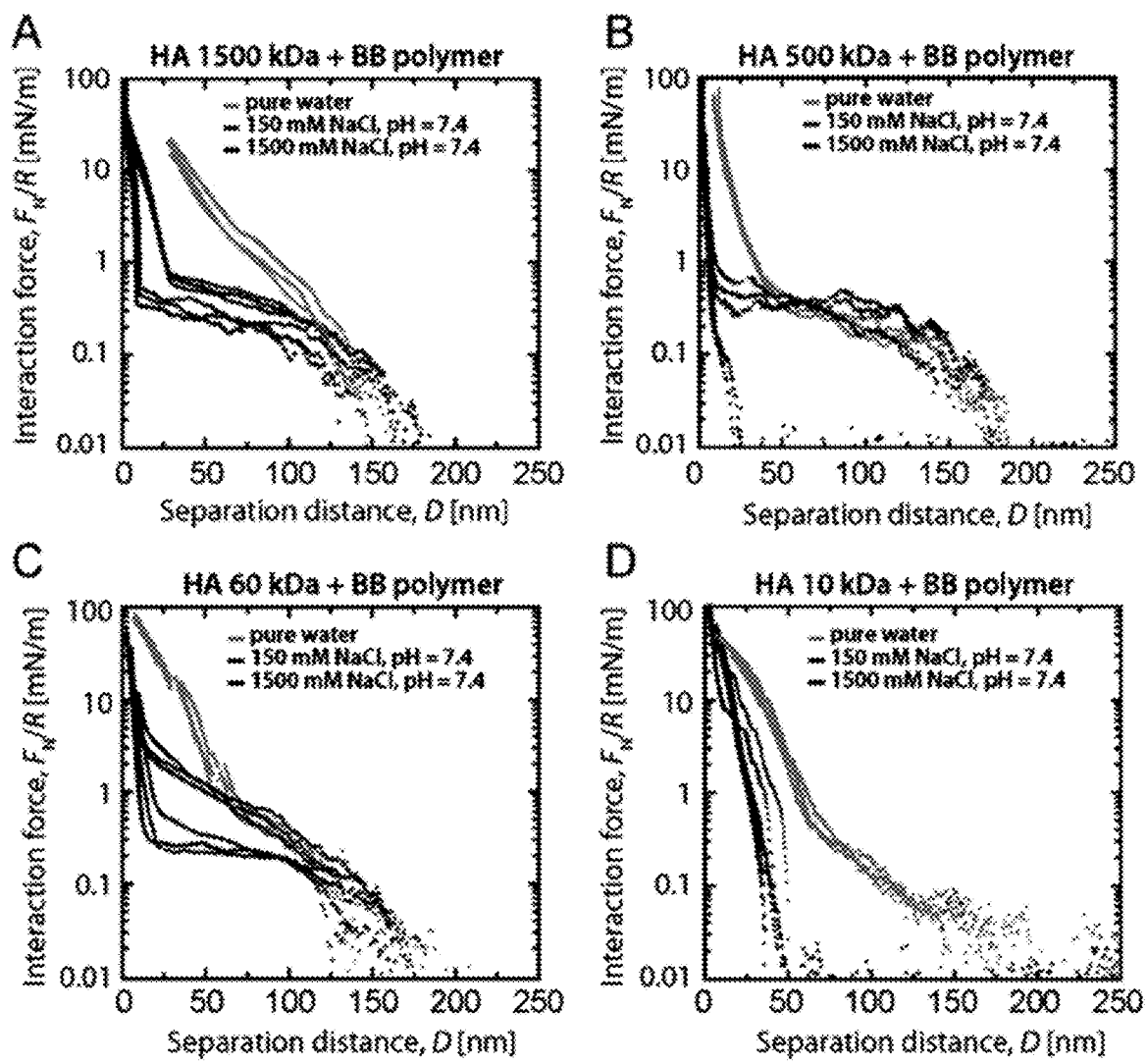
FIG. 13 shows the interaction forces between mica surfaces for mixtures of HA [A):1500 KDa, B) 500 kDa, C) 60 KDa, and D) 10 kDa] and BB polymer in pure water (top curves), in 150 mM NaCl (middle curves), and 1500 mM NaCl (top curves).

Interaction forces across HA-BB polymer mixtures in saline presented features similar to those of BB polymer alone (FIGS. 12 and 13). An exception was the mixture containing HA 10 kDa; the onset of the interaction forces measured for the different polymer mixtures ranged between 120 and 180 nm depending on the medium, which is similar to the onset measured with the BB polymer alone and at least twice the value measured for any of the tested HA alone solutions. Below a separation distance $D \approx 50$ nm, a steep increase in the interaction forces was systematically observed, suggesting the presence of a dense/stiff layer of polymer at the surfaces. The thickness of this dense (proximal) polymer layer was found to be highly sensitive to the ionic strength of the medium. Based on the force profiles, the thickness of the proximal layer can vary from approximately 20 nm at 150 mM NaCl to 5 nm at 1500 mM NaCl. No adhesive forces were measured if the surfaces were separated at D>50 nm (in the distal region of the interaction profile), and weak adhesive forces were systematically observed when separating the surfaces at D<50 nm. These observations confirmed that the proximal layer contains mainly HA.

Figure 14:
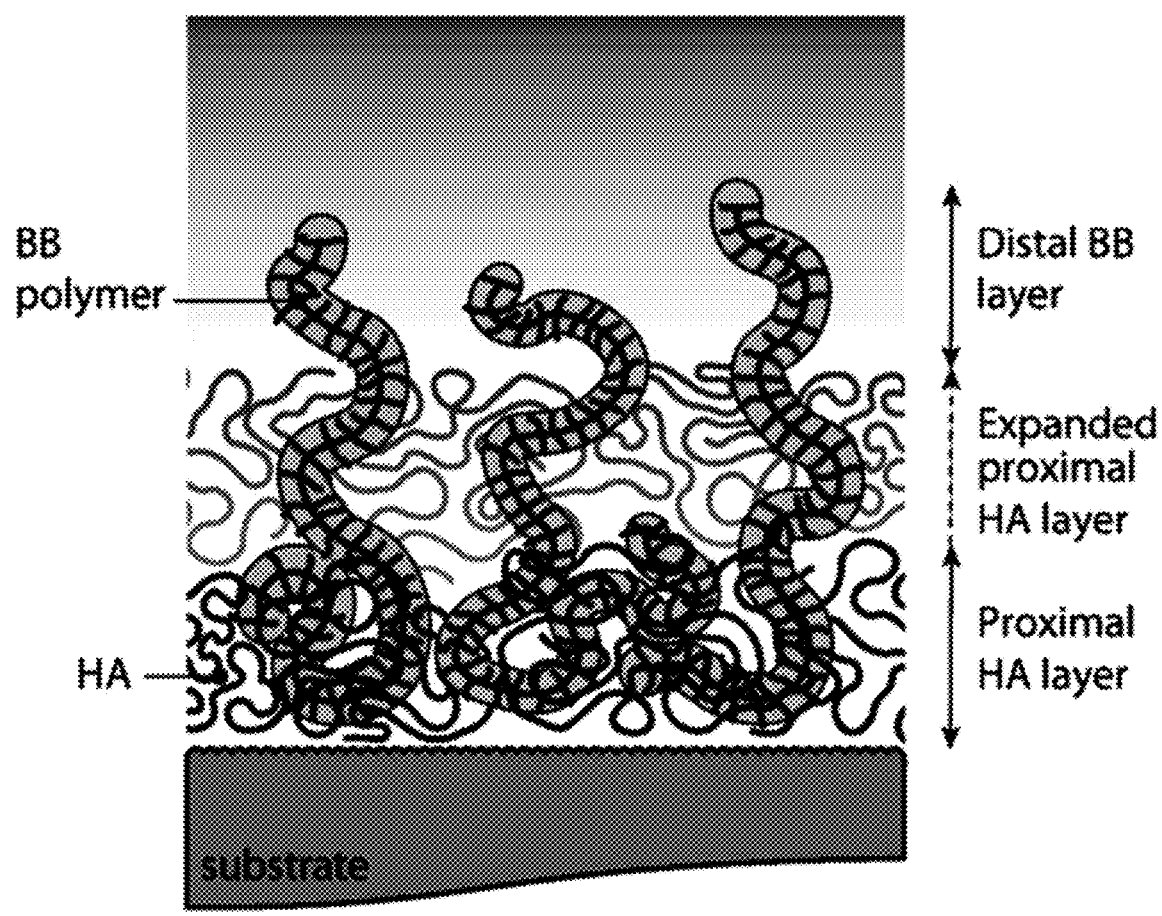
FIG. 14 is a schematic representation of the interfacial polymer layer in the presence of HA and BB polymers.

These force profiles demonstrate that the polymer mixtures form an interpenetrated layered thin film as represented in FIG. 14. The proximal layer of such film contains most of the HA molecules adsorbed at the surface and portions of BB polymer chains, whereas the distal layer is composed solely of BB polymer molecules extending in the medium.

Figure 15:
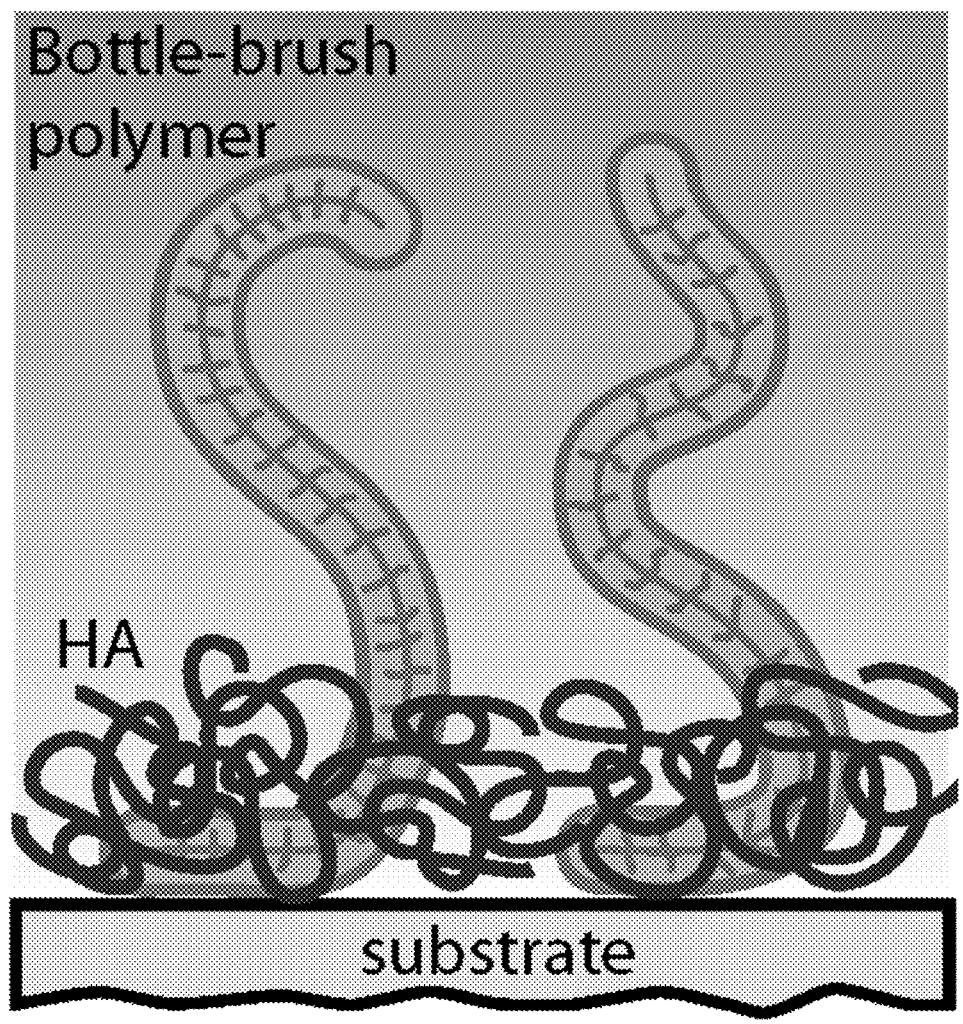
FIG. 15 shows a mixture of a bottle-brush polymer and a linear polymer.

Similarly, FIG. 15 shows a simplified modelized structure of the deposited polymer film as observed in the SFA. A thin film of HA is covering the mica surface together with the bottle-brush polymer. The latter extends in the medium, giving rise to the observed long-range interaction forces measured in the SFA. The short-range part of the interaction forces is dominated by the compression of HA and the bottle-brush polymer.

In pure water, the force profiles of the different mixtures did not exhibit any marked transition between the HA-rich proximal layer and the BB polymer distal layer. Instead, the force profiles show a continuous increase, consistent with an extended proximal layer fully overlapping with the distal layer.

Tribological Properties

Figure 16:
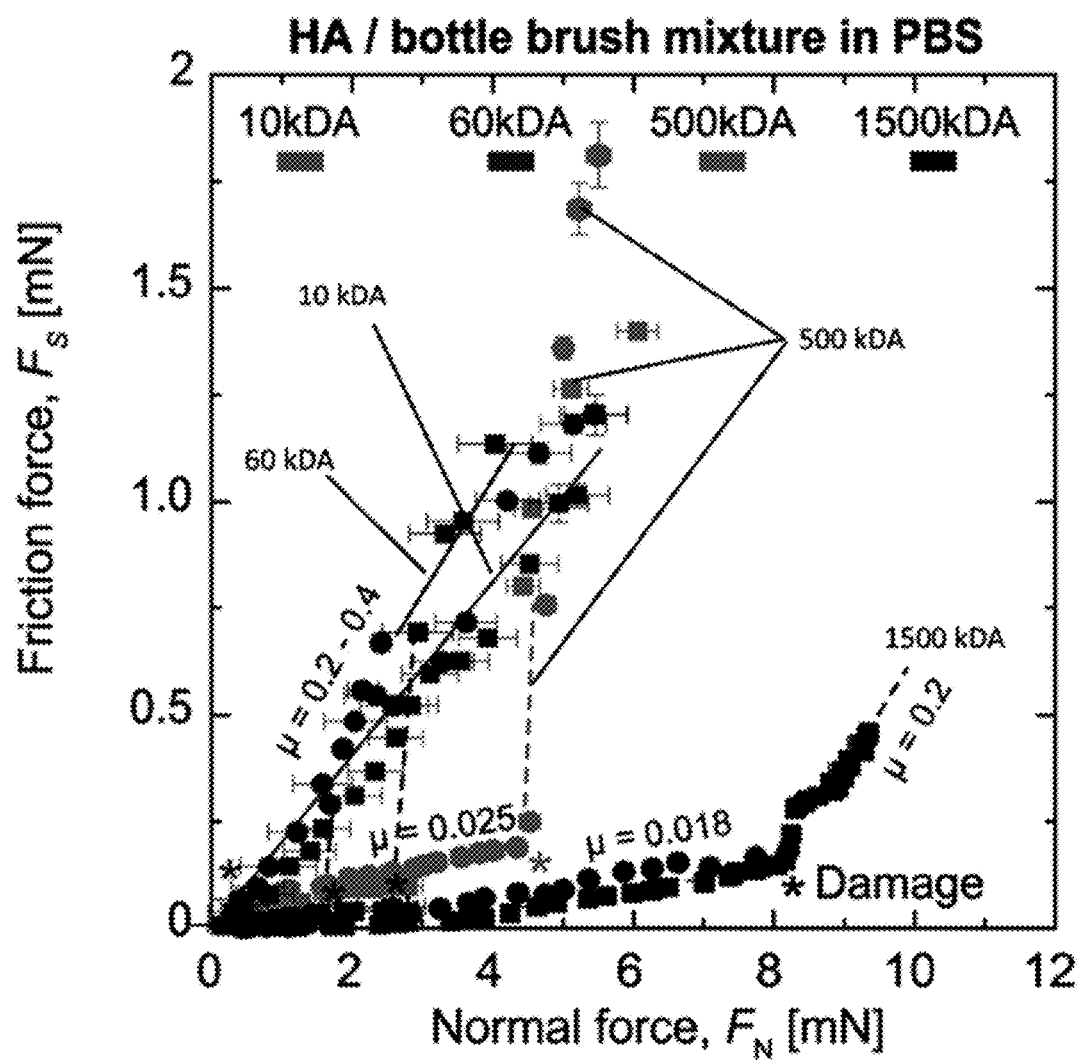
FIG. 16 shows the tribological testing of the BB (0.1 mg/mL) and HA (1 mg/mL) polymer mixtures in PBS (150 mM NaCl) performed at a sliding speed of 3 μm/s.
Figure 17:
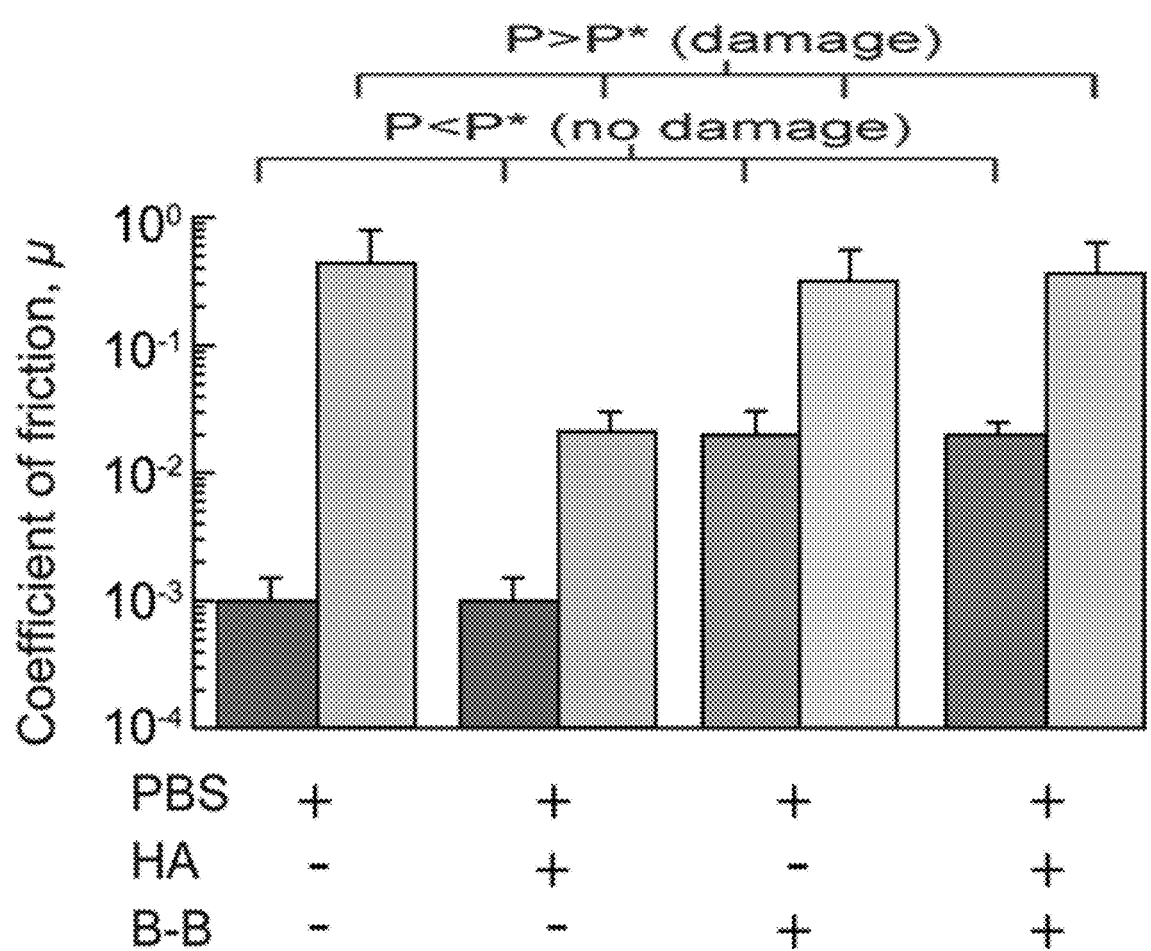
FIG. 17 shows the shows measured friction coefficients in saline (150 and 1500 mM NaCl) before and after damage in the presence of BB and HA polymers, alone and mixed together. Onset of damage is indicated by the "*" symbol.

After measuring the normal interaction forces in the different media, we characterized the tribological properties of the different polymer mixtures. In a first series of experiments, we measured the friction force, $F_S$, as a function of the applied normal force, $F_N$ (FIGS. 16 and 17). For all the tested conditions, $F_S$ was found to increase linearly with $F_N$ until damage of the surfaces occurred (see FIG. 16). We therefore defined the friction coefficient of our system as $\mu=F_S/F_N$. In saline only (no polymer added), frictional forces were very weak (not shown), giving a friction coefficient of $\mu=0.002\pm0.001$ (FIG. 17), in good agreement with previous reports.[24] Using optical interferometry,[25] we measured the critical pressure, P*, at which the onset of surface damage was triggered. Onset of damage appeared as sudden crack formation and propagation along the direction of shearing. We found a value of $P^*=0.73\pm0.03$ Mpa for both saline conditions. We also found that p increased 2 orders of magnitude after damage occurred and ranged between 0.2 and 0.7, as shown in FIG. 17. On the other hand, in pure water, damage of the surfaces occurred almost immediately after a few shearing cycles, indicating that $P^* \approx 0$ Mpa. These results echo recent studies demonstrating that, in saline medium, surface-adsorbed ions facilitate the formation of a lubricating water layer able to sustain a significant amount of normal pressure under shear and therefore protecting the surfaces from damage.[26,27]

In the presence of HA, the measured values of $\mu$ in saline before damage (P<P*) were found to be independent of the molecular weight of the polymer (FIG. 17) and close to the values found in saline only ($\mu \approx 10^{-3}$).

Figure 18:
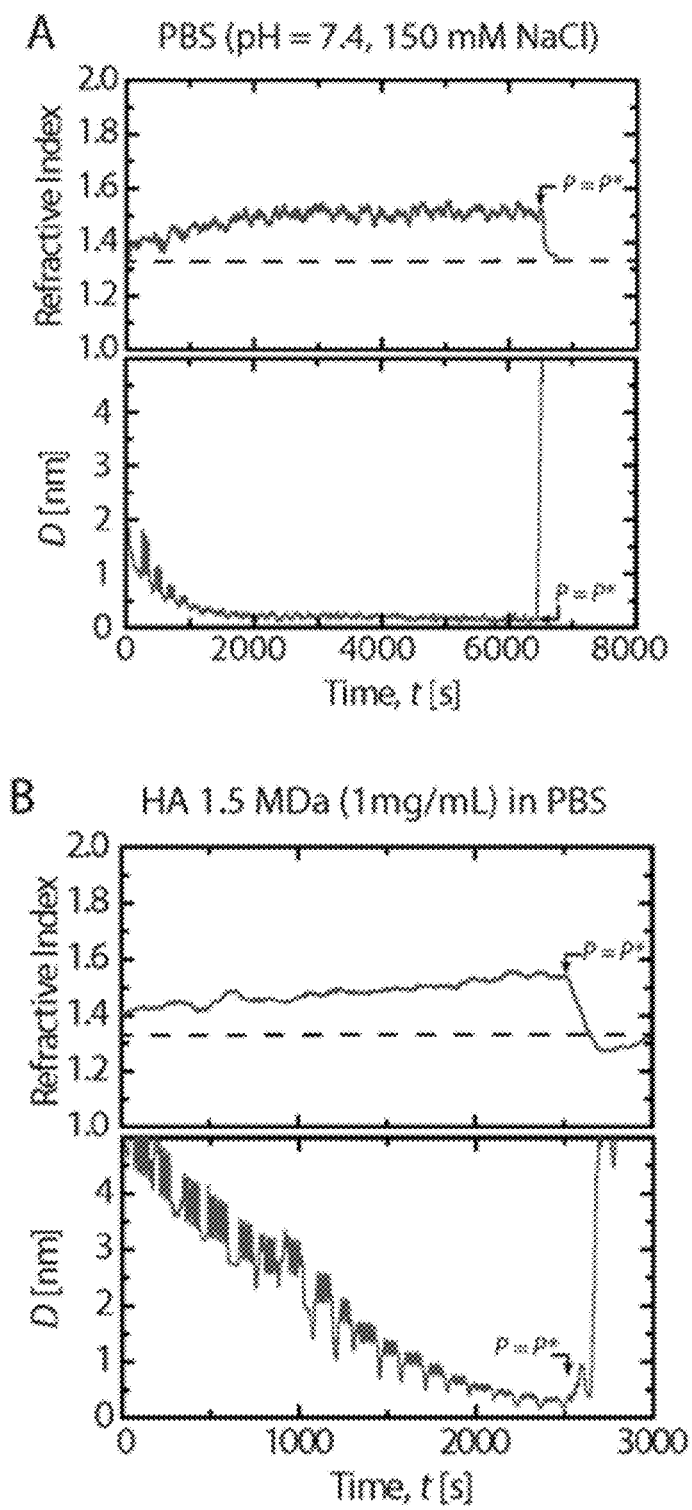
FIG. 18 shows the film thickness and refractive index during shear (shearing speed $v_s$=3 μm/s). The film thickness D decreases gradually due to the increase of the normal pressure/load during the course of the experiment. When P=P*, damage of the surfaces occurs abruptly as shown by the rapid increase in D.

To elucidate if polymer chains were still present in between the surfaces at the onset of wear, we monitored the film thickness and the refractive index of the confined film during shear (FIG. 18). As the applied pressure increased (not shown in the figure) the film thickness decreased and concomitantly, the refractive index of the confined film increases slightly from 1.33 (bulk water) up to ~1.47. Experiments performed in PBS and in buffered HA present the same trend suggesting that HA is quickly depleted from the contact as the normal pressure is applied. In summary, measurements of the thickness and refractive index of the confined film before damage show that the contact area is quickly depleted of polymer, leaving only adsorbed ions and water molecules at the interface (see FIG. 18).

The value of P* for HA was ≈0.7 Mpa, independently of its molecular weight, which is identical to the value encountered in saline only and consistent with the previous observation of HA being depleted from the contact before damage occurs. In pure water, HA solutions demonstrated very poor stability and systematically led to the formation of polymer aggregates in the shearing contact. These polymer aggregates lead to focal pressure increase throughout the contact area and eventually triggered crack formation. As a consequence, the measured value of P* was ≈0 Mpa even though $\mu$=0.02 for all of the $M_w$ tested after damage occurred.

Frictional properties of the BB polymer alone in pure water and saline were drastically different from those of HA or saline alone (FIG. 17). The measured friction coefficient $\mu$ before damage was 1 order of magnitude higher than that of HA or saline alone and was equal to $\mu$=0.03±0.01, independently of the ionic strength of the medium. This result is consistent with the above observation from the normal force profiles showing that BB polymer adsorption and conformation on mica were independent of the ionic strength. In saline and pure water, the measured values of P* were 0.25±0.02 and 0.56±0.04, respectively, which is lower than that of HA and saline alone under similar conditions.

As shown in FIGS. 16 and 17, mixing HA and the BB polymer did not improve significantly the lubricating properties of the surfaces. The measured friction coefficient of the different mixtures before damage (P<P*) was independent of HA molecular weight and equal to $\mu$=0.02±0.01, independently of the medium's ionic strength. This observation suggests that the friction coefficient of the mixture is solely controlled by the presence of the BB polymer when P<P*.

FIG. 17 shows the values of friction coefficients obtained with HA alone and with the bottle-brush polymer. Addition of the bottle-brush polymer increases the friction coefficient from $2.10^{-3}$ to $2.10^{-2}$, similar to the friction coefficient of the bottle brush alone. As shown later, the increase in friction coefficient for the mixture is inversely correlated to the wear protection imparted by the fluid to the surfaces.

Figure 19:
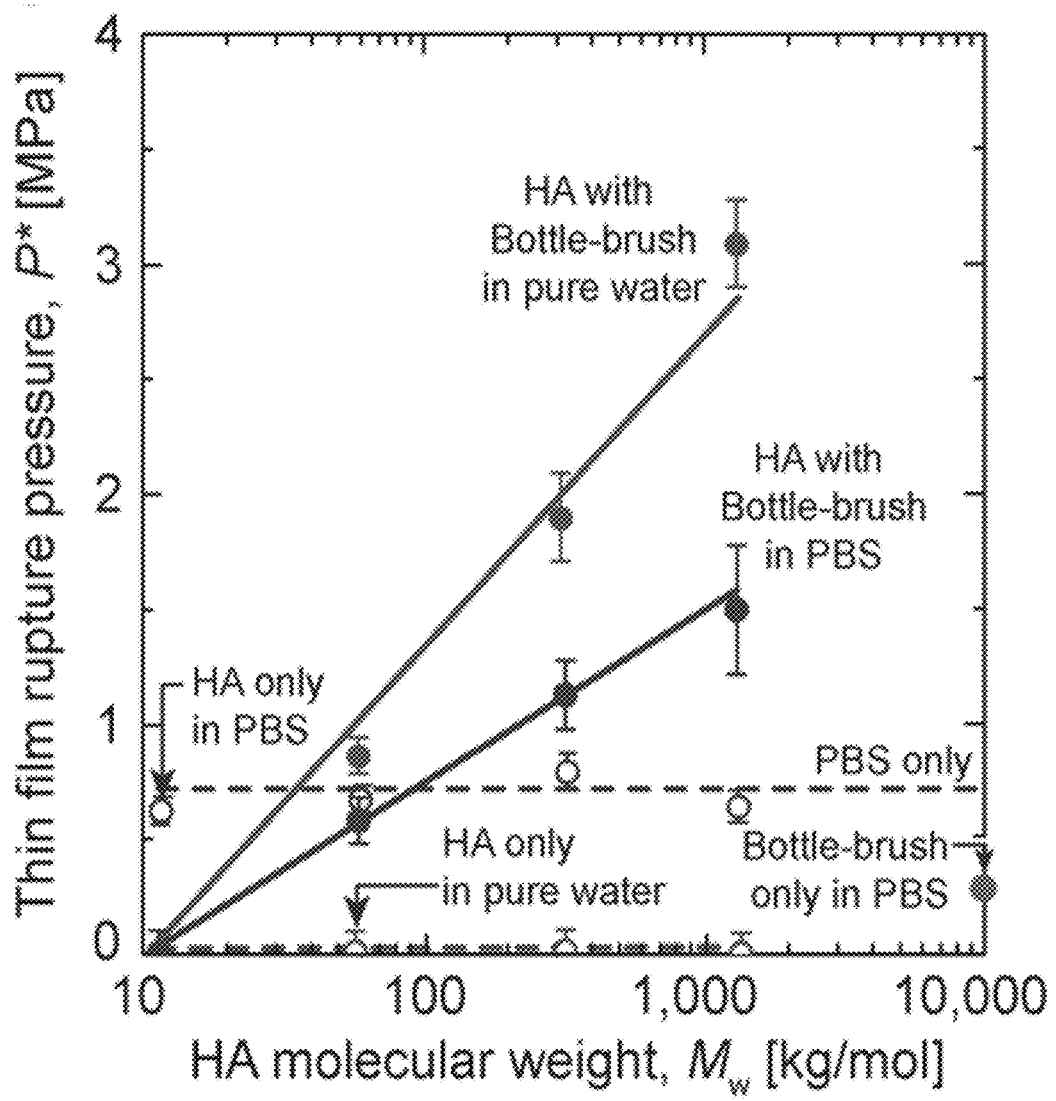
FIG. 19 shows the evolution of the critical pressure at which surface damage occurs (i.e. the thin film rupture pressure P*) under different conditions, wherein HA concentration=1 mg/mL, BB polymer=0.1 mg/mL, and Ratio HA/BB=10:1 at a sliding speed of 3 μm/s.

FIG. 19 shows the evolution of the critical pressure at which surface damage occurs under different conditions. In pure water, HA alone does not sustain any significant normal pressure. Addition of the bottle brush polymer increases the wear protection dramatically, especially at high molecular weights of HA. This same effect was observed in saline conditions, albeit to a smaller magnitude due to the protective effect of the hydration layers on the surfaces generated by adsorbed surface ions. Indeed, the value of P* for each of the components alone was below the value of pure PBS independently of HA molecular weight, while the mixtures presented significantly higher value of P*, especially at high HA $M_w$.

Most interestingly, the value of P*, which relates to the wear protection capacity of the polymer mixture, was highly sensitive to HA molecular weight. As can be seen in FIG. 19, for mixtures with a final concentration of 100 μg/mL of BB polymer and 1 mg/mL of HA (1:10 mass ratio), P* increased significantly with HA molecular weight as P*∝log(Mw). In pure water, the HA-BB polymer mixture led systematically to a significant increase in wear protection, especially at high HA molecular weight, with P* increasing from 0 Mpa in the absence of BB polymer to 3.2 Mpa in the presence of BB polymer. A similar trend was observed in saline solutions, with a 2-fold increase of P* at the highest HA molecular weight in the presence of the BB polymer.

To obtain more insights into the mechanism underlying such a phenomenon, we monitored the evolution with shearing time of the film thickness under different shearing conditions. Measurements of the thin film thickness during shear in pure water and in PBS shown in FIGS. 20 and 21 show that the polymer mixtures are able to sustain significantly more pressure compared to the polymers alone and in a Mw-dependent manner.

Figure 20:
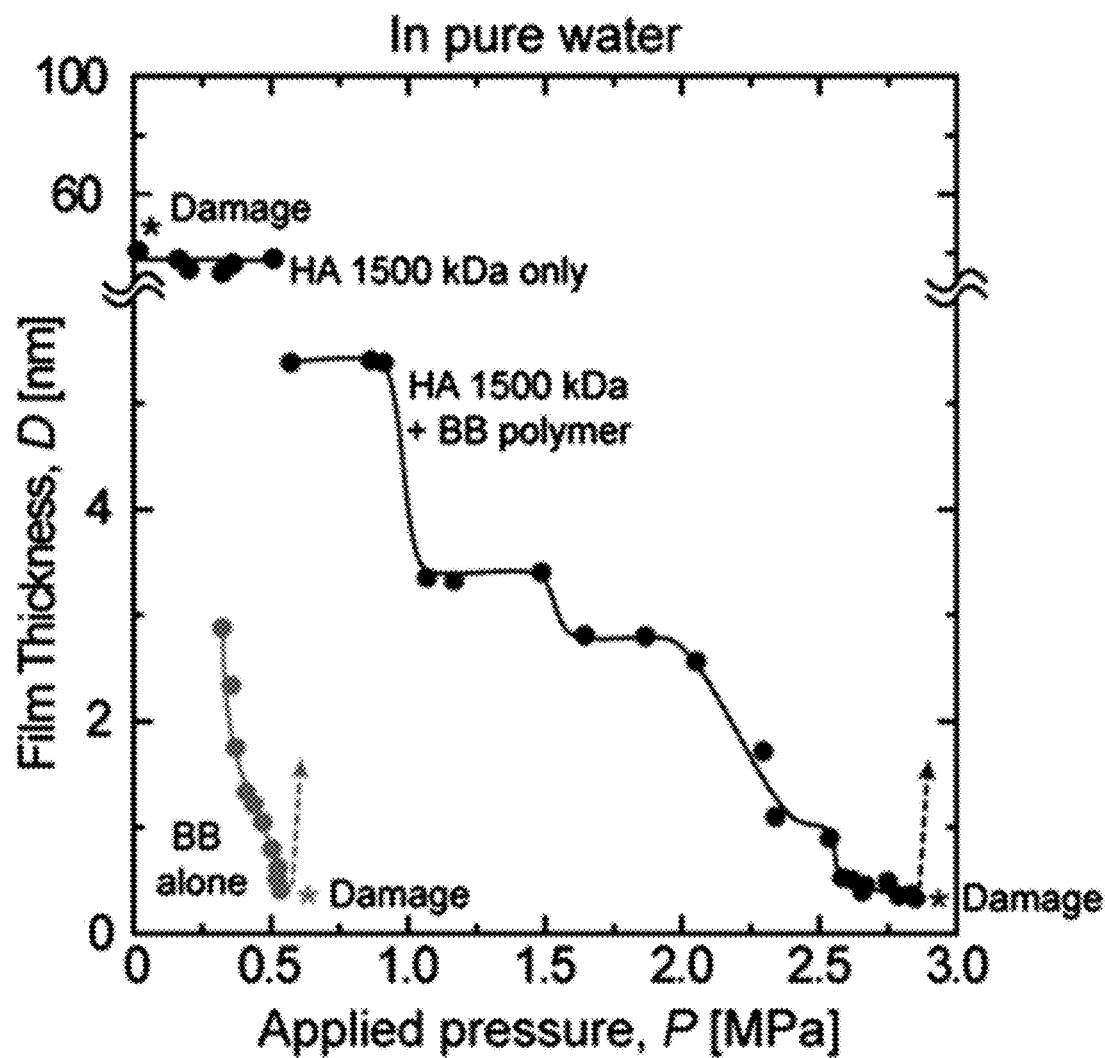
FIG. 20 shows the thin film thickness during shear in pure water.
Figure 21:
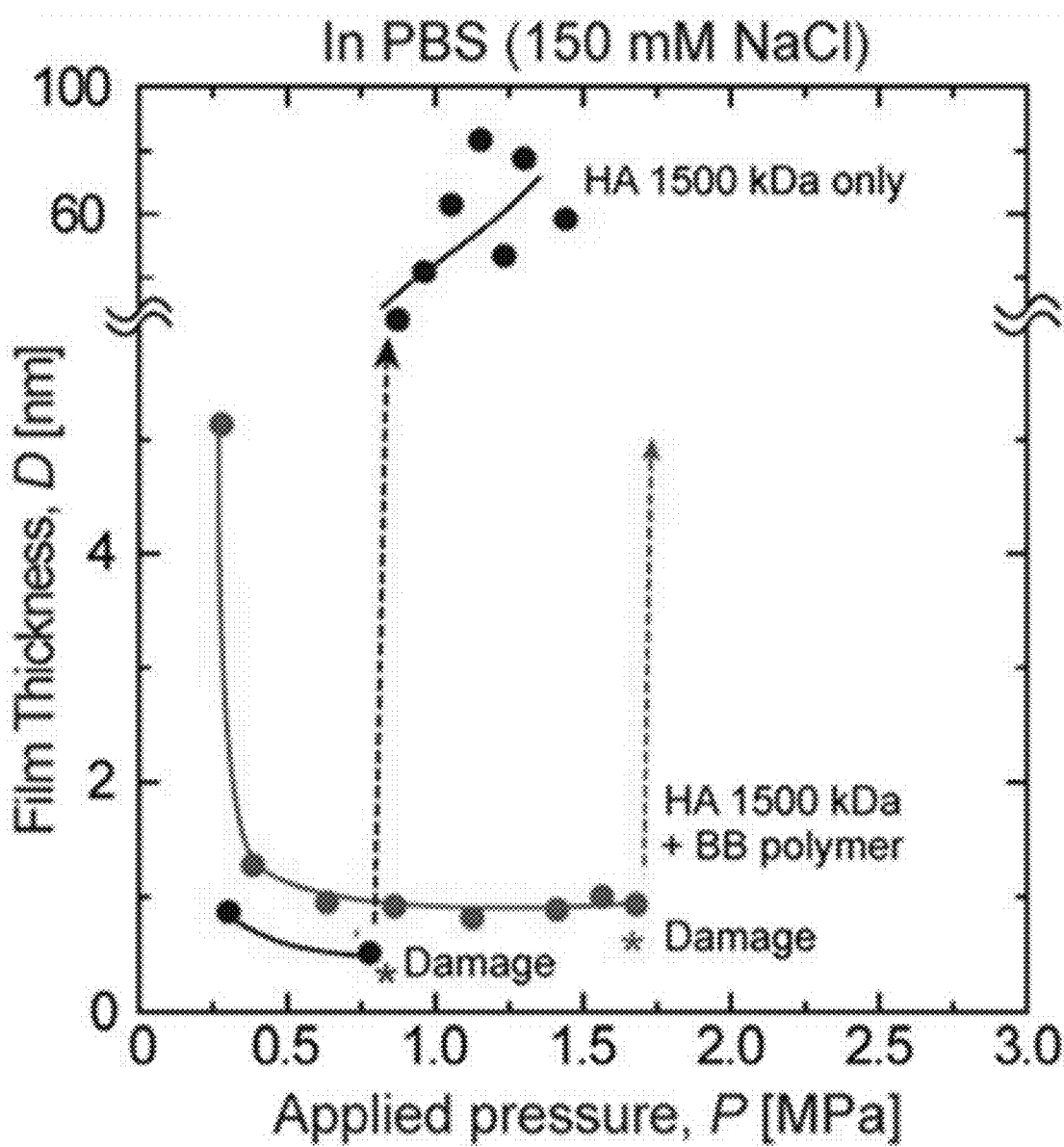
FIG. 21 shows the thin film thickness during shear in PBS.

More specifically, FIG. 20 shows that, as the normal pressure P is increased, the film thickness, D, increases dramatically when the medium contains HA only in pure water, indicating the immediate aggregation of the polymer and the triggering of surface wear. In saline (FIGS. 21 and 18), the data show that HA is quickly depleted from the contact, leading to a rapid decrease of D down to 0.5 nm before damage occurs at P=P*.

In the presence of BB polymers alone, the film thickness at P=P* was 1 nm for both saline conditions, which is thicker than the previously mentioned value obtained for HA solutions. Such a high value of the film thickness indicates that BB polymer chains are still present in the contact at the onset of wear. Similar observations were confirmed with the different polymer mixtures, although the values of P* were significantly higher than BB or HA alone (FIGS. 20 and 21). The significant increase of P* in the case of the polymer mixtures correlates with the higher film thickness at the onset of damage, which indicates the existence of strong intermolecular interactions between HA and the BB polymer. Such interactions maintain a strong cohesion between the different polymer chains under shearing conditions and allows the confined film to sustain significantly more normal pressure.

Figure 22:
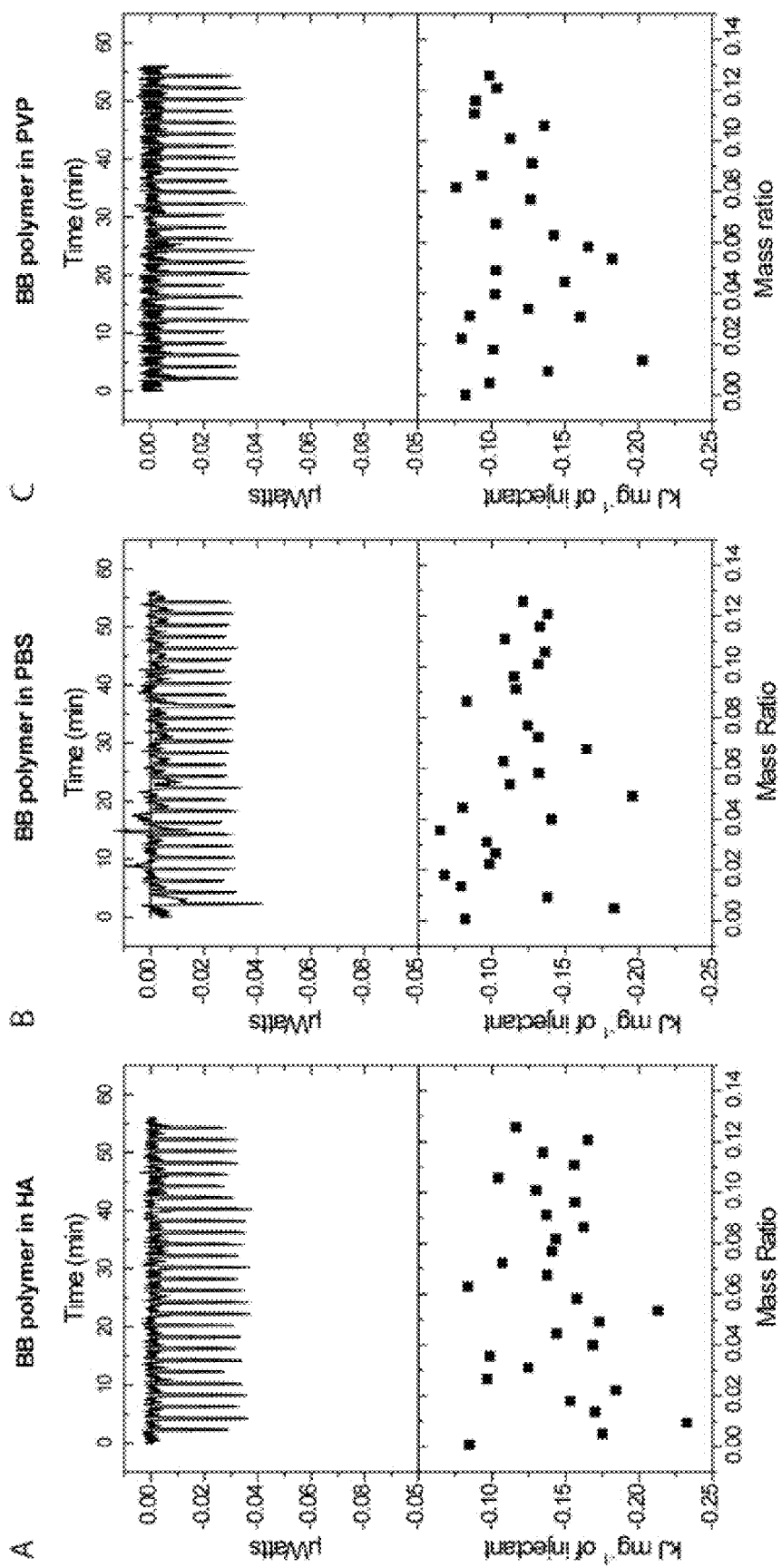
FIG. 22 shows the differential power (top panel) and integrated released heat (lower panel) recorded during the titration of BB polymer into A) HA in buffered saline; B) buffered saline; and C) PVP in buffered saline.

To elucidate the nature of the interactions responsible for such strong intermolecular cohesion, we performed a series of isothermal titration calorimetry experiments (ITC). Isothermal titration calorimetry of the BB polymer in different polymer solutions was performed using a VP ITC from MicroCal. Running on Origin® 7. In the syringe, a buffered BB polymer solution was loaded at a concentration of 0.6 mg/mL and in the receptor cell, a buffered solution of HA or PVP at 1 mg/mL was loaded. All solutions have an ionic strength of 150 mM and were degassed prior use. Experiments consisted in 25 injections of 10 uL each in the receptor cell (1.42 mL) at an injection speed of 2 uL/s and agitation speed of 300 rpm. As a control, the BB polymer solution was also titrated in buffered saline to obtain the dilution heat of the polymer. The results, at FIG. 22, show no differences between the titration experiments in HA or PVP and buffered saline, which demonstrate that there is no direct interaction between the polymers.

Figure 23:
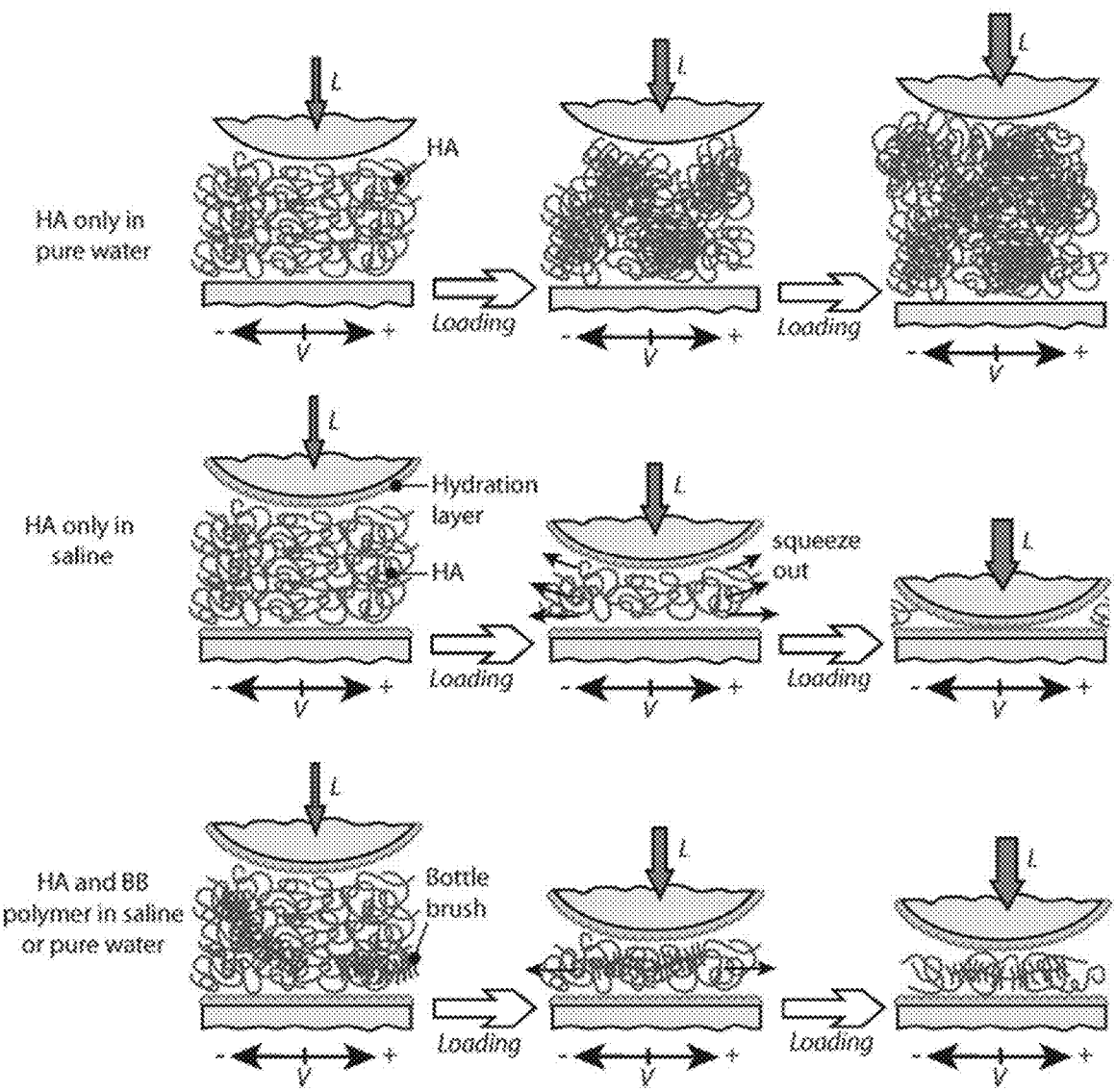
FIG. 23 is a schematic representation of the wear protection mechanism observed in the presence of the mixture of HA and BB polymers in pure water and in saline.

Indeed, no thermal signature was measured during mixing of the polymers, indicating that no detectable interaction (electrostatic or hydrophobic) exists between the two polymers. Therefore, the important role played by HA molecular weight in tuning the cohesive strength of the film demonstrates that chain entanglements are the main factor responsible for the polymer film cohesion (FIG. 23).

In order to demonstrate the generality of the mechanism and its broad application, we performed a second series of tribological tests to establish the impact of shearing speed, BB/HA polymer ratio, polymer chemical structure, and surface chemistry (see FIG. 24 to 28).

Figure 24:
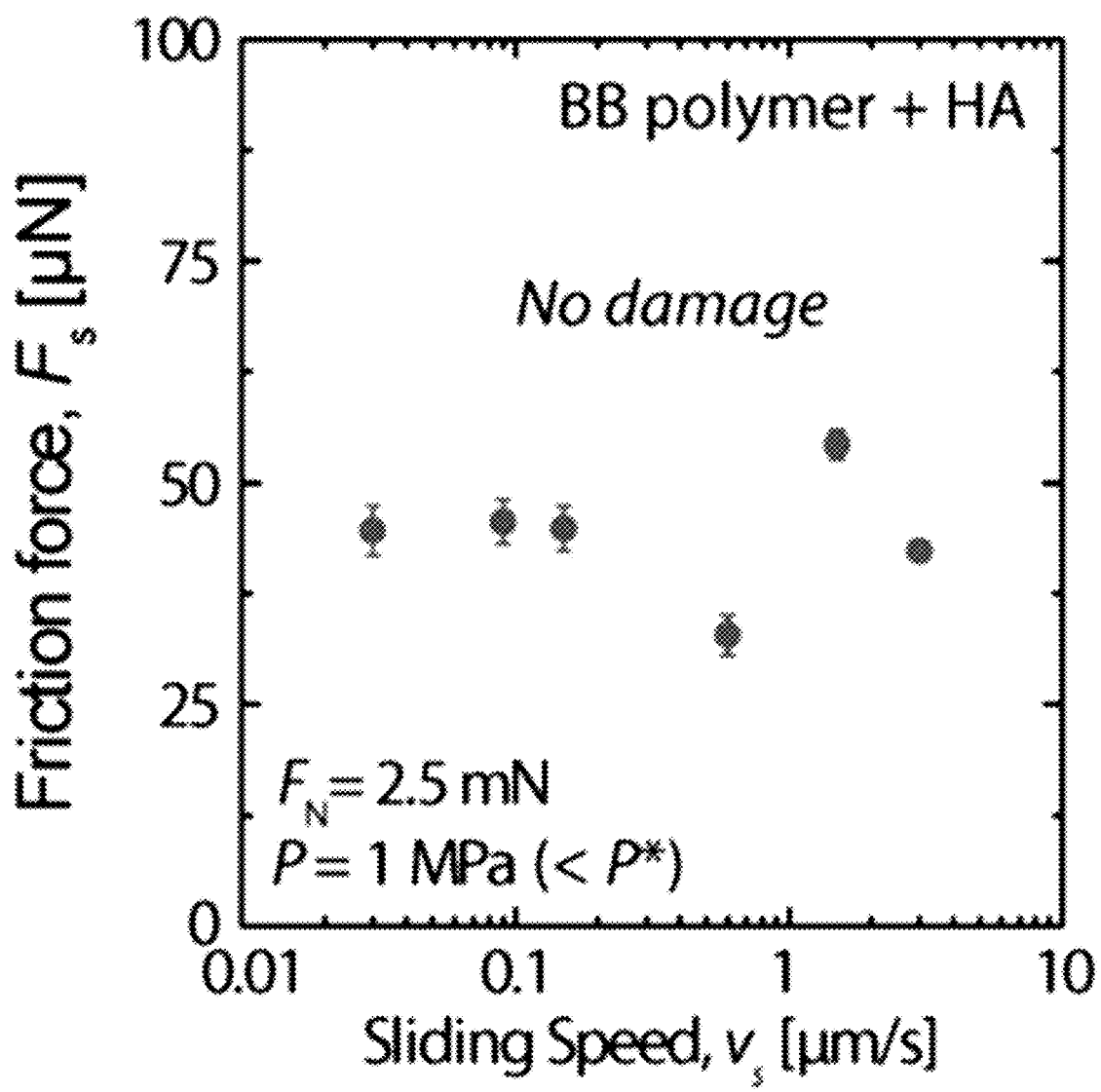
FIG. 24 shows the friction force in the presence of the BB polymer-HA mixture as a function of the sliding speed.
Figure 25:
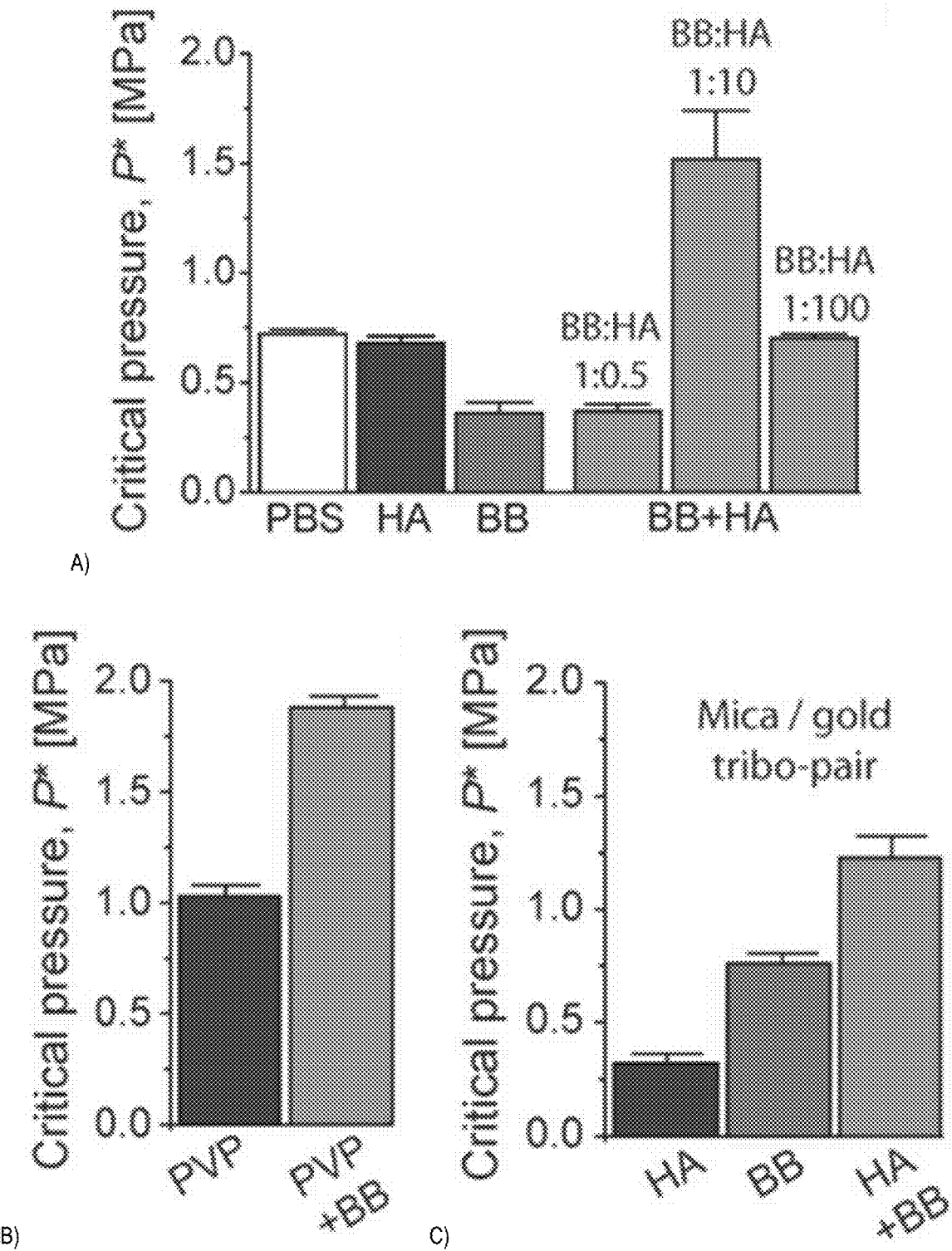
FIG. 25 shows A) the influence of the BB/HA (1.5 MDa) ratio on the critical pressure, B) the influence of the nature of the linear polymer (PVP) on the critical pressure, and C) the influence of the surfaces (mica/gold) on the critical pressure.

FIG. 24 shows that wear protection imparted by the BB polymer-HA mixture was not affected by the sliding speed of the surfaces. At a pressure of 0.5P*, no damage of the surfaces was observed even when varying the sliding speed by 3 orders of magnitude. Indeed, as shown in FIG. 24, varying the sliding speed over three decades, between 0.01 and 10 μm/s at P<P*, did not trigger any damage of the surfaces, indicating a weak dependence, if any, of P* on the sliding speed.

FIG. 25A) shows that BB/HA (1.5 MDa) ratio has a significant impact on P* and was found to be optimum at 1:10. Indeed, in FIG. 25A), we show that P* depends strongly on the BB/HA ratio and is optimum at a ratio of BB/HA=1:10 (mg/mg). Above this optimum ratio, the value of P* is equal to the value of HA F alone, indicating that HA has displaced the BB polymer from the surface. Below the optimal ratio, the value of P* is equal to the value obtained for BB alone, indicating that BB polymer is the sole component in the confined film.

FIG. 25B) shows that HA can be replaced by PVP to obtain similar synergistic wear protection when mixed with the BB polymer. Indeed, a similar synergistic behavior between BB polymer and HA was also observed when replacing HA with poly(N-vinylpyrrolidone) (PVP), a neutral, water-soluble polymer (M=40 kDa). FIG. 25B) shows that the value of P* in saline (150 mM, pH 7.4) exhibits a 2-fold increase with a 1:10 mixture ratio of BB/PVP compared to PVP alone. Similarly to HA, PVP did not show any direct interaction with the BB polymer by ITC (FIG. 22).

The HA-BB polymer mixture was tested against mica/gold tribo-pair, as well—see FIG. 25C). The wear protection enhancement was similar to that of mica/mica. Gold being a ductile metal, its tribological properties are very poor in terms of wear resistance. For the tribo-pair mica/gold, P* was inferior by 1 MPa in the presence of HA or BB polymer alone. As shown in FIG. 25C, the polymer mixture was once again significantly more efficient at protecting the surfaces compared to the single components alone.

In all the tested conditions, the value of P* associated with the polymer mixture is systematically superior to the sum of the value associated with the polymers alone, indicating a true synergistic interaction between both components in terms of wear protection.

Figure 26:
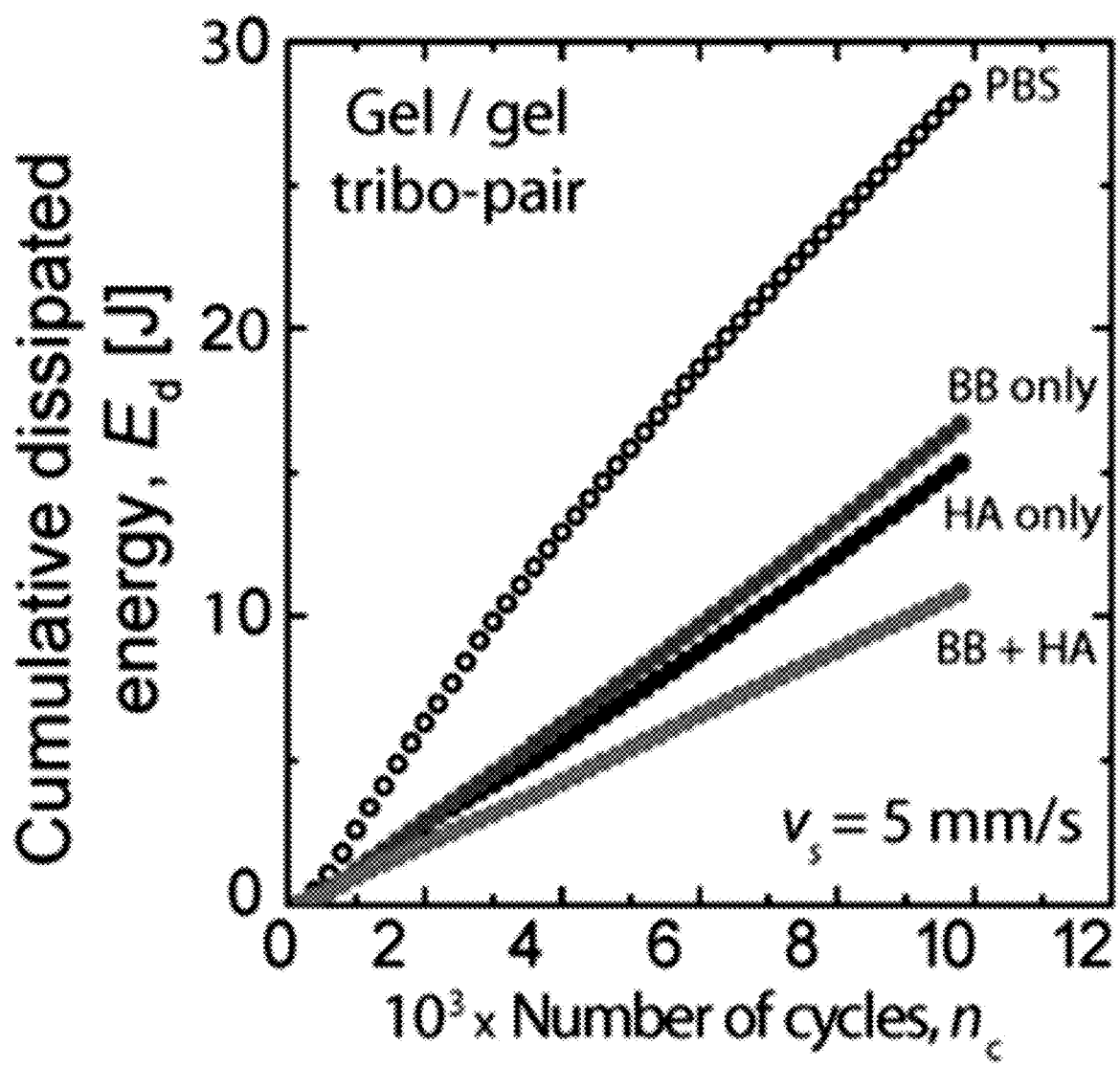
FIG. 26 shows the cumulative dissipated energy generated during shearing of two 2.5 wt % chitosan hydrogel plugs, lubricated with different polymer solutions.
Figure 27A:
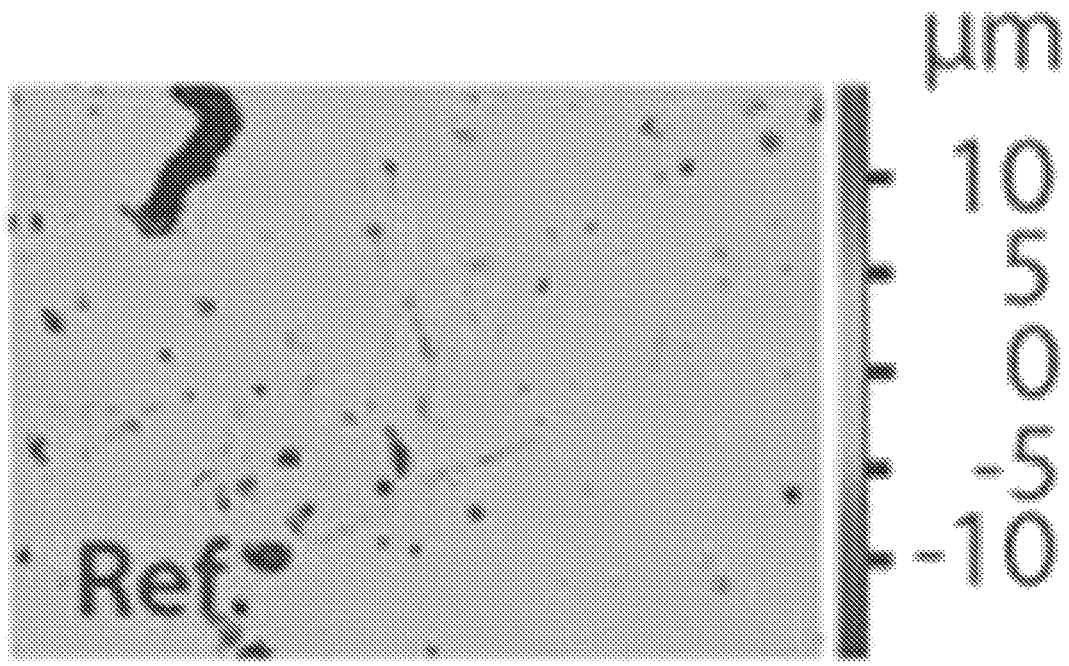
FIG. 27 shows interferometric micrographs of the hydrogel plugs after $10^4$ shearing cycles at 5 mm/s (shearing amplitude of 5 mm, applied pressure P=50 kPa): A) reference, B) PBS, C) HA, D) BB polymer, and E) polymer mixture.
Figure 27B:
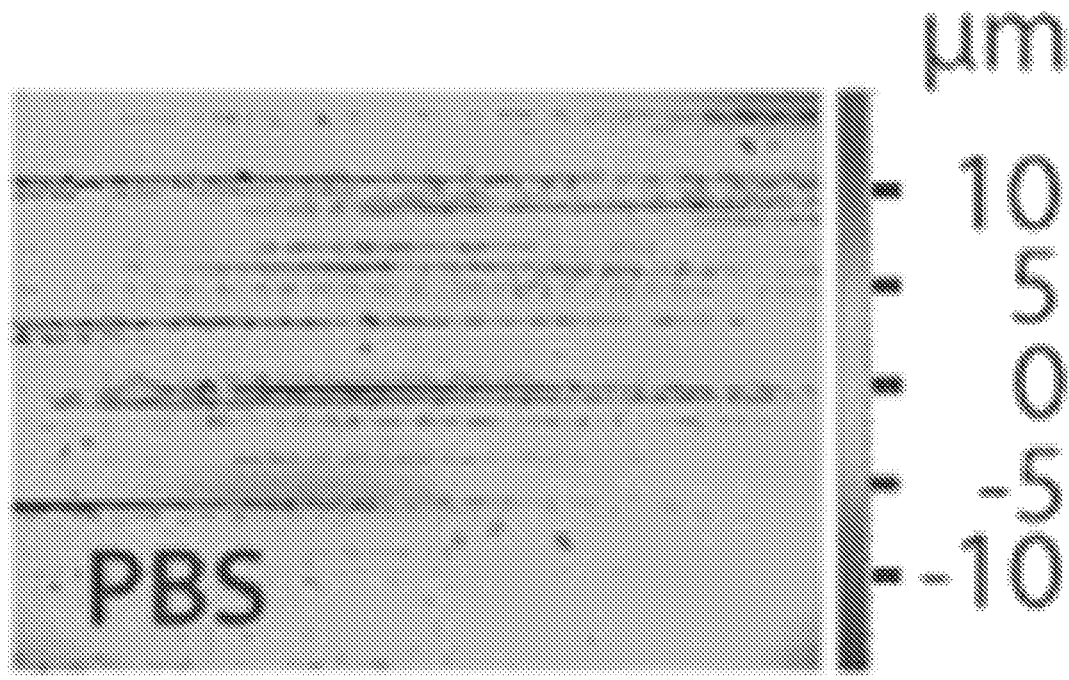
Figure 27C:
Figure 27D:
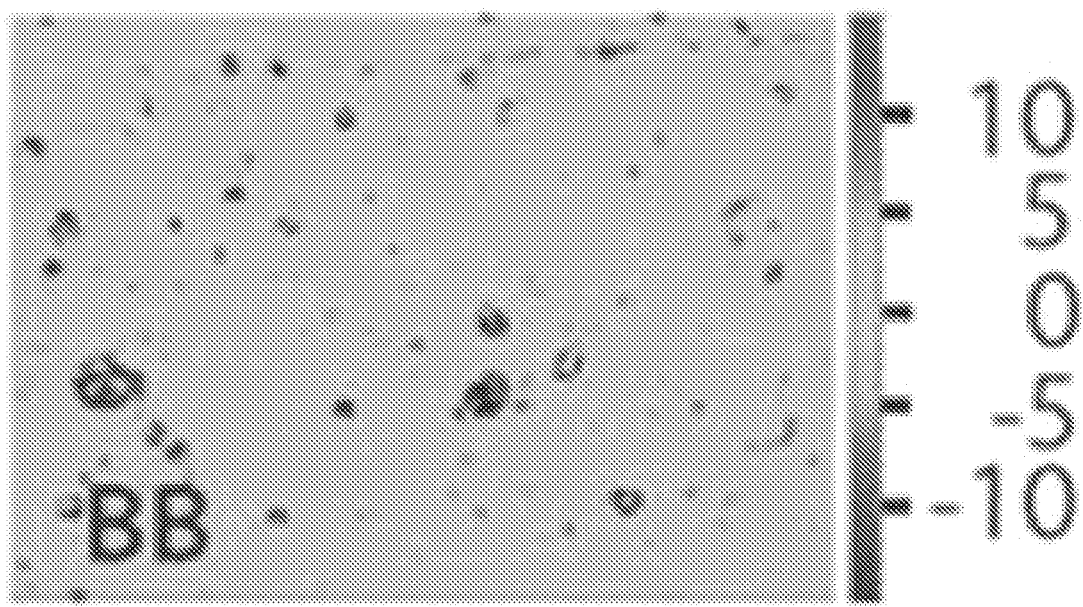
Figure 27E:
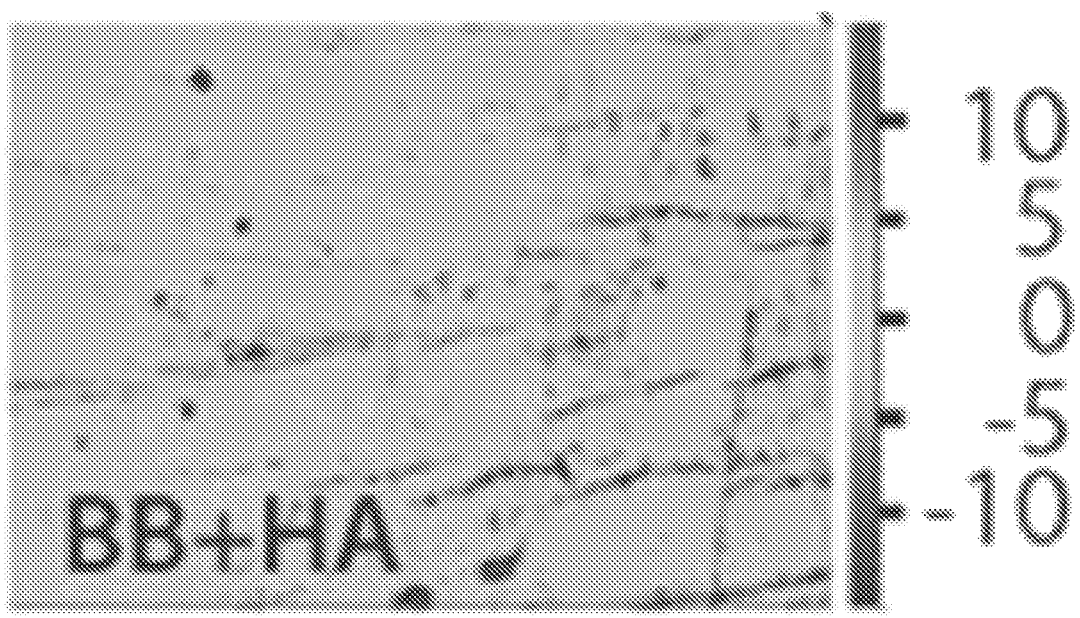
Figure 28:
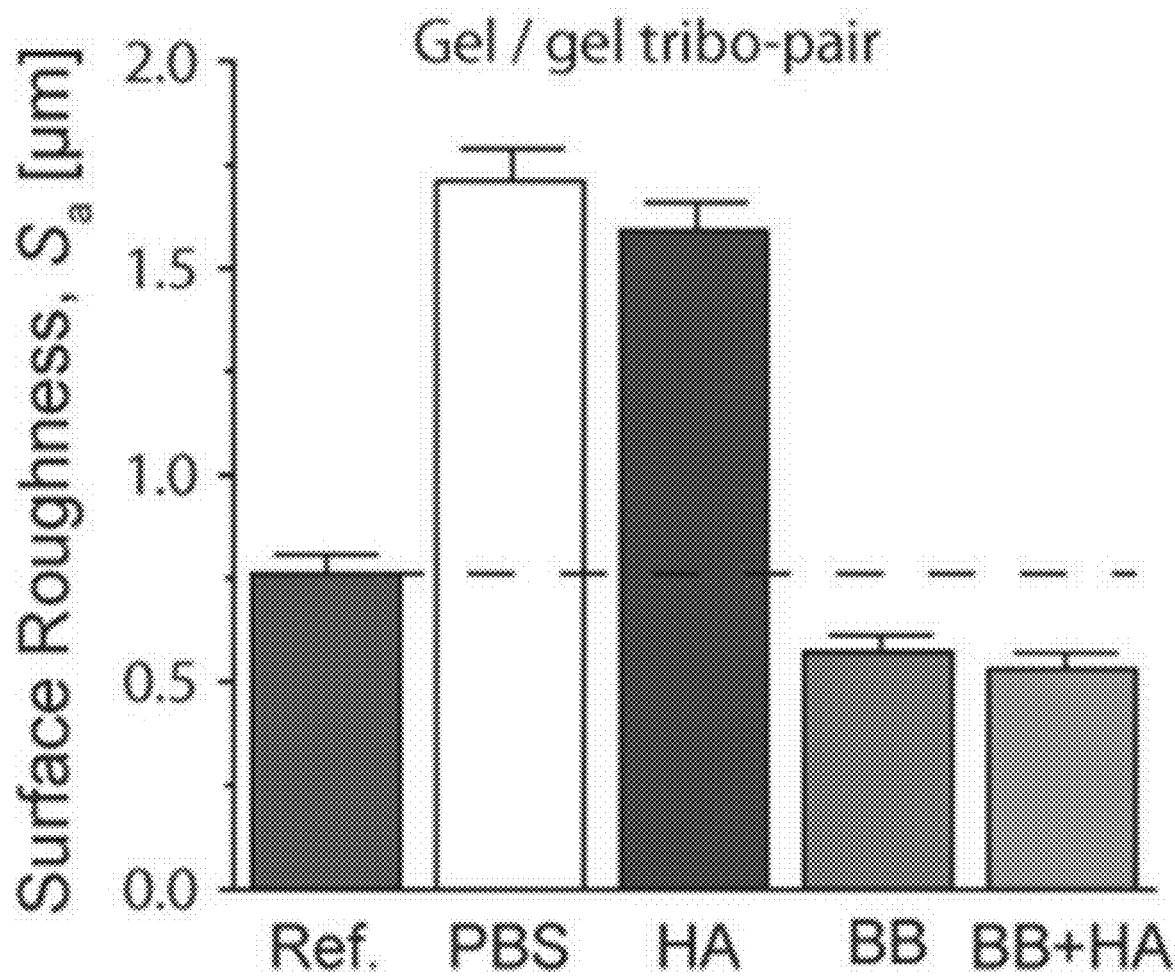
FIG. 28 shows the surface roughness associated the interferometric micrographs shown in FIG. 10.28.

We finally tested the lubricating fluids between macroscopic hydrogel plugs of chitosan as model soft polymeric surfaces (FIGS. 26 to 28). Chitosan hydrogels have been extensively tested as cellular scaffolds for tissue engineering applications, but their poor resistance against abrasive wear has hampered their translation to clinical settings. Tribotesting of the hydrogels (2.5 w %) has shown that the cumulated dissipated energy, Ed, which is directly related to the wear volume, $W_v$, is strongly diminished in the presence of the HA-BB mixture compared to each component alone. Concomitantly, the surfaces' roughness, $S_a$, was found to significantly decrease in the presence of the mixture compared to all other conditions due to surface polishing and restructuring.

Further Results

Figure 29:
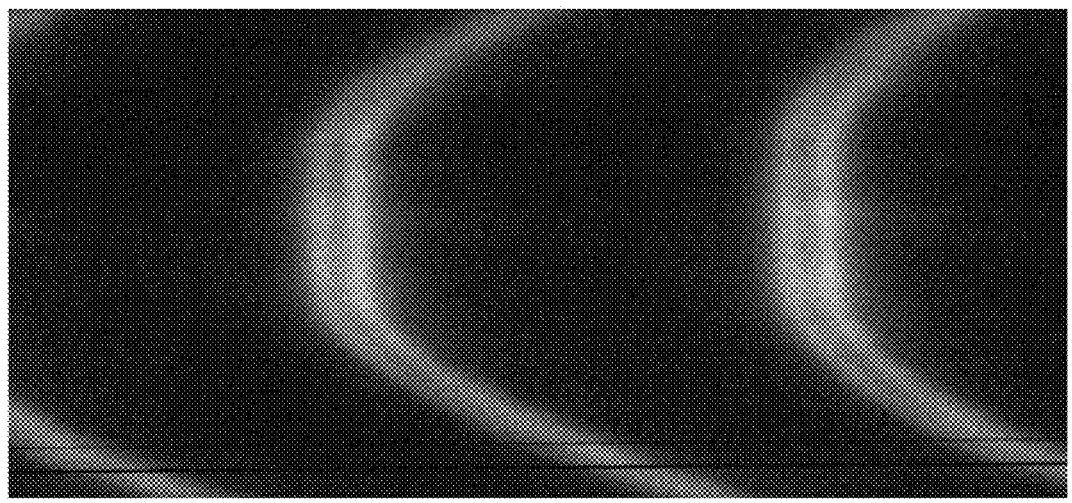
FIG. 29 shows the Example of FECO fringes showing no damage (up) and damaged appearance (down).
Figure 29:
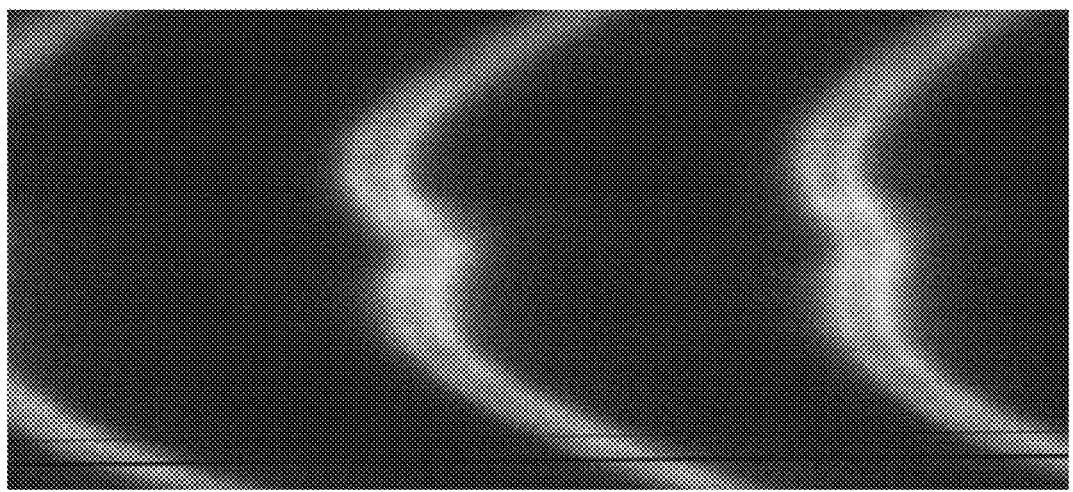

FIG. 29 shows an example of FECO fringes with no damage (up) and damaged appearance (down). The shape of the FECO fringes is indicative of the shape of the surfaces' contact point. Slight deformations in the fringes' shape indicate the appearance of a third body trapped in between the surfaces. Said third body can be generated by the aggregation of the confined polymer film under shearing conditions, or it could be composed of mica particles formed by abrasive wear of the surfaces. In any case, these changes in contact geometry can be used to track the onset of any kind of wear process occurring during a tribological measurement without the need of separating the surfaces or the use of any extra imaging techniques.

Effect of HA/BB weight ratio, and testing of other linear polymers (in PBS, HA Mw=1.5 MDa, PVP Mw=35 kDa)

| Mixture composition | Pressure of rupture (MPa) |
|---|---|
| PBS only | 0.7 |
| HA only | 0.7 |
| HA:BB 1:1 | 0.4 |
| HA:BB 10:1 | 1.6 |
| HA:BB 100:1 | 0.7 |
| PVP only | 1 |
| PVP:BB 10:1 | 1.9 |

(HA = hyaluronic acid,
BB = bottle-brush polymer as described above.
PVP = poly(vinlpyrrolidone)

Example 2—In Vitro Stability

We also evaluated in vitro stability of the bottle-brush (B1) polymer.

The bottle-brush polymer used for Examples 2 and 3 was similar to that of Example 1, except that it had a backbone comprising 370 units of methylmethacrylate (MMA) and 459 units of hydroxylethylmethacrylate (HEMA), with pendant chains containing 35 unit of 2-methacryloyloxyethyl phosphorylcholine (MPC) grafted on the hydroxylethylmethacrylate repeat units. The grafting ratio was 0.55. In other words, the BB polymer was $(PBiBEM_{456}$-g-$PMPC_{35})$-stat-$PHEMA_3$-stat-$PMMA_{370}$.

The BB polymer (white powder) was dissolved at 100 μg/mL in a homemade PBS composed of 10 mM phosphate ions and 150 mM NaCl with a pH 7.4. The polymer was left this saline solution in a dark container at 4° C., 22° C. or 37° C.

A Surface Forces Apparatus (SFA 2000, SurForce LLC, USA) was used to measure the normal force profiles of the BB solution. Back-silvered mica sheets were glued (epoxy glue Epon™ 1004F) on glass cylinders with a curvature radius, R, of 2 cm under a laminar flow hood. The cylinders were mounted in SFA chamber in a cross-cylinder configuration. The SFA chamber was then purged with dry nitrogen and the surfaces were brought into adhesive contact to measure the zero contact using a spring cantilever with a spring constant of 482 N/m.

The separation distance between the two opposing mica surfaces was determined from the FECO fringes using mica-mica contact. The surfaces were then separated and 50 µL of BB polymer solution were injected between the surfaces and pure water was injected in the chamber to saturate the vapors to prevent solution evaporation. The setup was left to equilibrate for 1 h. The normal interaction forces, $F_N$, were recorded as a function of separation distance, D, for in (compression) and out (separation) runs at a speed of 0.002 µm/s. The fringes were analyzed using a Matlab software. Experiments were performed at least three times at different contact positions.

Figure 30:
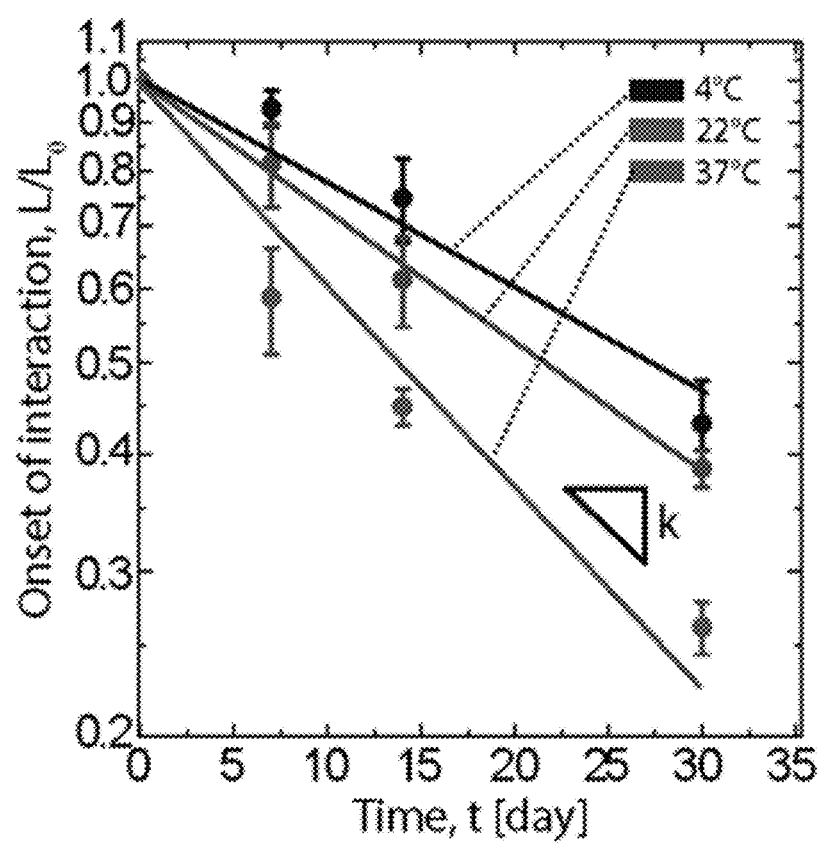
FIG. 30 shows the onset of interaction as a function of time at different temperature.
Figure 31:
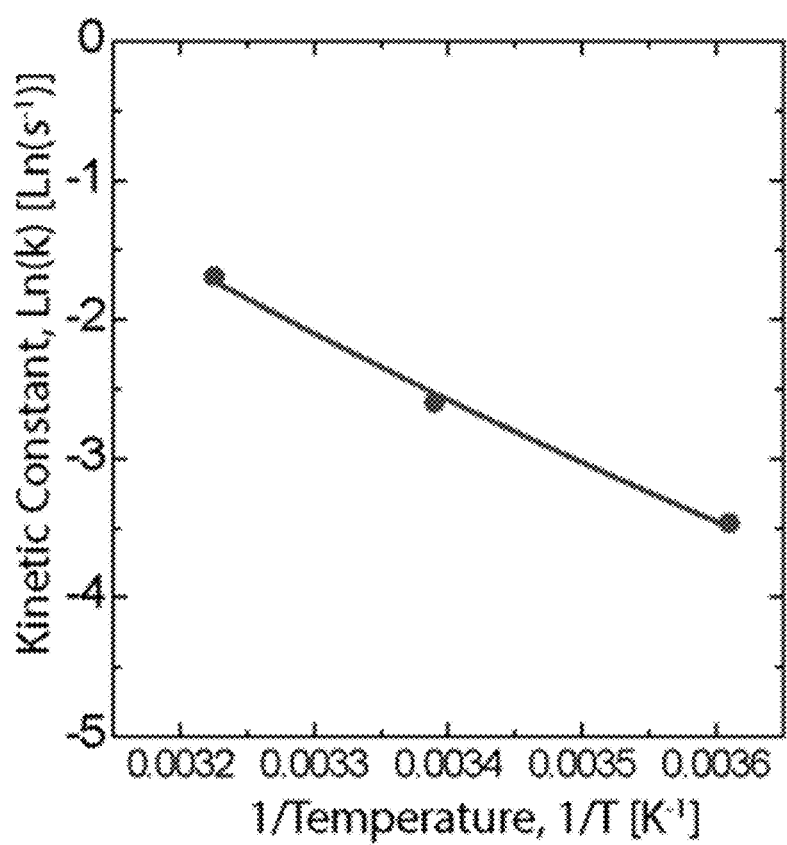
FIG. 31 shows the kinetic constant as a function of 1/temperature.

FIG. 30 shows the onset of interaction as a function of time at different temperature. FIG. 31 shows the kinetic constant as a function of 1/temperature. The results shown in these figures confirm that the polymer conformation at the surface changes with time and temperature mostly due to the loss of pendant chains from hydrolysis. Arrhenius plot shows that the activation energy of the degradation reaction is consistent with a hydrolysis reaction.

Example 3—In Vivo Tests

Materials and Methods
Rat Model of Osteoarthritis Animals

Eight-week-old male Lewis rats were purchased from Charles River Canada (Saint-Constant, QC) and housed under standard conditions. They were housed at 25° C. with a 12:12-hour light-dark cycle and provided with a standard laboratory diet and water ad libitum. The experimental protocol and all animal procedures were carried out in accordance with the guidelines of the Canadian Council on Animal Care (CCAC) and was approved was approved by the Institutional Animal Care Committee at the Research Center of Sainte-Justine University Hospital, Montreal, Canada.

Study Design

The study was conducted as a fractional factorial experiment. Animals were submitted to surgery anterior cruciate ligament transection (ACLT) was performed on the right posterior knees, and no surgery (negative control) on the left posterior knees. Subsequently, animals were assigned to one of two treatment groups, as detailed below (Table 1), with 2 subjects per group.

TABLE 1

Experimental groups

| Group Number | Surgery | Treatment |
| --- | --- | --- |
| 1 | ACLT | HA (2 mg/ml) in PBS (50 microliters) |
| 2 | ACLT | HA (2 mg/ml) in PBS (50 microliters) |
| 3 | ACLT | HA (2 mg/ml) + BB (350 µg/ml) in PBS (50 microliters) |
| 4 | ACLT | HA (2 mg/ml) + BB (350 µg/ml) in PBS (50 microliters) |

HA: Hyaluronic acid
BB: Bottle-brush polymer as described in Example 2.

Surgical Technique

Figure 32:
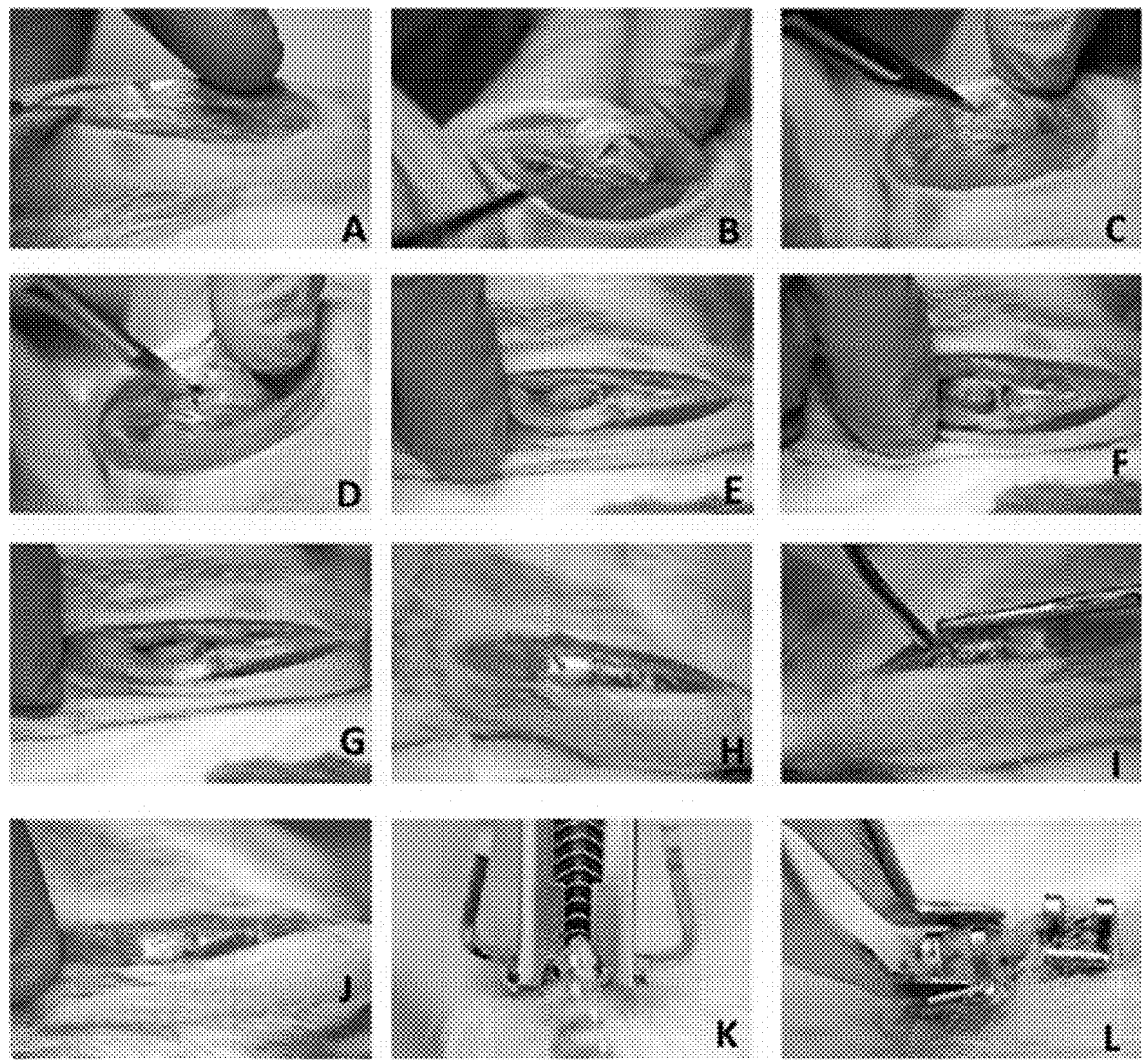
FIG. 32 shows the steps of rat ACLT surgery as carried out in Example 2.

OA was induced by surgical transection of the right anterior cruciate ligament. The procedure was modified from previously published reports (Appleton et al Arthritis Research & Therapy 2008 10:407). We published this surgery technique in Kaufman et al Arthritis Research & Therapy (2011) 13:R76. Animals were anaesthetized with inhaled isoflurane (3% 1 L 02 induction in chamber, 2% 1 L 02 maintenance with face-mask), and prepared for surgery by clipping the hair over the ventral and medial aspects of the right leg from hindpaw to hip. The skin was disinfected with povidone-iodine, and a 3-cm incision was made medial to the patellar tendon (FIG. 32A)). The subcutaneous tissue and muscle were then incised and the patella laterally sublaxed; the joint capsule was opened with the limb hyperextended (FIG. 32B)). With the limb in full flexion, the anterior cruciate ligament was visualized by blunt dissection, and sectioned by a latero-medial eut parallel to the tibial plateau, using a \#11 scalpel blade (FIGS. 32C) and D)). Transection was confirmed with the anterior drawer test (FIGS. 32E) and F), E depicting the knee before, and F) showing an anterior drawer). The patella was then replaced, and the limb extended (FIG. 32G)). The joint capsule (FIG. 32H)) and muscle layers (FIG. 32I)) were closed with 4-0 polygalactin absorbable suture (horizontal mattress stitch, FIG. 32J)). 50 µL of lidocaine was then injected into the joint capsule to provide local analgesia. Skin was closed with steel surgical staples (FIG. 32K)). Post-operative hydration (6 mUkg saline) and systemic analgesia (0.1 mg/kg buprenorphine HCl) were provided by subcutaneous injection. Surgical staples were removed 7 days post-operatively (FIG. 32L)).

Drug Treatment

Over the course of two weeks post-operatively, animals were treated by weekly intra-articular injections of 50 microliters of HA (2 mg/ml) in PBS, or HA (2 mg/ml)+BB (350 µg/ml) in PBS. The total volume was 50 µL. Injections were performed under isoflurane anaesthesia, using a 28 G needle. The compounds were injected into the right knee. All Injections were performed under isoflurane anaesthesia, using a 28 G needle.

Figure 33:
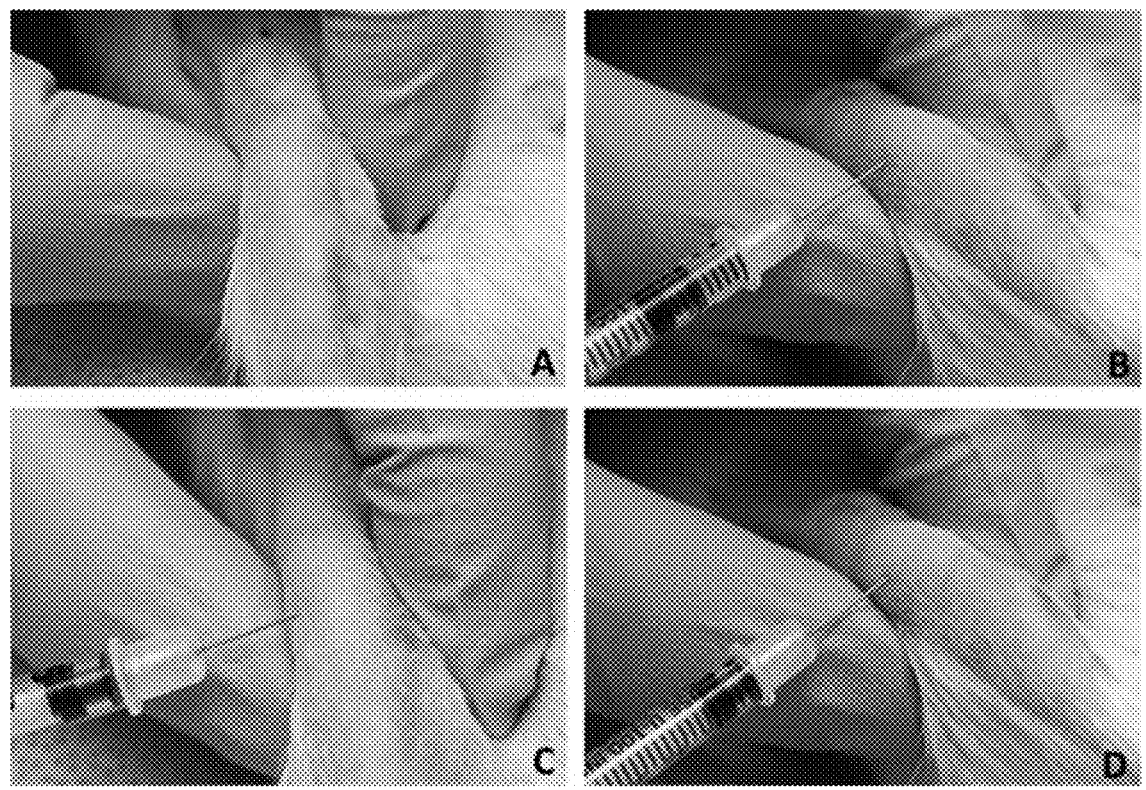
FIG. 33 shows the intra-articular injection into the rat knee.

FIG. 33 shows the intra-articular injection into the rat knee: The shaved knee was maintained in extension (FIG. 33A))), the needle was inserted under the patellar tendon into the joint space (FIG. 33B)), the syringe plunger is depressed slowly (FIG. 33C)), successful injection was detected by an acute swelling of the articular space (FIG. 33D)). Photographs were taken with a 300-mm macro lens (approximate magnification 2, as described in Kaufman et al. 2011, supra).

In Vivo Micro-CT Scanning
Micro-CT Scanning

Micro-computed tomography (micro-CT) is an efficient tool for the study of bone morphometry and 2D/3D image analysis. In particular, it constitutes a valuable tool for the non-destructive evaluation of laboratory animals and the in vivo tracking of anatomical changes in bone, bone mass and bone microstructure. In this study, we analyzed the geometrical parameters of the rat knee aiming to quantify the intra articular space in control and experimental conditions.

We used a Skyscan 1176 micro-CT imaging (Skyscan, N.V., Belgium) scanner with rotatable X-ray source and detector. After $CO_2$ asphyxiation, followed by decapitation, both left (control) and right (surgery) knees were removed, and scanned by the micro CT. To do so, right and left knees were separately into a cylindrical Styrofoam holder placed in a carbon fiber half-tube bed of the Skyscan 1176. This was done in order to position the limb at the scanning midline during scanning.

Image acquisition parameters were the followings: X-ray source voltage 65 kV, current 384 µA, full X-ray power, and 1-mm thick aluminum filter for beam hardening artifact reduction. The pixel size was 18 µm for a 2,000×1,336 CCD detector array. The exposure time was 350 ms, the rotation step 0.5°, with 1 frame averaging, and gantry direction in CC. The total scanning time was 15 min. During acquisition, the scanning consisted of a stack of 720 images. The acquisition covered the region of the knee joint from just above the proximal tibia and extended up to the tibiofibular joint. Cross-section images were reconstructed using a filtered back-projection algorithm (software NRecon, v.1.6.10, Skyscan, Kontich, Belgium). For each scan, a stack of 1,328 cross sections was reconstructed corresponding to a total reconstructed height of 10 mm, starting from the knee joint and extending distally along the tibial diaphysis, with an interslice distance of 1 pixel (17.48 µm). The reconstructed images were of 772×772 pixels each, 17.48 µm pixel size, and were stored as 8-bit images (256 gray levels).

Using the micro-CT, we first evaluated the impact of surgery (OA development) and then we quantified the spaces between the two bones: among 1200, 70-80 images were chosen where distances between the distal femur and the proximal were less than 900 □m. Six images of each group were then analysed, performing 8-10 measurements on each image To compare the values of the intra-articular space (space between the femur and tibia) a paired Student's t-test was performed. This comparison was performed to assess the possibility of the increased space effect of polymer HA, compared to the HA+BB. Results were considered to be statistically significant for p<0.05.

Knees were then transported in a humidified chamber (with PBS solution) for the 3D mechanical topographical mapping analysis that was performed during the next 24 h.

3D Mechanical Toporaphical Mapping 3D mechanical topographical mapping established cartilage thickness variation in rat joint. These analyses were performed in order to determine if cartilage thickness was modified by intra articular treatment with HA and HA+BB. We compared the control (left joints, to the joints treated with HA. Cartilage thickness was investigated by topographic variability of the mechanical properties of cartilage over the articular surface (the thickness of the layer corresponding to the cartilage was measured with the XY Scan using a needle penetrating the surface vertically until to the bone).

Mechanical Properties

Mapping of the mechanical properties of cartilage joints were performed following already published procedures [Sotcheadt S. et al. J. Orthopaedic Res. 2016 DOI: 10.1002/jor.23330] Briefly, mechanical properties were measured throughout the surface of the joint, ex vivo using a multiaxial mechanical tester (Mach-1 v500css, Biomomentum). The tester records indentation curves on a 64 points grid defined on the cartilage surface prior to the experiment. Indentations were performed perpendicularly at 500 □m/s for a depth of 15 □m. All the measurement were performed in buffered saline (150 mM NaCl, pH=7.4). Thickness mapping was performed by replacing the spherical indenter by a 26G ⅜" intradermal bevel needle.

Results

Figure 34:
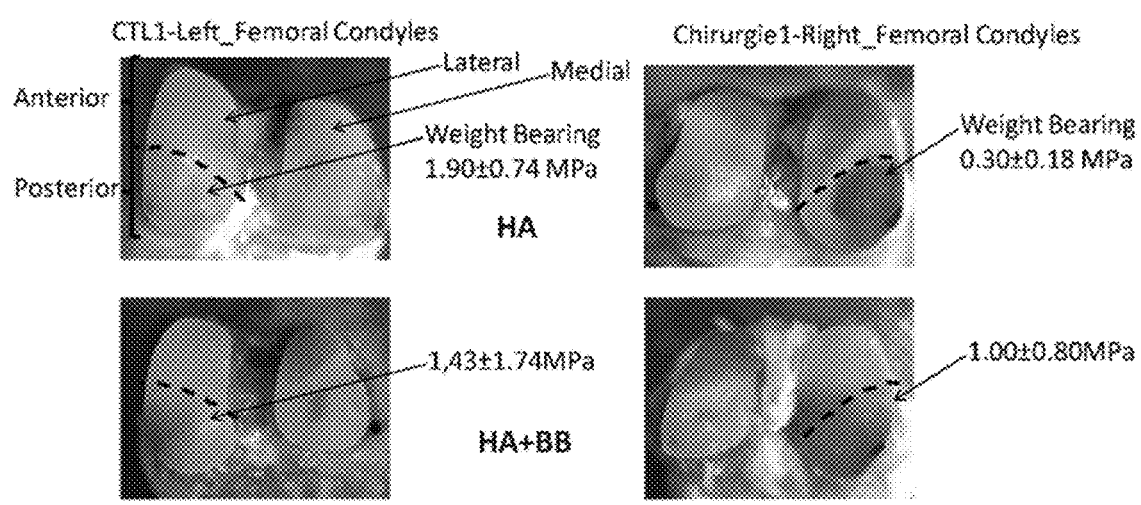
FIG. 34 shows micrographs of the left femoral condyle (left column, control without surgery) and right femoral condyle (right column) treated with either HA or HA+BB together with the corresponding modulus.
Figure 35:
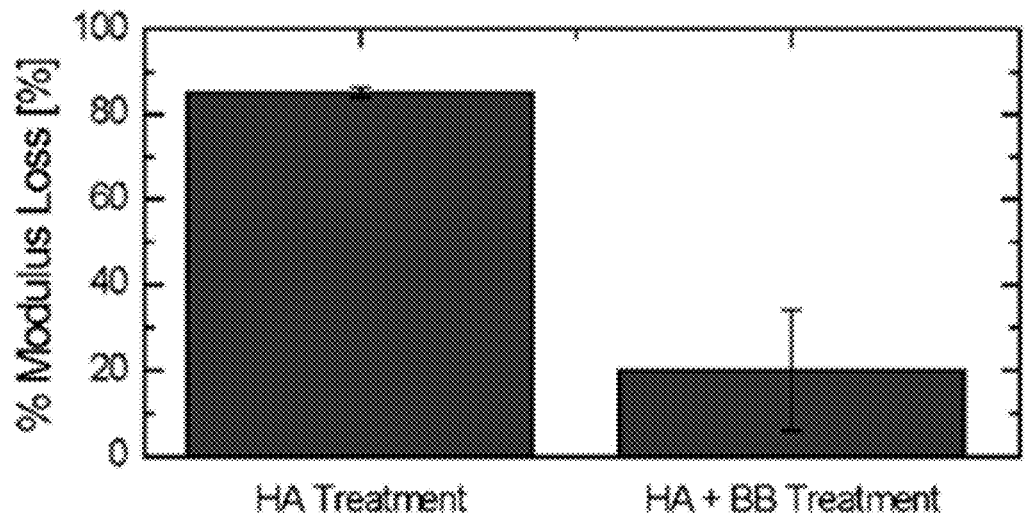
FIG. 35 shows the loss of modulus with treatment with HA or HA+BB.

FIG. 34 shows micrographs of the left femoral condyle (left column, control without surgery) and right femoral condyle (right column) treated with either HA or HA+BB. The instantaneous modulus at 15 µm of the femoral condyles is also indicated. FIG. 35 compares the loss of modulus with treatment with HA or HA+BB. As can be seen, joints treated with HA suffered from a reduction of instantaneous compression modulus of more than 80%. Joints those treated with the lubricating fluid of the invention only demonstrated a loss of instantaneous modulus of less than 20% indicating that cartilage degradation rate was significantly lowered with this treatment.

Figure 36:
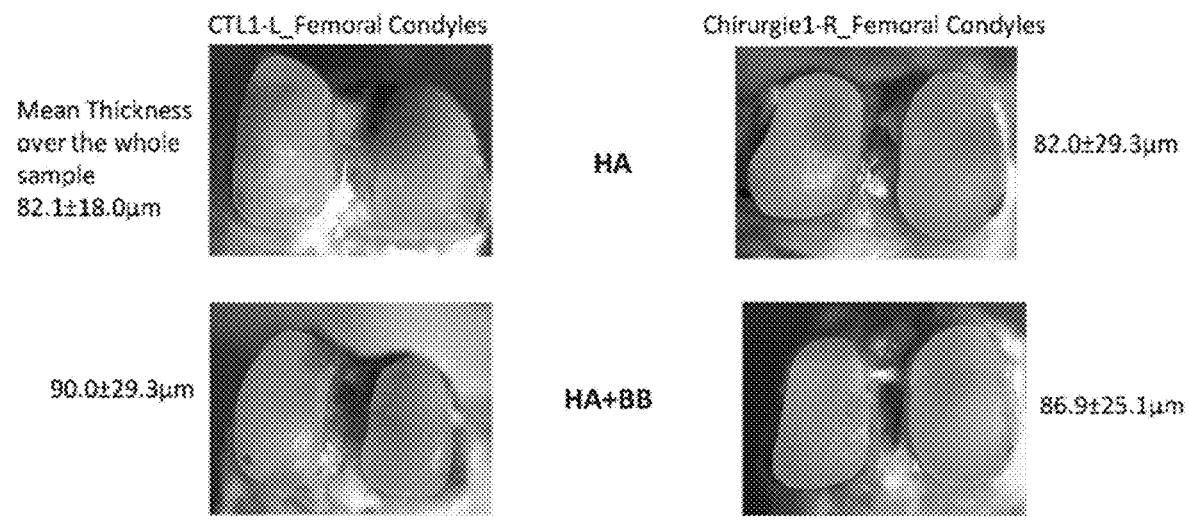
FIG. 36 shows micrographs of the left femoral condyle (left column, control without surgery) and right femoral condyle (right column) treated with either HA or HA+BB together with the corresponding mean cartilage thickness.
Figure 37:
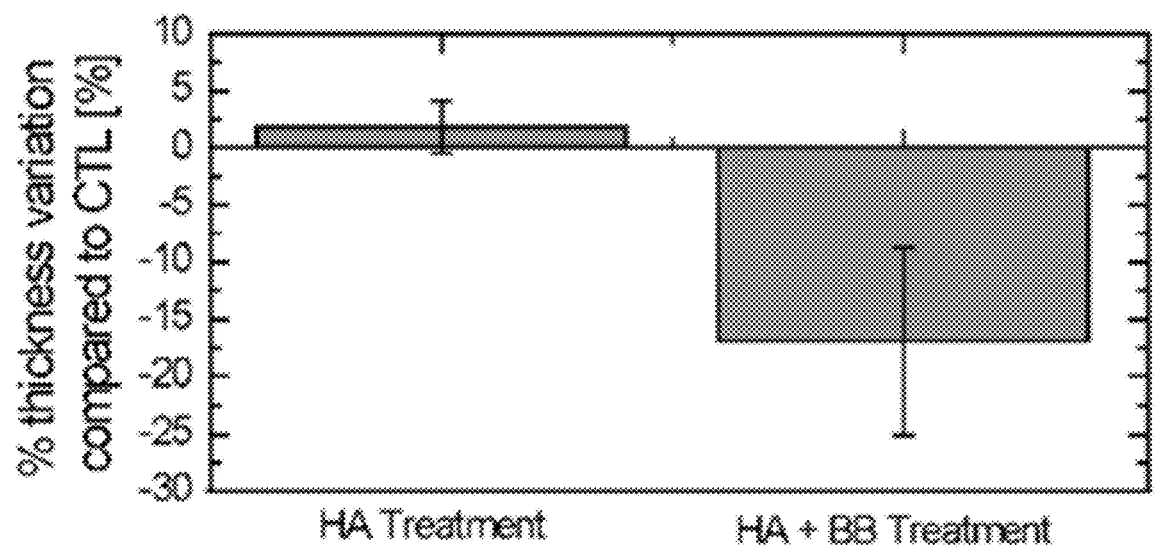
FIG. 37 shows mean cartilage thickness variation with treatment with HA or HA+BB compared to CTL.

FIG. 36 shows micrographs of the left femoral condyle (left column, control without surgery) and right femoral condyle (right column) treated with either HA or HA+BB. The mean cartilage thickness over the whole sample is also indicated. FIG. 37 shows mean cartilage thickness variation with treatment with HA or HA+BB compared to CTL.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Sotcheadt S. et al. J. Orthopaedic Res. 2016 DOI: 10.1002/jor.23330
X. Banquy et al., Bioinspired bottle-brush polymer exhibits low friction and amontons-like behavior, J. Am. Chem. Soc., 136(17):6199-6202, 2014.
Appleton et al. Arthritis Research & Therapy (2008) 10:407).
Kaufman et al. Arthritis Research & Therapy (2011) 13:R76.
(1) Holmberg, K.; Andersson, P.; Erdemir, A. Global Energy Consumption Due to Friction in Passenger Cars. Tribol. Int. 2012, 47, 221-234.
(2) Tzanakis, I.; Hadfield, M.; Thomas, B.; Noya, S. M.; Henshaw, I.; Austen, S. Future Perspectives on Sustainable Tribology. Renewable Sustainable Energy Rev. 2012, 16, 4126-4140. (3) Moro, T.; Takatori, Y.; Ishihara, K.; Konno, T.; Takigawa, Y.;
(3) Matsushita, T.; Chung, U.-i.; Nakamura, K.; Kawaguchi, H. Surface Grafting of Artificial Joints with a Biocompatible Polymer for reventing Periprosthetic Osteolysis. Nat. Mater. 2004, 3, 829-836.
(4) Klein, J. Chemistry. Repair or Replacement—a Joint Perspective. Science 2009, 323, 47-8.
(5) Dedinaite, A. Biomimetic Lubrication. Soft Matter 2012, 8, 273284.
(6) Schmidt, T. A.; Gastelum, N. S.; Nguyen, Q. T.; Schumacher, B. L.; Sah, R. L. Boundary Lubrication of Articular Cartilage—Role of Synovial Fluid Constituents. Arthritis Rheum. 2007, 56, 882-891.
(7) Liu, X.; Dedinaite, A.; Rutland, M.; Thormann, E.; Visnevskij, C.; Makuska, R.; Claesson, P. M. Electrostatically Anchored Branched Brush Layers. Langmuir 2012, 28, 15537-47.
(8) Pettersson, T.; Naderi, A.; Makuska, R.; Claesson, P. M. Lubrication Properties of Bottle-Brush Polyelectrolytes: An Afm Study on the Effect of Side Chain and Charge Density. Langmuir 2008, 24, 3336-3347.
(9) Liu, X.; Thormann, E.; Dedinaite, A.; Rutland, M.; Visnevskij, C.; Makuska, R.; Claesson, P. M. Low Friction and High Load Bearing Capacity Layers Formed by Cationic-Block-Non-Ionic Bottle-Brush Copolymers in Aqueous Media. Soft Matter 2013, 9, 5361-5371.
(10) Chen, M.; Briscoe, W. H.; Armes, S. P.; Cohen, H.; Klein, J. Polyzwitterionic Brushes: Extreme Lubrication by Design. Eur. Polym. J. 2011, 47, 511-523.
(11) Ohsedo, Y.; Takashina, R.; Gong, J. P.; Osada, Y. Surface Friction of Hydrogels with Well-Defined Polyelectrolyte Brushes. Langmuir 2004, 20, 6549-6555.

(12) Raviv, U.; Giasson, S.; Kampf, N.; Gohy, J. F.; Jerome, R.; Klein, J. Lubrication by Charged Polymers. Nature 2003, 425, 163-165.

(13) Tairy, O.; Kampf, N.; Driver, M. J.; Armes, S. P.; Klein, J. Dense, ighly Hydrated Polymer Brushes Via Modified Atom-TransferRadical-Polymerization: Structure, Surface Interactions, and Frictional Dissipation. Macromolecules 2015, 48, 140-151.

(14) Kobayashi, M.; Tanaka, H.; Minn, M.; Sugimura, J.; Takahara, A. Interferometry Study of Aqueous Lubrication on the Surface of Polyelectrolyte Brush. ACS Appl. Mater. Interfaces 2014, 6, 2036520371.

(15) Morse, A. J.; Edmondson, S.; Dupin, D.; Armes, S. P.; Zhang, Z.; Leggett, G. J.; Thompson, R. L.; Lewis, A. L. Biocompatible Polymer Brushes Grown from Model Quartz Fibres: Synthesis, Characterisationand in Situ Determination of Frictional Coefficient. Soft Matter 2010, 6, 1571-1579.

(16) Klein, J.; Kumacheva, E.; Mahalu, D.; Perahia, D.; Fetters, L. J. Reduction of Frictional Forces between Solid-Surfaces Bearing Polymer Brushes. Nature 1994, 370, 634-636.

(17) Klein, J. Shear, Friction, and Lubrication Forces between Polymer-Bearing Surfaces. Annu. Rev. Mater. Sci. 1996, 26, 581-612.

(18) Banquy, X.; Burdynska, J.; Lee, D. W.; Matyjaszewski, K.; Israelachvili, J. Bioinspired Bottle-Brush Polymer Exhibits Low Friction and Amontons-Like Behavior. J. Am. Chem. Soc. 2014, 136, 6199-6202.

(19) Sheiko, S. S.; Sumerlin, B. S.; Matyjaszewski, K. Cylindrical Molecular Brushes: Synthesis, Characterization, and Properties. Prog. Polym. Sci. 2008, 33, 759-785.

(20) Kobayashi, M.; Terayama, Y.; Kikuchi, M.; Takahara, A. Chain Dimensions and Surface Characterization of Superhydrophilic Polymer Brushes with Zwitterion Side Groups. Soft Matter 2013, 9, 5138-5148.

(21) Chen, M.; Briscoe, W. H.; Armes, S. P.; Klein, J. Lubrication at Physiological Pressures by Polyzwitterionic Brushes. Science 2009, 323, 1698-1701.

(22) Maier, G. P.; Rapp, M. V.; Waite, J. H.; Israelachvili, J. N.; Butler, A. Biological Adhesives. Adaptive Synergy between Catechol and Lysine Promotes Wet Adhesion by Surface Salt Displacement. Science 2015, 349, 628-32.

(23) Petrone, L.; Kumar, A.; Sutanto, C. N.; Patil, N. J.; Kannan, S.; Palaniappan, A.; Amini, S.; Zappone, B.; Verma, C.; Miserez, A. Mussel Adhesion Is Dictated by Time-Regulated Secretion and Molecular Conformation of Mussel Adhesive Proteins. Nat. Commun. 2015, 6, 8737.

(24) Ma, L.; Gaisinskaya-Kipnis, A.; Kampf, N.; Klein, J. Origins of Hydration Lubrication. Nat. Commun. 2015, 6, 6060.

(25) Heuberger, M.; Luengo, G.; Israelachvili, J. Topographic Information from Multiple Beam Interferometry in the Surface Forces Apparatus. Langmuir 1997, 13, 3839-3848.

(26) Perkin, S.; Goldberg, R.; Chai, L.; Kampf, N.; Klein, J. Dynamic Properties of Confined Hydration Layers. Faraday Discuss. 2009, 141, 399-413.

(27) Raviv, U.; Perkin, S.; Laurat, P.; Klein, J. Fluidity of Water Confined Down to Subnanometer Films. Langmuir 2004, 20, 532232.

(28) Fouviy, S.; Liskiewicz, T.; Kapsa, P.; Hannel, S.; Sauger, E. An Energy Description of Wear Mechanisms and Its Applications to Oscillating Sliding Contacts. Wear 2003, 255, 287-298.

What is claimed is:

1. A method of treating a disease having a degenerative mechanical component, the method comprising administering a lubricating fluid to a tissue affected by the disease, wherein the lubricating fluid comprises:

a bottle-brush polymer comprising a polymeric backbone with polymeric pendant chains with capping blocks bearing amine groups attached at both ends of said backbone, wherein the polymeric backbone with polymeric pendant chains form a copolymer of formula:

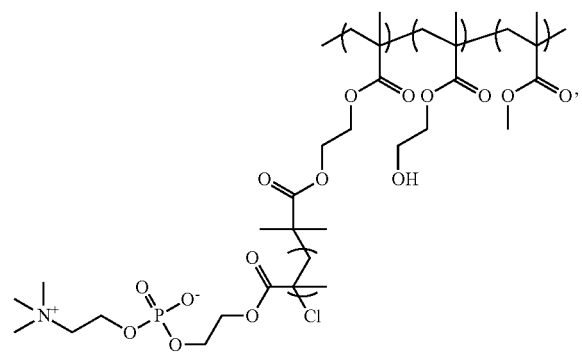

and a linear polymer which is hyaluronic acid or poly(vinylpyrrolidone) or a pharmaceutically acceptable salt thereof, the bottle-brush polymer and the linear polymer being dissolved together in a solvent.

2. The method of claim 1, wherein the disease is osteoarthritis, a lacrimal fluid production deficiency, or vaginal dryness.

3. The method of claim 2, wherein the disease is osteoarthritis.

4. The method of claim 1, wherein the lubricating fluid is administered by injection.

5. The method of claim 1, wherein the grafting ratio of the bottle-brush polymer is between about 40 and about 60%.

6. The method of claim 1, wherein the linear polymer is partially crosslinked.

7. The method of claim 1, wherein the solvent is saline.

8. The method of claim 1, wherein the lubricating fluid further comprises one or more therapeutic agent.

9. A synthetic synovial fluid comprising:

a bottle-brush polymer comprising a polymeric backbone with polymeric pendant chains with capping blocks bearing amine groups attached at both ends of said backbone, wherein the polymeric backbone with polymeric pendant chains form a copolymer of formula:

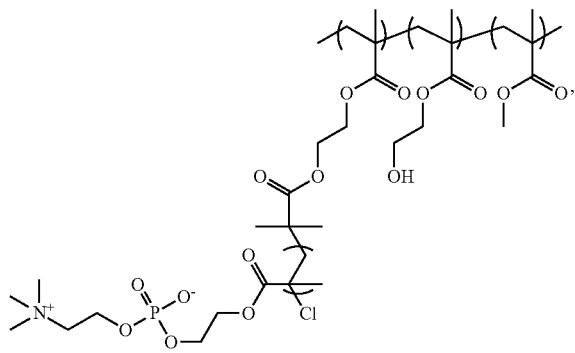

and
   a linear polymer which is hyaluronic acid or poly(vinylpyrrolidone) or a pharmaceutically acceptable salt thereof,
   the bottle-brush polymer and the linear polymer being dissolved together in a solvent.

10. The synthetic synovial fluid of claim 9, being for the treatment of osteoarthritis.

11. The synthetic synovial fluid of claim 9, wherein the grafting ratio of the bottle-brush polymer is between about 40 and about 60%.

12. The synthetic synovial fluid of claim 9, wherein the linear polymer is partially crosslinked.

13. The synthetic synovial fluid of claim 9, further comprising one or more therapeutic agent.

14. The synthetic synovial fluid of claim 9, wherein the solvent is saline.

15. A method of lubricating a tissue of a living body, the method comprising the step of contacting a lubricating fluid with said tissue, wherein the lubricating fluid comprises:
   a bottle-brush polymer comprising a polymeric backbone with polymeric pendant chains with capping blocks bearing amine groups attached at both ends of said backbone,
   wherein the polymeric backbone with polymeric pendant chains form a copolymer of formula:

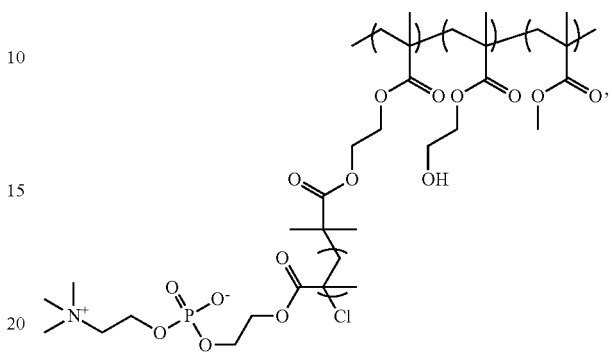

and
   a linear polymer which is hyaluronic acid or poly(vinylpyrrolidone) or a pharmaceutically acceptable salt thereof,
   the bottle-brush polymer and the linear polymer being dissolved together in a solvent.

16. The method of claim 15, wherein the tissue is an eye, skin, a surface of a ligament, a vagina, a joint, a gastrointestinal tract, a nasal duct, a tracheal duct, or a stomach.

17. The method of claim 16, wherein the tissue is a joint.

18. The method of claim 15, wherein the grafting ratio of the bottle-brush polymer is between about 40 and about 60%.

19. The method of claim 15, wherein the linear polymer is partially crosslinked.

20. The method of claim 15, wherein the lubricating fluid further comprises one or more therapeutic agent.

\* \* \* \* \*